(12) United States Patent
Graham

(10) Patent No.: US 6,573,099 B2
(45) Date of Patent: *Jun. 3, 2003

(54) GENETIC CONSTRUCTS FOR DELAYING OR REPRESSING THE EXPRESSION OF A TARGET GENE

(75) Inventor: Michael Wayne Graham, St. Lucia (AU)

(73) Assignee: Benitec Australia, Ltd., Queensland (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/100,812

(22) Filed: Jun. 19, 1998

(65) Prior Publication Data

US 2002/0168707 A1 Nov. 14, 2002

(30) Foreign Application Priority Data

Mar. 20, 1998 (AU) .............................................. PP2492

(51) Int. Cl.$^7$ .......................... C12N 5/00; C12N 15/00; C12N 15/63; A01N 63/00; A01N 43/04; A61K 48/00; A61K 31/70; C07H 21/04

(52) U.S. Cl. .................... 435/455; 435/320.1; 435/325; 424/93.21; 424/93.2; 514/44; 536/24.5

(58) Field of Search .............................. 435/69.1, 320.1, 435/325, 455; 536/23.1, 23.5, 24.5; 514/44; 800/8; 424/93.2, 93.21

(56) References Cited

U.S. PATENT DOCUMENTS

| | | | |
|---|---|---|---|
| 5,034,323 A | 7/1991 | Jorgensen et al. | 435/440 |
| 5,231,020 A | 7/1993 | Jorgensen et al. | 435/440 |
| 5,283,184 A | 2/1994 | Jorgensen et al. | 800/278 |
| 5,583,021 A | 12/1996 | Dougherty et al. | 435/440 |
| 5,686,649 A | 11/1997 | Chua et al. | 800/278 |
| 5,714,323 A | 2/1998 | Oshima et al. | 435/6 |

FOREIGN PATENT DOCUMENTS

| | | |
|---|---|---|
| EP | 0560156 A2 | 9/1993 |
| EP | 0242016 | 10/1997 |
| WO | WO 90/11682 | 10/1990 |
| WO | WO 93/23551 | 11/1993 |
| WO | WO 94/17194 | 8/1994 |
| WO | WO 95/10607 | 4/1995 |
| WO | WO 96/08558 | 3/1996 |
| WO | WO 97/01952 | 1/1997 |
| WO | WO 98/36083 | 8/1998 |
| WO | WO 98/37213 | 8/1998 |
| WO | WO 98/44138 | 10/1998 |
| WO | WO 99/15682 | 4/1999 |
| WO | WO 99/25853 | 5/1999 |
| WO | WO 99/32619 | 7/1999 |

OTHER PUBLICATIONS

Anderson WF, Nature 392:25–30, 1998.*
Verma et al Nature 389:239–242, 1997.*
Touchette, Nat. Med. 2(1) 7–8, 1996.*
Wang et al PNAS 94:11563–11566, 1997.*
Wall RJ Theriogenology 45:57–68, 1996.*
Kappel et al. Current Opinion in Biotechnology 3:548–553 1992.*
Viville, in Transgenic Animals, Houdebine (eds), Harwood academic publishers, France. pp307–321, 1997.*
Napoli, Carolyn et al., "Introduction of a Chimeric Chalcone Synthase Gene into Petunia Results in Reversible Co–Suppression of Homologous Genes in trans", *The Plant Cell*, 2: 279–289 (1990).
Lindbo, John et al., "Induction of a Highly Specific Antiviral State in Transgenic Plants: Implications for Regulation of Gene Expression and Virus Resistance", *The Plant Cell*, 5: 1749–1759 (1993).
Park, Y. et al., "Gene silencing mediated by promoter homology occurs at the level of transcription and results in meiotically heritable alterations in methylation and gene activity", *The Plant Journal*, 9: 183–194 (1996).
Waterhouse, Peter et al., "Virus resistance and gene silencing in plants can be induced by simultaneous expression of sense and antisense RNA", *Plant Biology*, 95: 13959–13964 (1998).
Smith, Neil et al., "Total Silencing by introspliced hairpin RNAs", *Nature*, 407: 319–320 (2000).
Katsuki, Motoya et al., "Conversion of Normal Behavior to Shiverer by Myelin Basic Protein Antisense cDNA in Transgenic Mice", *Science*, 241: 593–595 (1988).
Moroni, Maria Cristina et al., "EGF–R Antisense RNA Blocks Expression of the Epidermal Growth Factor Receptor and Suppresses the Transforming Phenotype of a Human Carcinoma Cell Line", *The Journal of Biological Chemistry*, 267(5): 2714–2722 (1992).
Kook, Yoon Hoh et al., "The effect of antisense inhibition of urokinase receptor in human squamous cell carcinoma on malignancy", *The EMBO Journal*, 13(17): 3983–3991 (1994).
Palauqui, Jean–Christophe et al., "Systemic acquired silencing: transgene–specific post–transcriptional silencing is transmitted by grafting from silenced stocks to non–silenced scions", *The EMBO Journal*, 16(15):–4745 (1997).

(List continued on next page.)

Primary Examiner—Scott D. Priebe
Assistant Examiner—Sumesh Kaushal
(74) Attorney, Agent, or Firm—Scully, Scott, Murphy & Presser

(57) ABSTRACT

The present invention relates generally to synthetic genes for modifying endogenous gene expression in a cell, tissue or organ of a transgenic organism, in particular a transgenic animal or plant. More particularly, the present invention provides novel synthetic genes and genetic constructs which are capable of repressing delaying or otherwise reducing the expression of an endogenous gene or a target gene in an organism when introduced thereto.

22 Claims, 28 Drawing Sheets

OTHER PUBLICATIONS

Palauqui, Jean–Christophe et al., "Transgenes are dispensable for the RNA degradation step of cosuppression", *Plant Biology*, 95: 9675–9680 (1998).

Voinnet, Olivier et al., "Systemic Spread of Sequence–Specific Transgene RNA Degradation in Plants Is Initiated by Localized Introduction of Ectopic Promoterless DNA", *Cell*, 95: 177–187 (1998).

Fire, Andrew et al., "Potent and specific genetic interference by double–stranded RNA in *Caenorhabditis elegans*", *Nature*, 391: 806–811 (1998).

Wianny, Florence et al., "Specific interference with gene function by double–stranded RNA in early mouse development", *Nature Cell Biology*, 2: 70–75 (2000).

Tuschl, Thomas et al., "Targeted mRNA degradation by double–stranded RNA in vitro", *Genes & Development*, 13: 3191–3197 (1999).

Hamilton, Andrew J. et al., "A Species of Small Antisense RNA in Posttranscriptional Gene Silencing in Plants", *Science*, 286: 950–952 (1999).

Zamore, Phillip D. et al., "RNAi: Double–Stranded RNA Directs the ATP–Dependent Cleavage of mRNA at 21 to 23 Nucleotide Intervals", *Cell*, 101: 25–33 (2000).

Hammond, Scott M. et al., "An RNA–directed nuclease mediates post–transcriptional gene silencing in Drosophila cells", *Nature*, 404: 293–296 (2000).

Caplen, Natasha J. et al., "dsRNA–mediated gene silencing in cultured Drosophila cells: a tissue culture model for the analysis of RNA interference", *Gene*, 252: 95–105 (2000).

Cogoni, Carlo et al., "Gene silencing in Neurospora crassa requires a protein homologous to RNA–dependent RNA polymerase", *Nature*, vol. 399: 166–169 (1999).

Cogoni, Carlo et al., "Posttranscriptional Gene Silencing in Neurospora by a RecQ DNA Helicase", *Science*, 286: 2342–2344 (1999).

Dalmay, Tamas et al., "An RNA–Dependent RNA Polymerase Gene in Arabidopsis Is Required for Posttranscriptional Gene Silencing Mediated by a Transgene but Not by a Virus", *Cell*, 101: 543–553 (2000).

Brigneti, Gianinna et al., "Viral pathogenicity determinants are suppressors of transgene silencing in *Nicotiana benthamiana*", *The EMBO Journal*, 17(22): 6739–6746 (1998).

Tabara, Hiroaki et al., "The rde–1 Gene, RNA Interference, and Transposon Silencing in *C. elegans*", *Cell*, 99: 123–132 (1999).

Domeier, Mary Ellen et al., "A Link Between RNA Interference and Nonsense–Mediated Decay in *Caenorhabditis elegans*", *Science*, 289: 1928–1930 (2000).

Smardon, Anne et al., "EGO–1 is related to RNA–directed RNA polymerase an functions in germ–line development and RNA interference in *C. elegans*", *Current Biology*, 10(4): 169–178 (2000).

Wassenegger, Michael et al., "Signalling in gene silencing", *Elsevier Science*, 4(6): 207–209 (1999).

Ding, Shou Wei, "RNA silencing", *Current Opinion in Biotechnology*, 11: 152–156 (2000).

Marx, Jean, "Interfering With Gene Expression", *Science*, 288: 1370–1372 (2000).

Gura, Trisha, "A silence that speaks volumes", *Nature*, 404: 804–808 (2000).

Fire, A., Xu, S.Q., Montgomery, M.K. Kostas, S.A. Driver, S.E. and Mello, C.C. (1998), "Potent and Specific Genetic Interference by Double–Standard RNA in *Caenorhabditis elegans*", *Nature*, 391 (6669): 806–811.

Garrick, D., Fiering, S., Martin, D.I. and Whitelaw, E. (1998), "Repeat–Induced Gene Silencing in Mammals", *Nature Genetics* 18(1): 56–59.

Dorer, D.R. and Henikoff, S. (1997) Transgene Repear Arrays Interact withDistant Heterochromatin and Cause Silencing in cis and trans. *Genetics* 147(3).

Pal–Bhadra, M., Bhadra U. and Birchler, J.A. (1997) "Cosuppression in Drosophila: Gene Silencing of Alcohol Dehydrogenase by White–Adh Tarnsgenes is Polycomb Dependent". *Cell* 90(3): 385–387.

Bingham, P.M. (1997) "Cosuppression Comes to the Animals". *Cell* 90(3): 385–387.

Cameron, F.H. and Jennings, P.A. (1991) "Inhibition of Gene Expression by a Short Sense Fragment". Nucleic Acids Research 19(3): 469–475.

Engdahl, H.M., et al. (1997), "A Two Unit Antisense RNA Cassette Test System for Silencing of Target Genes", *Nucleic Acids Research* 25(16): 3218–3227.

Katsuki, M., et al. (1988), "Conversion of Normal Behavior to Shiverer by Myelin Basic Protein Antisense cDNA in Transgenic Mice", *Science* 241(4865): 593–595.

Kook, Y.H., et al. (1994), "The Effect of Antisense Inhibition of Urokinase Receptor in Human Squamous Cell Carcinoma on Malignancy", *The EMBO Journal* 13(17): 3983–3991.

Lee, R.C., et al. (1993), The *C. elegans* Heterochronic Gene lin–4 Encodes Small RNAs with Antisense Complementarity to lin–14. *Cell* 75: 843–854.

Moroni, M.C., et al. (1992) EGF–R Antisense RNA Blocks Expression of the Epidermal Growth Factor Receptor and Suppresses the Transforming Phenotype of a Human Carcinoma Cell Line. *Journal of Biological Chemistry* 267(4): 2714–2722.

Nellen, W. and Lichtenstein C. (1993), "What Makes a Messenger RNA Anti–Sensitive?" *Trends in Biochemical Sciences* 18(11): 419–423.

Assaad, F.F., et al. (1993), Epigenetic Repeat–Induced Gene Silencing (RIGS) in Arabidopsis. *Plant Molecular Biology* 22(6): 1067–1085.

Balandin, T., et al. (1997), "Silencing of a β–1–3–glucanase Transgene is Overcome During Seed Formation", *Plant Molecular Biology* 34(1) 125–137.

Baulcombe, D.C. (1996) RNA as a Target and an Initiator of Post–Transcriptional Gene Silencing in Transgenic Plants, *Plant Molecular Biology* 32(1–2): 79–88.

Cogoni, C., et al. (1994), "Suppression of Gene Expression by Homologous Transgenes", *Antonie Van Leeuwenhoek* 65(3): 205–209.

Cogoni, C., et al. (1996), "Transgene Silencing of the al–1 Gene in Vegetative Cells of Neurospora is Mediated by a Cytoplasmic Effector and Does not Depend on DNA–DNA Interactions or DNA Methylation", *The EMBO Journal* 15(12): 3153–3163.

Cogoni, C., et al. (1997), "Isolations of Quelling–Defective (qde) Mutants Impaired in Posttranscriptional Transgene–Induced Gene Silencing in Neurospora Crassa". *Proceeding of the National Academy of Sciences of the United States of America* 94(19): 10233–10238.

Courtney–Gutterson, et al. (1994), "Modification of Flower Color in Florist's Chrysanthemum: Production of White-flowering Variety Through Molecular Genetics", *Biotechnology* 12(3): 268–271.

de Carvalho F., et al. (1992), "Suppression of β–1,3–glucanase Transgene Expression in Homozygous Plants", *The EMBO Journal* 11(7): 2595–2602.

de Carvalho Niebel, F. et al. (1995), "Post–transscriptional Cosuppression of β–1,3–glucanase Genes Does Not Effect Acculmulation of Transgene Nuclear mRNA", *The Plant Cell* 7(3): 347–358.

De Lange, P., et al., (1995), "Suppression of Flavonoid Flower Pigmentation Genes in Petunia Hybrida by the Introduction of Antisense and Sense Genes", *Current Topics in Microbiology and Immunology* 197: 57–75.

Depicker, A., et al. (1997), "Post–transcriptional Gene Silencing in Plants", *Current Opinion in Cell Biology* 9(3): 373–382.

English, J.J., et al. (1996), "Suppression of Virus Accumulation in Transgenic Plants Exhibiting Silencing of Nuclear Genes", *The Plant Cell* 8(2): 179–188.

Hamilton, A.J., et al. (1998), "A Transgene with Repeated DNA Causes High Frequency, Post–Transcriptional Suppression of ACC–Oxidase Gene Expression in Tomato", *The Plant Journal* 15(6): 737–746.

Jorgensen, R. (1990), "Altered Gene Expression in Plants Due to Trans Interactions Between Homologous Genes", *Trends in Biotechnology* 8(12): 340–344.

Jorgensen, R.A., et al. (1996), "Chalcone Synthase Cosuppression Phenotypes in Petunia Flowers: Comparison of Sense vs. Antisense Constructs and Single–Copy vs. Complex T–DNA Sequences", *Plant Molecular Biology* 31(5): 957–973.

Knoester, M., et al. (1997), "Modulation of Stress–Inducible Ethylene Biosynthesis by Sense and Antisense Gene Expression in Tobacco", *Plant Science* 126(2): 173–183.

Kunz, C., et al. (1996), "Developmentally Regulated Silencing and Reactivaation of Tobacco Chitinase Transgene Expression", *The Plant Journal* 10(3): 437–450.

Lee, K.Y., et al., (1997), "Post–transcriptional Gene Silencing of ACC Synthase in Tomato Results from Cytoplasmic RNA Degradation", *The Plant Journal* 12(5): 1127–1137.

Lindbo, J.A., et al., (1993), "Induction of a Highly Specific Antiviral State in transgenic Plants—Implications for Regulatio of Gene Expression and Virus Resistance", *The Plant Cell* 5(12): 1749–1759.

Matzke, M.A., et al. (1998), "Epigenetic Silencing of Plant Transgenes as a Consequence of Diverse Cellular Defence Responses", *Cellular and Molecular Life Sciences* 54(1): 94–103.

Mueller, E., et al. (1995), "Homology–dependent Resistance—Transgenic Virus Resistance in Plants Related to Homology–Dependent Gene Silencing", *The Plant Journal* 7(6): 1001–1013.

Meyer, P. (1996), "Repeat–induced Gene Silencing—Common Mechanisms in Plants and Fungi", *Biological Chemistry Hoppe–Seyler* 377(2): 87–95.

Napoli, C., et al. (1990), Introduction of a Chimeric Chalcone Synthase Gene into Petunia Results in Reversible So–Suppression of Homologous Genes in trans, *The Plant Cell* 2(4): 279–289.

Palauqui, J.C., et al. (1997), Systemic Acquired Silencing: Transgene–specific Post–transscriptional Silencing is Transmitted by Grafting from Silenced Stocks to Non–silenced scions, *The EMBO Journal* 16: 4738–4745.

Pang, S.Z., et al. (1997), "Nontarget DNA Sequences Reduce the Transgene Length Necessary for RNA–mediated Tospovirus Resistance in Transgenic Plants", *Proceedings of the National Academy of Sciences of the United States of America* 94(15): 8261–8266.

Park, Y.D., et al. (1996), "Gene Silencing Mediated by Promotor Homology Occurs at the Level of Transcription and Results in Meiotically Heritable Alterations in Methylation and Gene Activity", *The Plant Journal* 9(2): 183–194.

Que, Q., et al. (1998), "Homology–based Control of Gene Expression Patterns in Transgenic Petunia Flowers", *Developmental Genetics* 22(1): 100–109.

Romano, N., et al. (1992), "Quelling: Transient Inactivation of Gene Expression in Neurospora Crassa by Transformation with Homologous Sequences", *Molecular Microbiology* 6(22): 3343–3353.

Sadiq, M., et al. (1994), "Developmental Regulation of Antisense–mediated Gene Silencing in Dictyostelium", *Antisense Research & Development* 4(4): 263–267.

Sijen, T., et al. (1996), "RNA–mediated Virus Resistance—Role of Repeated Transgenes and Delineation of Targeted Regions", *The Plant Cell* 8(12): 2277–2294.

Singer, M.J., et al. (1995), "Genetic and Epigenetic Inactivation of Repetitive Sequences in Neurospora Crassa: RIP, DNA Methylation, and Quelling", *Current Topics in Microbiology and Immunology* 197: 165–177.

Smyth, D.R. (1997), "Gene Silencing: Cosuppression at a Distance", *Current Biology* 7(12): R793–795.

Stam, M., et al. (1997), "The Silence of Genes in Transgenic Plants", *Annals of Botany* 79(1): 3–12.

Tanzer, M.M., et al. (1997), "Characterization of Post–Transcriptionally Suppressed Transgene Expression that Confers Resistance to Tobacco Etch Virus Infection in Tobacco", *The Plant Cell* 9(8): 1411–1423.

Van der Krol, et al. (1990), "Inhibition of Flower Pigmentation by Antisense CHS Genes: Promoter and Minimal Sequence Requirements for the Antisense Effect", *Plant Molecular Biology* 14(4): 457–466.

Van der Krol, et al. (1990), "Flavonoid Genes in Petunia: Addition of a Limited Number of Gene Copies May Lead to a Suppression of Gene Expression", *The Plant Cell* 2(4): 291–299.

Vacheret, H. Nussaume, et al. (1997), "A Transciptionally Active State is Required for Post–Transcriptional Silencing (Cosuppresion) of Nitrate Reductase Host Genes and Transgenes", *The Plant Cell* 9(8): 1495–1504.

Lisziewicz et al. (1993) "Inhibition of human immunodeficiency virus type 1 replication by regulated expression of a polymeric Tat activation response RNA decoy as a strategy for gene therapy in AIDS." *Proceedings of the National Academy of Sciences of the United States of America* 90: 8000–8004.

Sun et al. (1995) "Resistance to human immunodeficiency virus type 1 infection conferred by trnasduction of human peripheral blood lymphocytes with ribozyme, antisense, or polymeric transactivation response element constructs". *Proceedings of the National Academy of Sciences of the United States of America* 92: 7272–7276.

Gervaix et al. (1997) "Multigene antiviral vectors inhibit diverse human immunodeficiency virus type 1 clades". *Journal of Virology* 71(4): 3048–3053.

Bevec et al. (1994) "Constitutive expression of chimeric Neo–Rev response element transcripts suppresses HIV–1 replication in human CD4+ T lymphocytes." *Human Gene Therapy* 5: 193–201.

Sullenger et al. (1990) "Overexpression of TAR sequences rendered cells resistant to human immundeficiency virus replication". *Cell* 63: 8254–8264.

Dorer et al. (1994) "Expansion of transgene repeats cause heterochromatin formation and gene silencing in Drosophilia". *Cell* 77: 993–1002.

Lee et al. (1994)"Inhibition of human immunodeficiency virus type 1 human T cells by a potent Rev response element decoy consisting of 13–nucleotide minimal Rev–binding domain". *Journal of Virology* 68(12): 8254–8264.

Chuah et al. (1994)"Inhibition of human immunodeficiencyvirus Type–1 by retroviral vectors expressing antisense–TAR". *Human Gene Therapy* 5: 1467–1475.

Sullenger et al. (1991 "Analysis of trans–acting response decoy RNA–mediated inhibition of human immunodeficiency virus type 1 transactivation". *Journal of Virology* 65(12): 6811–6816.

\* cited by examiner

```
                        SEQUENCE LISTING

<160> NUMBER OF SEQ ID NOS: 10

<210> SEQ ID NO 1
<211> LENGTH: 38
<212> TYPE: DNA
<213> ORGANISM: Artificial sequence
<220> FEATURE:
<223> OTHER INFORMATION: Primer Bev-1

<400> SEQUENCE: 1
cggcagatct aacaatggca ggacaaatcg agtacatc                              38

<210> SEQ ID NO 2
<211> LENGTH: 31
<212> TYPE: DNA
<213> ORGANISM: Artificial sequence
<220> FEATURE:
<223> OTHER INFORMATION: Primer Bev-2

<400> SEQUENCE: 2
cccgggatcc tcgaaagaat cgtaccactt c                                     31

<210> SEQ ID NO 3
<211> LENGTH: 29
<212> TYPE: DNA
<213> ORGANISM: Artificial sequence
<220> FEATURE:
<223> OTHER INFORMATION: Primer Bev-3

<400> SEQUENCE: 3
gggcggatcc ttagaaagaa tcgtaccac                                        29

<210> SEQ ID NO 4
<211> LENGTH: 28
<212> TYPE: DNA
<213> ORGANISM: Artificial sequence
<220> FEATURE:
<223> OTHER INFORMATION: Primer Bev-4

<400> SEQUENCE: 4
cggcagatct ggacaaatcg agtacatc                                         28

<210> SEQ ID NO 5
<211> LENGTH: 26
<212> TYPE: DNA
```

```
<213> ORGANISM: Artificial sequence
<220> FEATURE:
<223> OTHER INFORMATION: Primer Bgl-GFP

<400> SEQUENCE: 5
agatctgtaa acggccacaa gttcag                                              26

<210> SEQ ID NO 6
<211> LENGTH: 26
<212> TYPE: DNA
<213> ORGANISM: Artificial sequence
<220> FEATURE:
<223> OTHER INFORMATION: Primer GFP-Bam

<400> SEQUENCE: 6
ggatccttgt acagctcgtc catgcc                                              26

<210> SEQ ID NO 7
<211> LENGTH: 74
<212> TYPE: DNA
<213> ORGANISM: Artificial sequence
<220> FEATURE:
<223> OTHER INFORMATION: Primer SV40-1

<400> SEQUENCE: 7
gtcgacaata aaatatcttt attttcatta catctgtgtg ttggttttttt gtgtgatttt        60 tgcaaaagcc tagg                                                          74

<210> SEQ ID NO 8
<211> LENGTH: 31
<212> TYPE: DNA
<213> ORGANISM: Artificial sequence
<220> FEATURE:
<223> OTHER INFORMATION: Primer SV40-2

<400> SEQUENCE: 8
gtcgacgttt agagcagaag taacacttcc g                                       31

<210> SEQ ID NO 9
<211> LENGTH: 30
<212> TYPE: DNA
<213> ORGANISM: Artificial sequence
<220> FEATURE:
<223> OTHER INFORMATION: Forward Primer Tyr 5'

<400> SEQUENCE: 9
cccggggctt agtgtaaaac aggctgagag                                         30

<210> SEQ ID NO 10
<211> LENGTH: 31
<212> TYPE: DNA
<213> ORGANISM: Artificial sequence
<220> FEATURE:
<223> OTHER INFORMATION: Reverse Primer Tyr 3'

<400> SEQUENCE: 10
cccgggcaaa tcccagtcat ttcttagaaa c                                       31
```

GENETIC CONSTRUCTS FOR DELAYING OR REPRESSING THE EXPRESSION OF A TARGET GENE

FIELD OF THE INVENTION

The present invention relates generally to synthetic genes for modifying endogenous gene expression in a cell, tissue or organ of a transgenic organism, in particular a transgenic animal or plant. More particularly, the present invention provides novel synthetic genes and genetic constructs which are capable of repressing delaying or otherwise reducing the expression of an endogenous gene or a target gene in an organism when introduced thereto.

BACKGROUND TO THE INVENTION

Controlling metabolic pathways in eukaryotic organisms is desirable for the purposes of producing novel traits therein or introducing novel traits into a particular cell, tissue or organ of said organism. Whilst recombinant DNA technology has provided significant progress in an understanding of the mechanisms regulating eukaryotic gene expression, much less progress has been made in the actual manipulation of gene expression to produce novel traits. Moreover, there are only limited means by which human intervention may lead to a repression, delay or reduction in eukaryotic gene expression.

Current methods for downregulating gene expression using recombinant DNA technology comprise the introduction of a transgene to the cell which is capable of repressing expression of an endogenous target gene, either transcriptionally or post-transcriptionally. However, the precise mechanism is not known. Moreover, the efficiency of current approaches is low and the results are variable and unpredictable.

Attempts to improve the accuracy and predictability of methods for regulating gene expression in cells, in particular the repression, delay or reduction in expression of viral target genes in eukaryotic cells, foreign transgenes or other foreign genes introduced into cells, tissues or organs by natural means, or endogenous genes which are expressed to produce undesirable traits for a particular purpose, have been largely unsuccessful possibly due to a lack of knowledge of the precise mechanisms involved. As a consequence, the efficiency of methods currently available remains low and highly variable.

In work leading up to the present invention, the inventors sought to elucidate the mechanisms involved in down-regulating gene expression in an attempt to provide improved methods therefor. In so doing the inventors have developed a wide range of synthetic genes capable of modulating gene expression in both prokaryotic and eukaryotic cells and genetic constructs comprising same.

Bibliographic details of the publications referred to by author in this specification are collected at the end of the description. Sequence identity numbers (SEQ ID NOs.) for the nucleotide and amino acid sequences referred to in the specification are defined after the bibliography.

Throughout this specification and the claims that follow, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein, the term "derived from" shall be taken to indicate that a particular integer or group of integers has originated from the species specified, but has not necessarily been obtained directly from the specified source.

SUMMARY OF THE INVENTION

The present invention provides novel synthetic genes and improved genetic constructs comprising same for modifying endogenous or target gene expression in cells, tissues and/or organs which are either transfected or stably transformed therewith.

Accordingly, one aspect of the present invention provides a synthetic gene which is capable of modifying target gene expression in a cell, tissue or organ of a prokaryotic or eukaryotic organism which is transfected or transformed therewith, wherein said synthetic gene at least comprises a structural gene sequence comprising a nucleotide sequence which is substantially identical to the nucleotide sequence of said target gene or a derivative thereof or a complementary sequence thereto placed operably under the control of a promoter sequence which is operable in said cell, tissue or organ.

A further aspect of the invention provides a synthetic gene which is capable of modifying the expression of a target gene in a cell, tissue or organ of a prokaryotic or eukaryotic organism which is transfected or transformed therewith, wherein said synthetic gene at least comprises multiple structural gene sequences, wherein each of said structural gene sequences comprises a nucleotide sequence which is substantially identical to the nucleotide sequence of said target gene or a derivative thereof or a complementary sequence thereto and wherein said multiple structural gene sequences are placed operably under the control of a single promoter sequence which is operable in said cell, tissue or organ.

A third aspect of the present invention provides a synthetic gene which is capable of modifying the expression of a target gene in a cell, tissue or organ of a prokaryote or eukaryote which is transfected or transformed therewith wherein said synthetic gene at least comprises multiple structural gene sequences wherein each of said structural gene sequences is placed operably under the control of a promoter sequence which is operable in said cell, tissue or organ and wherein each of said structural gene sequences comprises a nucleotide sequence which is substantially identical to the nucleotide sequence of said target gene or a derivative thereof or a complementary sequence thereto.

A further aspect of the present invention provides a genetic construct which is capable of modifying the expression of an endogenous gene or target gene in a transformed or transfected cell, tissue or organ wherein said genetic construct at least comprises the synthetic gene of the invention and one or more origins of replication and/or selectable marker gene sequences.

A still further aspect of the invention provides a cell, tissue, organ or organism comprising the synthetic genes and genetic constructs described herein.

BRIEF DESCRIPTION OF THE DRAWINGS

FIG. 14 is a copy of a diagrammatic representation of the plasmid pCMV.BEV.VEB.

DETAILED DESCRIPTION OF THE PREFERRED EMBODIMENTS

Figure 1:
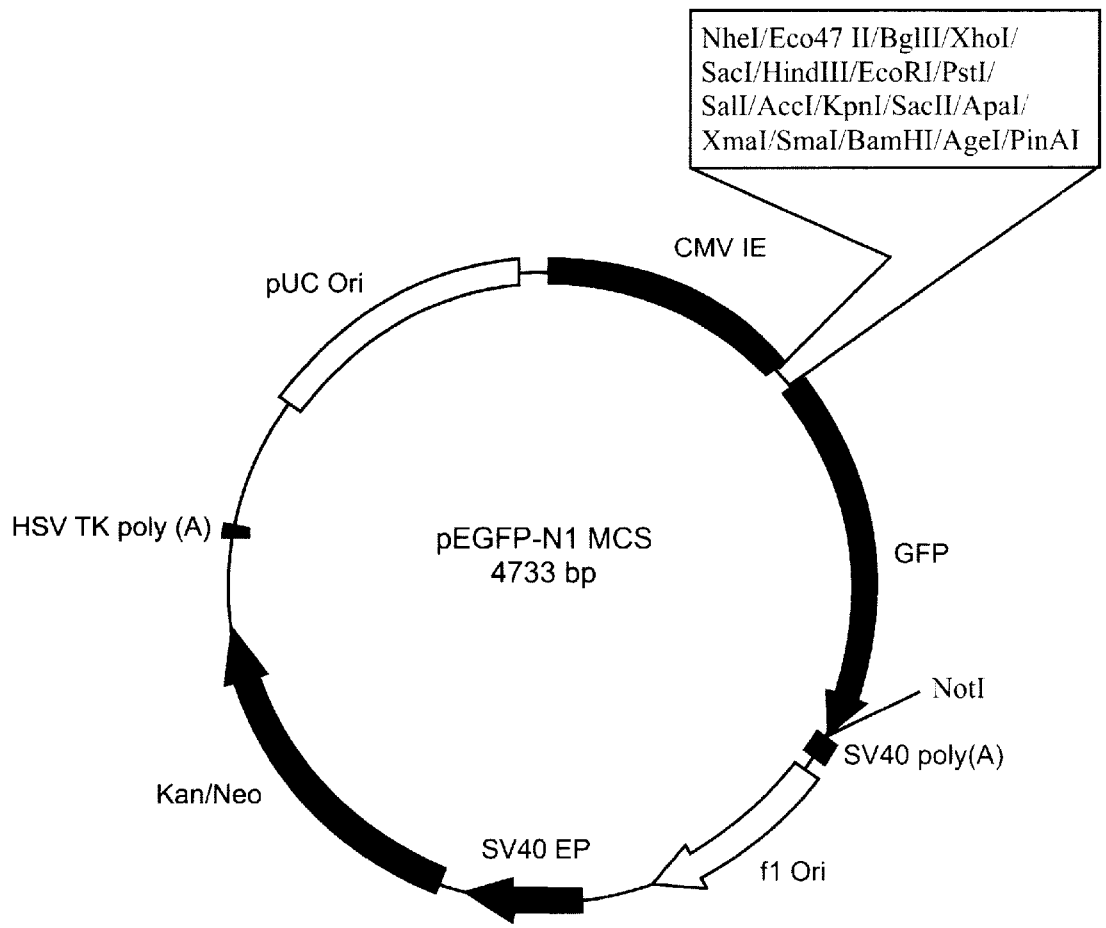
FIG. 1 is a copy of a diagrammatic representation of the plasmid pEGFP-N 1 MCS.

One aspect of the present invention provides a synthetic gene which is capable of modifying the expression of a target gene in a cell, tissue or organ wherein said synthetic gene at least comprises a structural gene comprising a nucleotide sequence which is substantially identical to the nucleotide sequence of said target gene or a derivative thereof or a complementary sequence thereto placed operably under the control of a promoter which is operable in said cell, tissue or organ.

Reference herein to a "gene" is to be taken in its broadest context and includes:

(i) a classical genomic gene consisting of transcriptional and/or translational regulatory sequences and/or a coding region and/or non-translated sequences (i.e. introns, 5'- and 3'-untranslated sequences);

(ii) mRNA or cDNA corresponding to the coding regions (i.e. exons) optionally comprising 5'- or 3'-untranslated sequences linked thereto; or (iii) an amplified DNA fragment or other recombinant nucleic acid molecule produced in vitro and comprising all or a part of the coding region and/or 5'- or 3'-untranslated sequences linked thereto.

The term "gene" is also used to describe synthetic or fusion molecules encoding all or part of a functional product, in particular a sense or antisense mRNA product or a peptide, oligopeptide or polypeptide or a biologically-active protein.

The term "synthetic gene" refers to a non-naturally occurring gene as hereinbefore defined which preferably comprises at least one or more transcriptional and/or translational regulatory sequences operably linked to a structural gene sequence.

The term "structural gene" shall be taken to refer to a nucleotide sequence which is capable of being transmitted to produce mRNA and optionally, encodes a peptide, oligopeptide, polypeptide or biologically active protein molecule. Those skilled in the art will be aware that not all mRNA is capable of being translated into a peptide, oligopeptide, polypeptide or protein, for example if the mRNA lacks a functional translation start signal or alternatively, if the mRNA is antisense mRNA. The present invention clearly encompasses synthetic genes comprising nucleotide sequences which are not capable of encoding peptides, oligopeptides, polypeptides or biologically-active proteins. In particular, the present inventors have found that such synthetic genes may be advantageous in modifying target gene expression in cells, tissues or organs of a prokaryotic or eukaryotic organism.

The term "target gene" shall be taken to refer to any gene, the expression of which is to be modified using the synthetic gene of the invention. Preferred target genes include, but are not limited to viral genes and foreign genes which have been introduced into the cell, tissue or organ or alternatively, genes which are endogenous to the cell, tissue or organ.

Wherein the target gene is a viral gene, it is particularly preferred that the viral gene encodes a function which is essential for replication or reproduction of the virus, such as but not limited to a DNA polymerase or RNA polymerase gene or a viral coat protein gene, amongst others. In a particularly preferred embodiment, the target gene comprises an RNA polymerase gene derived from a single-stranded (+) RNA virus such as bovine enterovirus (BEV), Sinbis alphavirus or a lentivirus such as, but not limited to, an immunodeficiency virus (e.g. HIV-1) or alternatively, a DNA polymerase derived from a double-stranded DNA virus such as bovine herpesvirus or herpes simplex virus I (HSVI), amongst others.

Wherein the target gene is a foreign gene, those skilled in the art will be aware that it will have been introduced to the cell, tissue or organ using transformation technology or alternatively, comprise a gene derived from a pathogen which has been introduced to said cell, tissue or organ by naturally-occurring gene transfer processes.

Particularly preferred foreign target genes include any transgene which has been introduced to the cell, tissue or organ.

Wherein the target gene is a gene which is endogenous to the cell, tissue or organ, it is particular preferred that its expression is capable of being monitored by a visual assay, enzyme assay or immunoassay. Particularly preferred endogenous target genes are those detected by visual assay means.

The synthetic genes of the present invention may be derived from naturally-occurring genes by standard recombinant techniques, the only requirement being that the synthetic gene is substantially identical at the nucleotide sequence level to at least a part of the target gene, the expression of which is to be modified. By "substantially identical" is meant that the structural gene sequence of the synthetic gene is at least about 80%–90% identical to 30 or more contiguous nucleotides of the target gene, more preferably at least about 90–95% identical to 30 or more contiguous nucleotides of the target gene and even more preferably at least about 95–99% identical or absolutely identical to 30 or ore contiguous nucleotides of the target gene.

Generally, a gene of the invention may be subjected to mutagenesis to produce single or multiple nucleotide substitutions, deletions and/or additions without affecting its ability to modify target gene expression. Nucleotide insertional derivatives of the synthetic gene of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence although random insertion is also possible with suitable screening of the resulting product.

Deletional variants are characterised by the removal of one or more nucleocides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

Accordingly, the present invention extends to homologues, analogues and derivatives of the synthetic genes described herein.

For the present purpose, "homologues" of a gene as hereinbefore defined or of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a gene as hereinbefore defined or of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example caxbohydrates, radiochemicals including radionucleotides, reporter molecules such as, but not limited to DIG, alkaline phosphatase or horseradish peroxidase, amongst others.

"Derivatives" of a gene as hereinbefore defined or of a nucleotide sequence set forth herein shall be taken to refer to any isolated nucleic acid molecule which contains significant sequence similarity to said sequence or a part thereof. Generally, the nucleotide sequence of the present invention may be subjected to mutagenesis to produce single or multiple nucleotide substitutions, deletions and/or insertions. Nucleotide insertional derivatives of the nucleotide sequence of the present invention include 5' and 3' terminal fusions as well as intra-sequence insertions of single or multiple nucleotides or nucleotide analogues. Insertional nucleotide sequence variants are those in which one or more nucleotides or nucleotide analogues are introduced into a predetermined site in the nucleotide sequence of said sequence, although random insertion is also possible with suitable screening of the resulting product being performed. Deletional variants are characterised by the removal of one or more nucleotides from the nucleotide sequence. Substitutional nucleotide variants are those in which at least one nucleotide in the sequence has been removed and a different nucleotide or nucleotide analogue inserted in its place.

Accordingly, the structural gene component of the synthetic gene may comprise a nucleotide sequence which is at least about 80% identical to at least about 30 contiguous nucleotides of an endogenous target gene, a foreign target gene or a viral target gene present in a cell, tissue or organ or a homologue, analogue, derivative thereof or a complementary sequence thereto.

Preferred structural gene components of the synthetic gene of the invention comprise at least about 20–30 nucleotides in length derived from a viral DNA polymerase, viral RNA polymerase, viral coat protein or visually-detectable gene, more particularly an RNA polymerase gene derived from a virus selected from the list comprising BEV, Sindbis alphavirus, HIV-1, bovine herpes virus and HSV1 or a visually-detectable gene which is involved in determining pigmentation, cell death or other external phenotype on a cell, tissue, organ or organism, amongst others.

In a particularly preferred embodiment, the structural gene component of the synthetic gene comprises at least about 20–30 nucleotides in length derived from the BEV RNA-dependent RNA polymerase gene or the murine tyrosinase gene or the *Escherichia coli* lac repressor gene lacI or a complementary sequence thereto.

The structural gene component may comprise a nucleotide sequence which encodes an amino acid sequence, with or without a translation start signal (ATG) or a nucleotide sequence which is complementary thereto. Those skilled in the art will be aware that, in the absence of the translation start signal in an appropriate reading frame, the mRNA encoded by the structural gene will not be translated in most eukaryotic and prokaryotic cells.

Alternatively, the structural gene may comprise a nucleotide sequence which does not encode an amino acid sequence or more commonly, comprises one or more open reading frames which encode one or more peptides, oligopeptides or polypeptides which are unrelated at the amino acid sequence level to the amino acid sequence encoded by the target gene. For example, the mRNA product of the structural gene may be inserted into the synthetic gene of the invention so as to alter or disrupt the reading frame of the structural gene and produce one or more frame shift mutations in the translation product thereof relative to the translation product encoded by the target gene, notwithstanding a substantial identity between the structural gene and the target gene on the one hand and the corresponding mRNA products of the structural gene and the target gene on the other hand. Such effects may be produced by introducing one or two nucleotide substitutions or deletions into the structural gene, relative to the target gene sequence or alternatively, by introducing a translation start codon 5'-ATG-3' upstream of any nucleotide in the structural gene which occurs at a particular position in a codon of the corresponding target gene such that the position of said nucleotide in the codon of the structural gene is altered.

Alternatively, the structural gene may encode no amino acid sequence or one or more amino acid sequences which are unrelated to the amino acid sequence encoded by the target gene wherein said structural gene is transcribed in the antisense orientation from the synthetic gene promoter, relative to the direction of transcription of the corresponding target gene. In such circumstances, the mRNA product of the structural gene will comprise a nucleotide sequence which is complementary to the nucleotide sequence in the corresponding region of the mRNA encoded by the target gene.

The present invention clearly encompasses synthetic genes wherein the structural gene component is operably connected in the sense or antisense orientation to a promoter sequence and irrespective of the capacity of said structural gene to encode an amino acid sequence which is encoded by the target gene. Accordingly, the structural gene component may further comprise 5'-untranslated region and/or 3'-untranslated region and/or intron (e.g. SV40 intron) and/or a coding region derived from the target gene or a complementary nucleotide sequence thereto.

Reference herein to a "promoter" is to be taken in its broadest context and includes the transcriptional regulatory sequences of a classical genomic gene, including the TATA box which is required for accurate transcription initiation in eukaryotic cells, with or without a CCAAT box sequence and additional regulatory elements (i.e. upstream activating sequences, enhancers and silencers). For expression in prokaryotic cells, such as bacteria, the promoter should at least contain the −35 box and −10 box sequences.

A promoter is usually, but not necessarily, positioned upstream or 5', of the structural gene component of the synthetic gene of the invention, the expression of which it regulates. Furthermore, the regulatory elements comprising a promoter are usually positioned within 2 kb of the start site of transcription of the structural gene.

In the present context, the term "promoter" is also used to describe a synthetic or fusion molecule, or derivative which confers, activates or enhances expression of an isolated nucleic acid molecule, in a cell, such as a plant, animal, insect, fungal, yeast or bacterial cell. Preferred promoters may contain additional copies of one or more specific regulatory elements, to further enhance expression of a structural gene which expression it regulates and/or to alter the spatial expression and/or temporal expression of same. For example, regulatory elements which confer inducibility on the expression of the structural gene may be placed adjacent to a heterologous promoter sequence driving expression of a nucleic acid molecule.

Placing a structural gene under the regulatory control of a promoter sequence means positioning said molecule such that expression is controlled by the promoter sequence. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for use in the synthetic genes of the present invention include viral, fungal, bacterial, animal and plant derived promoters capable of functioning in plant, animal, insect, fungal, yeast or bacterial cells. The promoter may regulate the expression of the structural gene component constitutively, or differentially with respect to cell, the tissue or organ in which expression occurs or, with respect to the developmental stage at which expression occurs, or in response to external stimuli such as physiological stresses, or pathogens, or metal ions, amongst others.

Preferably, the promoter is capable of regulating expression of a nucleic acid molecule in a eukaryotic cell, tissue or organ, at least during the period of time over which the target gene is expressed therein and more preferably also immediately preceding the commencement of detectable expression of the target gene in said cell, tissue or organ.

Accordingly, strong constitutive promoters are particularly preferred for the purposes of the present invention or promoters which may be induced by virus infection or the commencement of target gene expression.

Examples of preferred promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter and the like.

Particularly preferred promoters contemplated herein include promoters operable in eukaryotic cells, for example the SV40 early promoter, SV40 late promoter or the CMV IE promoter sequence. Those skilled in the art will readily be aware of additional promoter sequences other than those specifically described.

In the present context, the terms "in operable connection with" or "operably under the control" or similar shall be taken to indicate that expression of the structural gene is under the control of the promoter sequence with which it is spatially connected; in a cell, tissue, organ or whole organism.

In a more particularly preferred embodiment of the invention, the synthetic gene according to this aspect of the invention comprises the coding region of the BEV polymerase gene placed in the sense orientation operably under the control of the CMV IE promoter or SV40 late promoter. In an alternative embodiment, the synthetic gene comprises a nucleotide sequence derived from the coding region of the BEV polymerase gene but lacking a translation—start site, placed in the sense orientation in operable connection with the CMV IE promoter or SV40 late promoter. In a further alternative embodiment, the synthetic gene comprises a nucleotide sequence derived from the BEV polymerase gene placed in the antisense orientation relative to the BEV polymerase gene and in operable connection with the CMV IE promoter or the SV40 late promoter sequence.

For the present purposes, the term "BEV polymerase" as used herein shall be taken to refer to a structural gene, cDNA molecule, genomic gene or nucleotide sequence at least about 30–50 nucleotides in length which is derived from the nucleotide sequence of the bovine enterovirus(BEV) RNA-dependent RNA polymerase gene, including both translatable and non-translatable nucleotide sequences and nucleotide sequences which are complementary to a part of the nucleotide sequence of the full-length BEV RNA-dependent RNA polymerase gene.

In a further alternative embodiment, the synthetic gene according to this aspect of the invention comprises the coding region of a tyrosinase gene, in particular the murine tyrosinase gene, placed in the sense orientation operably under the control of the CMV IE promoter or SV40 late promoter. As with other embodiments described herein, the synthetic gene (i.e. tyrosinase gene) may lack a functional translation start site or be introduced in the antisense orientation. The present invention clearly encompasses all such embodiments.

As used herein, the term "tyrosinase gene" shall be taken to refer to a structural gene, cDNA molecule, genomic gene or nucleotide sequence which is capable of encoding the tyrosinase enzyme or a polypeptide fragment thereof or alternatively, a nucleotide sequence which is complementary to said structural gene, cDNA molecule, genomic gene or nucleotide sequence. Particularly preferred tyrosinase genes for use in the performance of the present invention include, but are not limited to, those described by Kwon et at (1988) and homologues, analogues and derivatives thereof and complementary nucleotide sequences thereto.

In still a further alternative embodiment, the synthetic gene according to this aspect of the invention comprises the coding region of the lacI gene, placed in the sense orientation operably under the control of the CMV IE promoter or SV40 late promoter. As with other embodiments described herein, the synthetic gene (i.e. E. coli lacI gene) may lack a functional translation start site or be introduced in the antisense orientation. The present invention clearly encompasses all such embodiments.

As used herein, the term "lacI gene" shall be taken to refer to a structural gene, cDNA molecule, genomic gene or nucleotide sequence which is capable of encoding a polypeptide repressor of the lacZ gene which encodes the enzyme β-galactosidase or alternatively, a nucleotide sequence which is complementary to said structural gene, cDNA molecule, genomic gene or nucleotide sequence. Those skilled in the art will be aware that the lac repressor is a DNA-binding protein which acts on the lac operator-promoter sequence. In the presence of one of a variety of β-galactosides, the affinity of the lac repressor for the lac operator-promoter sequence is lowered, thereby allowing RNA polymerase to bind the lac operator-promoter region to activate transcription of the lac operon.

Standard methods may be used to produce the structural genes of the present invention, in particular the BEV polymerase and tyrosinase genes which are derived from publicly available material. For example, the BEV polymerase and tyrosinase genes may be amplified using the polymerase chain reaction or alternatively, isolated using standard hybridisation techniques known to those skilled in the art.

For the purposes of nomenclature, the nucleotide sequence of the cDNA encoding murine tyrosinase is publicly available under GenBank Accession No. M20234.

A second aspect of the present invention provides a synthetic gene which is capable of modifying the expression of a target gene in a cell, tissue or organ, wherein said synthetic gene at least comprises multiple structural gene sequences wherein each of said structural gene sequences comprises a nucleotide sequence which is substantially identical to the nucleotide sequence of the target gene or a derivative thereof or a complementary sequence thereto and wherein said multiple structural gene sequences are placed operably under the control of a single promoter sequence which is operable in said cell, tissue or organ.

As used herein, the term "multiple structural gene sequences" or similar term shall be taken to refer to any number of structural genes as defined herein which is greater than or equal to two. Accordingly, a multiple structural gene sequence may comprise a tandem repeat or concatemer of two or more identical nucleotide sequences or alternatively, a tandem array or concatemer of non-identical nucleotide sequences, the only requirement being that each of the structural gene sequences contained therein is substantially identical to the target gene sequence or a complementary sequence thereto. In this regard, those skilled in the art will be aware that a cDNA molecule may also be regarded as a multiple structural gene sequence in the context of the present invention, in so far as it comprises a tandem array or concatemer of exon sequences derived from a genomic target gene. Accordingly, cDNA molecules and any tandem array, tandem repeat or concatemer of exon sequences and/or intron sequences and/or 5'-untranslated and/or 3'-untranslated sequences are clearly encompassed by this embodiment of the invention.

Preferably, the multiple structural gene comprises at least 2–4 individual structural gene sequences, more preferably at least about 4–6 individual structural gene sequences and more preferably at least about 6–8 individual structural gene sequences.

The optimum number of structural gene sequences which may be involved in the synthetic gene of the present invention will vary considerably, depending upon the length of each of said structural gene sequences, their orientation and degree of identity to each other. For example, those skilled in the art will be aware of the inherent instability of palindromic nucleotide sequences in vivo and the difficulties associated with constructing long synthetic genes comprising inverted repeated nucleotide sequences, because of the tendency for such sequences to form hairpin loops and to recombine in vivo. Notwithstanding such difficulties, the optimum number of structural gene sequences to be included in the synthetic genes of the present invention may be determined empirically by those skilled in the art, without any undue experimentation and by following standard procedures such as the construction of the synthetic gene of the invention using recombinase deficient cell lines, reducing the number of repeated sequences to a level which eliminates or minimises recombination events and by keeping the total length of the multiple structural gene sequence to an acceptable limit, preferably no more than 5–10 kb, more preferably no more than 2–5 kb and even more preferably no more than 0.5–2.0 kb in length.

In an alternative embodiment, each structural gene contained within the multiple structural gene unit of the subject synthetic gene may comprise a nucleotide sequence which is substantially identical to a different target gene in the same organism. Such an arrangement may be of particular utility when the synthetic gene is intended to provide protection against a pathogen in a cell, tissue or organ, in particular a viral pathogen, by modifying the expression of viral target genes. For example, the multiple structural gene may comprise nucleotide sequences which are substantially identical to two or more target genes selected from the list comprising DNA polymerase, RNA polymerase and coat protein or other target gene which is essential for viral infectivity, replication or reproduction. However, it is preferred with this arrangement that the structural gene units are selected such that the target genes to which they are substantially identical are normally expressed at approximately the same time (or later) in an infected cell, tissue or organ as (than) the multiple structural gene of the subject synthetic gene is expressed under control of the promoter sequence. This means that the promoter controlling expression of the multiple structural gene will usually be selected to confer expression in the cell, tissue or organ over the entire life cycle of the virus when the viral target genes are expressed at different stages of infection.

The individual structural gene units of the multiple structural gene according to the embodiments described herein may be spatially connected in any orientation relative to each other, for example head-to-head, head-to-tail or tail-to-tail and all such configurations are within the scope of the invention.

Preferably, the multiple structural gene unit comprises two structural genes in a head-to-tail or head-to-head configuration. More preferably, the multiple structural gene unit comprises two identical or substantially identical structural genes or a homologue, analogue or derivative thereof in a head-to-tail configuration as a direct repeat or alternatively, in a head-to-head configuration as an inverted repeat or palindrome.

In a particularly preferred embodiment, the multiple structural gene unit comprises two identical or substantially identical structural genes comprising nucleotide sequences derived from the BEV polymerase or tyrosinase gene or a homologue, analogue or derivative thereof, placed in a head-to-head or head-to-tail configuration.

According to this aspect of the invention, wherein the multiple structural gene or any individual structural gene unit thereof is intended to be both transcribed and translated, a translation start signal may be included at the 5' end of that open reading frame. In a particularly preferred embodiment, the structural gene unit which is positioned nearer the 5' end of the synthetic gene comprises an in-frame translation start signal of facilitate translation of the first open reading frame of the multiple structural gene in a cell, tissue or organ into which the synthetic gene is introduced. Those skilled in the art will be aware that it is also possible to produce a fusion polypeptide from such an arrangement provided that the individual structural gene units are positioned such that their open reading frames are in-frame with respect to each other or alternatively, the individual structural gene units are separated by intron/exon splice boundary sequences such that splicing of the mRNA product of the synthetic gene produces a translatable mRNA wherein the said open reading frames are in-frame with respect to each other. Such embodiments are clearly contemplated by the present invention. Intron/exon splice junction sequences are well-known in the art and the skilled person would readily be able to introduce such sequences to the 5'- and 3'- ends of a structural gene unit of the synthetic genes described herein.

The individual structural genes comprising the multiple structural gene unit may be further spatially separated by the addition of a linker molecule or "stuffer fragment" there between. The stuffer fragment may comprise any combination of nucleotide or amino acid residues, carbohydrate molecules or oligosaccharide molecules or carbon atoms or a homologue, analogue or derivative thereof which is capable of being linked covalently to a nucleic acid molecule.

Preferably, embodiment, the stuffer fragment comprises a sequence of nucleotides or a homologue, analogue or derivative thereof.

More preferably, the stuffer fragment comprises a sequence of nucleotides of at least about 10–50 nucleotides in length, even more preferably at least about 50–100 nucleotides in length and still more preferably at least about 100–500 nucleotides in length.

Wherein the multiple structural gene unit comprises intron/exon splice junction sequences, the stuffer fragment may serve as an intron sequence placed between the 3'-splice site of the structural gene nearer the 5'-end of the gene and the 5'- splice site of the next downstream structural gene. Alternatively, wherein it is desirable for more than two adjacent structural genes to be translated, the stuffer fragment placed there between should not include an in-frame translation stop codon, absent intron/exon splice junction sequences at both ends of the stuffer fragment or the addition of a translation start codon at the 5' end of each structural gene unit, as will be obvious to those skilled in the art.

Preferred stuffer fragments are those which encode detectable marker proteins or biologically-active analogues and derivatives thereof, for example luciferase, β-galacturonase, β-galactosidase, chloramphenicol acetyltransferase or green fluorescent protein, amongst others.

According to this embodiment, the detectable marker or an analogue or derivative thereof serves to indicate the expression of the synthetic gene of the invention in a cell, tissue or organ by virtue of its ability to confer a specific detectable phenotype thereon, preferably a visually-detectable phenotype.

In a more particularly preferred embodiment of the invention, the multiple structural gene comprises an interrupted direct repeat or interrupted palindrome comprising two identical or substantially-identical BEV polymerase structural gene sequences or alternatively, two identical or substantially-identical tyrosinase structural gene sequences or a homologue, analogue or derivative thereof separated by a stuffer fragment comprising a nucleotide sequence which encodes green-fluorescent protein or a biologically-active analogue or derivative thereof.

As used herein, the term "green fluorescent protein" or "GFP" shall be taken to refer to a protein, polypeptide or peptide which is capable of producing a strong green fluorescence when excited with near ultraviolet radiation or blue light or a homologue, analogue or derivative thereof. Accordingly, the term "GPP gene" shall be taken to refer to a nucleotide sequence which is capable of encoding GFP or a complementary nucleotide sequence thereto. Particularly preferred GFPs and GFP genes according to the present invention are derived from the jellyfish *Aequoria victoria* as described by Prasher et al (1992) or in International Patent Publication No. WO 95/07463, amongst others.

A further aspect of the invention provides for each structural gene of the multiple structural gene unit to be placed operably under the control of a separate promoter sequence.

According to this embodiment, the promoters controlling expression of the structural gene unit are preferably different promoter sequences, to reduce competition there between for cellular transcription factors and RNA polymerases. Preferred promoters are selected from those referred to supra.

Those skilled in the art will know how to modify the arrangement or configuration of the individual structural genes as described supra to regulate their expression from separate promoter sequences.

In a particularly preferred embodiment, the multiple structural gene unit comprises two or more BEV polymerase structural genes or two or more tyrosinase structural genes wherein each of said structural genes is placed operably in connection with a different promoter sequence. More particularly preferred, the multiple structural gene unit comprises two BEV polymerase structural genes or two tyrosinase structural genes positioned as inverted repeats or direct repeats wherein one of said structural genes is placed operably in connection with the CMV IE promoter. Even more preferably, at least one of the BEV polymerase structural genes or tyrosinase genes comprising the multiple structural gene is presented in the sense orientation and comprises a translation start signal to facilitate translation of nrRNA encoded therefrom.

Those skilled in the art will be aware that the structural genes comprising the multiple structural gene unit according to this aspect of the invention are expressed as physically-distinct mRNA species and, as a consequence, wherein said mRNA species are translated, no fusion polypeptide will be produced there between. However, the present invention clearly extends to synthetic gene which comprises two or more structural genes operably connected to a first promoter sequence and one or more structural genes operably connected to one or more additional promoter sequences.

The synthetic genes described supra are capable of being modified further, for example by the inclusion of marker nucleotide sequences encoding a detectable marker enzyme or a functional analogue or derivative thereof, to facilitate detection of the synthetic gene in a cell, tissue or organ in which it is expressed. According to this embodiment, the marker nucleotide sequences will be present in a translatable format and expressed, for example as a fusion polypeptide with the translation product(s) of any one or more of the structural genes or alternatively as a non-fusion polypeptide.

Alternatively or in addition, the synthetic genes described supra may further comprise one or more transcription termination sequences placed at the 3'-end of the transcriptional unit of the synthetic gene sequence.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the synthetic genes of the present invention include the SV40 polyadenylation signal, the HSV TK polyadenylation signal, the CYC1 terminator, ADH terminator, SPA terminator, nopaline synthase (NOS) gene terminator of *Agrobacterium tumefaciens*, the terminator of the Cauliflower mosaic virus (CaMV) 35S gene, the zein gene terminator from *Zea mays*, the Rubisco small subunit gene (SSU) gene terminator sequences, subclover stunt virus (SCSV) gene sequence terminators, any rho-independent *E. coli* terminator, or the lacZ alpha terminator, amongst others.

In a particularly preferred embodiment, the terminator is the SV40 polyadenylation signal or the HSV TK polyadenylation signal which are operable in animal cells, tissues and organs or the lacZ alpha terminator which is active in prokaryotic cells.

Those skilled in the art will be aware of additional promoter sequences and terminator sequences which may be suitable for use in performing the invention. Such sequences may readily be used without any undue experimentation.

The synthetic genes of the present invention may be introduced to a suitable cell, tissue or organ without modification as linear DNA in the form of a genetic construct, optionally contained within a suitable carrier, such as a cell, virus particle or liposome, amongst others. To produce a genetic construct, the synthetic gene of the invention is inserted into a suitable vector or episome molecule, such as a bacteriophage vector, viral vector or a plasmid, cosmid or artificial chromosome vector which is capable of being maintained and/or replicated and/or expressed in the host cell, tissue or organ into which it is subsequently introduced.

Accordingly a further aspect of the invention provides a genetic construct which at least comprises the synthetic gene according to any one or more of the embodiments described herein and one or more origins of replication and/or selectable marker gene sequences.

Usually, an origin of replication or a selectable marker gene suitable for use in bacteria is physically-separated from those genetic sequences contained in the genetic construct which are intended to be expressed or transferred to a eukaryotic cell, or integrated into the genome of a eukaryotic cell.

In a particularly preferred embodiment, the origin of replication is functional in a bacterial cell and comprises the pUC or the ColE1 origin or alternatively the origin of replication is operable in a eukaryotic cell, tissue and more preferably comprises the 2 micron (2 $\mu$m) origin of replication or the SV40 origin of replication.

As used herein, the term "selectable marker gene" includes any gene which confers a phenotype on a cell in which it is expressed to facilitate the identification and/or selection of cells which are transfected or transformed with a genetic construct of the invention or a derivative thereof.

Suitable selectable marker genes contemplated herein include the ampicillin-resistance gene (Amp$^r$), tetracycline-resistance gene (Tc$^r$), bacterial kanamycin-resistance gene (Kan$^r$), is the zeocin resistance gene (Zeocin is a drug of bleomycin family which is trademark of InVitrogen Corporation), the AURI-C gene which confers resistance to the antibiotic aureobasidin A, phosphinothricin-resistance gene, neomycin phosphotransferase gene (nptII), hygromycin-resistance gene, $\beta$-glucuronidase (GUS) gene, chloramphenicol acetyltransferase (CAT) gene, green fluorescent protein- encoding gene or the luciferase gene, amongst others.

Preferably, the selectable marker gene is the nptII gene or Kan$^r$ gene or green fluorescent protein (GFP)-encoding gene.

Those skilled in the art will be aware of other selectable marker genes useful in the performance of the present invention and the subject invention is not limited by the nature of the selectable marker gene.

The present invention extends to all genetic constructs essentially as defined herein, which include further genetic sequences intended for the maintenance and/or replication of said genetic construct in prokaryotes and/or the integration of said genetic construct or a part thereof into the genome of a eukaryotic cell or organism.

The present invention further extends to an isolated cell, tissue or organ comprising the synthetic gene described herein or a genetic construct comprising same. Any standard means may be used for their introduction including cell mating, transformation or transfection procedures known to those skilled in the art or described by Ausubel et al. (1992).

The present invention is further described by reference to the following non-limiting Examples.

EXAMPLE 1

Base Plasmids

Plasmid pEGFP-N1 MCS

Plasmid pEGFP-N1 MCS (FIG. 1; Clontech) contains the CMV IE promoter operably connected to an open reading frame encoding a red-shifted variant of wild-type green fluorescent protein (GFP; Prasher et al., 1992; Chalfie et al., 1994; Inouye and Tsuji, 1994), which has been optimised for brighter fluorescence. The specific GFP variant encoded by pEGFP-N1 MCS has been disclosed by Cormack et al. (1996). Plasmid pEGFP-N1 MCS contains a multiple cloning site comprising Bg/II and BamHI sites and many other restriction endonuclease cleavage sites, located between the CMV IE promoter and the GFP open reading frame. Structural genes cloned into the multiple cloning site will be expressed at the transcriptional level if they lack a functional translation start site, however such structural gene sequences will not be expressed at the protein level (i.e. translated). Structural gene sequences inserted into the multiple cloning site which comprise a functional translation start site will be expressed as GFP fusion polypeptides if they are cloned in-frame with the GFP-encoding sequence. The plasmid further comprises an SV40 polyadenylation signal downstream of the GFP open reading frame to direct proper processing of the 3'-end of mRNA transcribed from the CMV-IE promoter sequence. The plasmid further comprises the SV40 origin of replication functional in animal cells; the neomycin-resistance gene comprising SV40 early promoter (SV40 EP in FIG. 1) operably connected to the neomycin/kanamycin-resistance gene derived from Tn5 (Kan/neo in FIG. 1) and the HSV thymidine kinase polyadenylation signal (HSV TK poly (A) in FIG. 1), for selection of transformed cells on kamanycin, neomycin or G418; the pUC19 origin of replication which is functional in bacterial cells (pUC Ori in FIG. 1); and the fl origin of replication for single-stranded DNA production (fl Ori in FIG. 1).

pCMVLacI

Plasmid pCMVLacI is a commercially-obtainable mammalian expression vector (Stratagene) comprising the lacI gene encoding the lac repressor and a gene coding for hygromycin resistance (Hyg$^r$).

Plasmid pOPRSVI/MCS

Plasmid pOPRSVI/MCS is a commercially-obtainable mammalian expression vector (Stratagene), comprising the OPRSV1 promoter sequence (a modified RSV-LTR promoter), SV40 intron sequence, lac operator sequence, multiple cloning site and thymidine kinase (TK) gene transcription terminator sequence [i.e. TK poly(A) signal].

Plasmid pSVL

Plasmid pSVL is commercially-obtainable from Pharmacia and serves as a source of the SV40 late promoter sequence. The nucleotide sequence of pSVL is also publicly available as GenBank Accession Number U13868.

Plasmid pCMV.cass

Plasmid pCMV.cass (FIG. 2) is an expression cassette for driving expression of a structural gene sequence under control of the CMV-IE promoter sequence. Plasmid pCMV.cass was derived from pEGFP-N1 MCS by deletion of the GFP open reading frame as follows: Plasmid pEGFP-N1 MCS was digested with PinAI and Not I, blunt-ended using PfuI polymerase and then re-ligated. Structural gene sequences are cloned into pCMV.cass using the multiple cloning site, which is identical to the multiple cloning site of pEGFP-N1 MCS, except it lacks the PinAI site.

Plasmid pCR2.1

Plasmid pCR2.1 is commercially available from Stratagene and comprises the lacZ promoter sequence and lacZ-α transcription terminator, with a cloning site for the insertion of structural gene sequences there between. Plasmid pCR2.1 is designed to clone nucleic acid fragments by virtue of the A-overhang frequently synthesized by Taq polymerase during the polymerase chain reaction. The plasmid further comprises the ColE1 and fl origins of replication and kanamycin-resistance and ampicillin-resistance genes.

Plasmid pCR.Bgl-GFP-Bam

Figure 3:
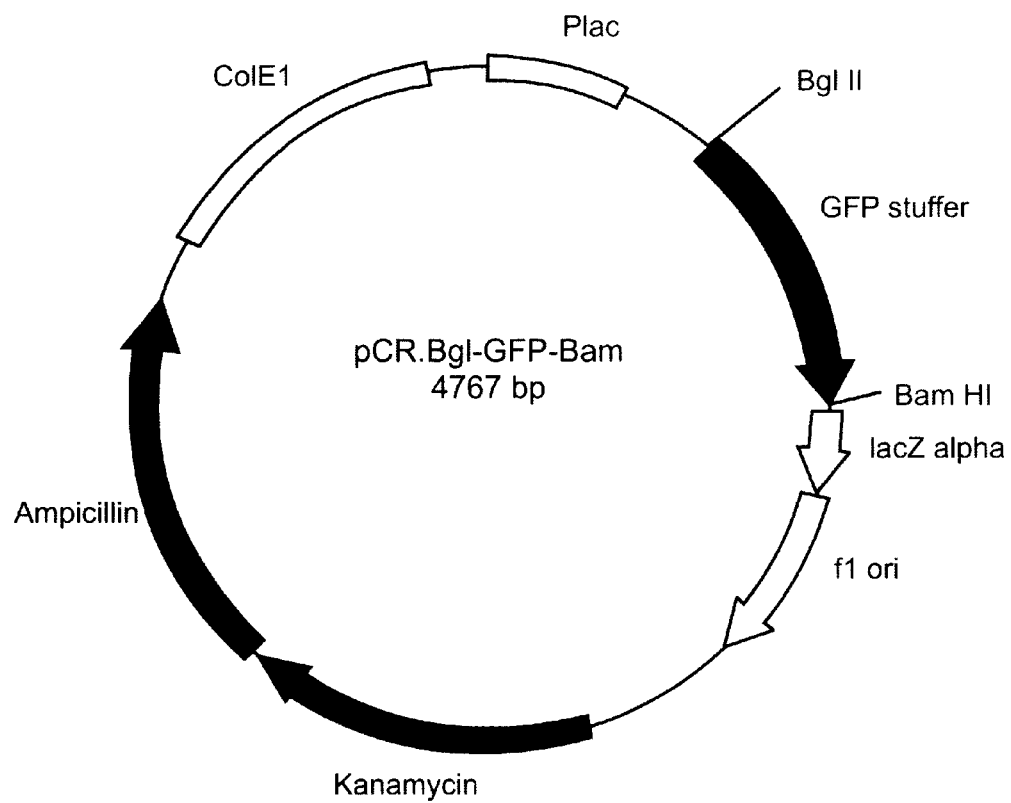
FIG. 3 is a copy of a diagrammatic representation of the plasmid pCR.Bgl-GPP-Bam.

Plasmid pCR.Bgl-GFP-Bam (FIG. 3) comprises an internal region of the GFP open reading frame derived from plasmid pEGFP-N1 MCS (FIG. 1) placed operably under the control of the lacZ promoter. To produce this plasmid, a region of the GFP open reading frame was amplified from pEGFP-N1 MCS using the amplification primers Bgl-GFP (SEQ ID NO:5) and GFP-Bam (SEQ ID NO:6) and cloned into plasmid pCR2.1. The internal GFP-encoding region in plasmid pCR.Bgl-GFP-Bam lacks functional translational start and stop codons.

Plasmid pCR.SV40L

Figure 4:
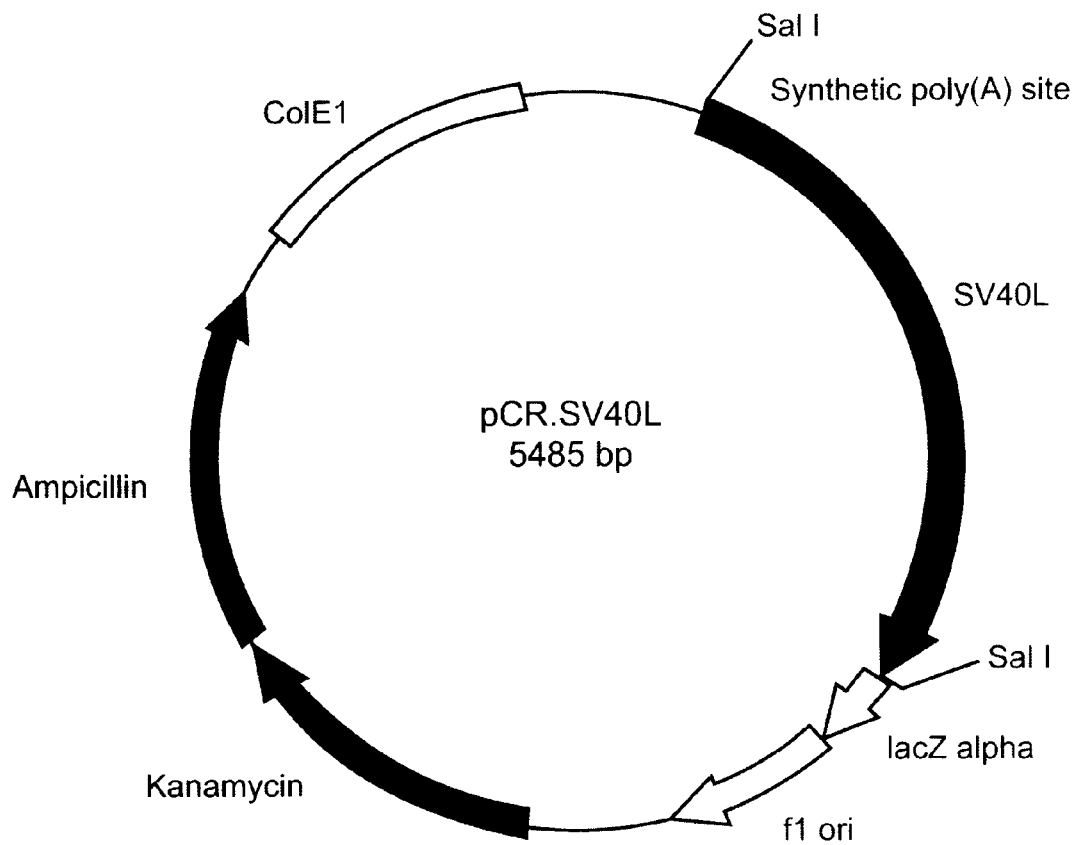
FIG. 4 is a copy of a diagrammatic representation of the plasmid pCR.SV40L.

Plasmid pCR.SV40L (FIG. 4) comprises the SV40 late promoter derived from plasmid pSVL (GenBank Accession No. U13868; Pharmacia), cloned into pCR2.1 (Stratagene). To produce this plasmid, the SV40 late promoter was amplified using the primers SV40-1 (SEQ ID NO:7) and SV40-2 (SEQ ID NO:8) which comprise Sal I cloning sites to facilitate sub-cloning of the amplified DNA fragment into pCMV.cass. SEQ ID No. 7 also contains a synthetic poly (A) site at the 5' end, such that the amplicification product comprises the synthetic poly(A) site at the 5' end of the SV40 promoter sequence.

Plasmid pCMV.SV40L.cass

Figure 5:
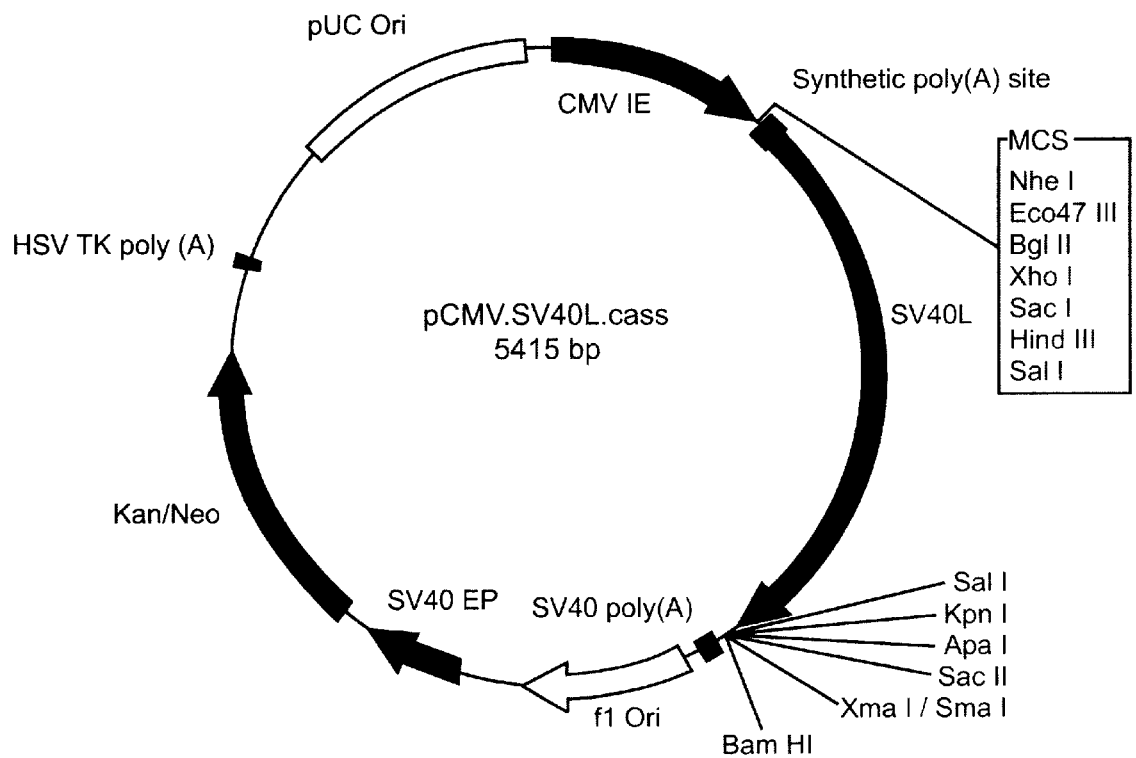
FIG. 5 is a copy of a diagrammatic representation of the plasmid pCMV.SV40L.cass.

Plasmid pCMV.SV40L.cass (FIG. 5) comprises the synthetic poly A site and the SV40 late promoter sequence from plasmid pCR.SV40L (FIG. 4), sub-cloned as a Sal I fragment, into the Sal I site of plasmid pCMV.cass (FIG. 2), such that the CMV-IE promoter and SV40 late promoter sequences are capable of directing transcription in the same direction. Accordingly, the synthetic poly(A) site at the 5' end of the SV40 promoter sequence is used as a transcription terminator for structural genes expressed from the CMV IE promoter in this plasmid, which also provides for the insertion of said structural gene via the multiple cloning site present between the SV40 late promoter and the synthetic poly(A) site (FIG. 5). The multiple cloning sites are located behind the CMV-IE and SV40 late promoters, including BamHI and BglII sites.

EXAMPLE 2

BEV Polymerase-containing Genes

Plasmid pCR.BEV.1

The BEV RNA-dependent RNA polymerase coding region was amplified as a 1,385 bp DNA fragment from a full-length cDNA clone encoding same, using the primers designated BEV-1 (SEQ ID NO:1) and BEV-2 (SEQ ID NO:2), under standard amplification conditions. The amplified DNA contained a 5'-Bgl II restriction enzyme site, derived from the BEV-1 primer sequence and a 3'BamHI restriction enzyme site, derived from the BEV-2 primer sequence. Additionally, as the BEV-1 primer sequence contains a translation start signal 5'-ATG-3' engineered at positions 15–17 of SEQ ID NO:1, the amplified BEV polymerase structural gene comprises the start site in-frame with BEV polymerase-encoding nucleotide sequences, Thus, the amplified BEV polymerase structural gene comprises the ATG start codon immediately upstream (i.e. juxtaposed) to the BEV polymerase-encoding sequence. There is no translation stop codon in the amplified DNA.

Figure 6:
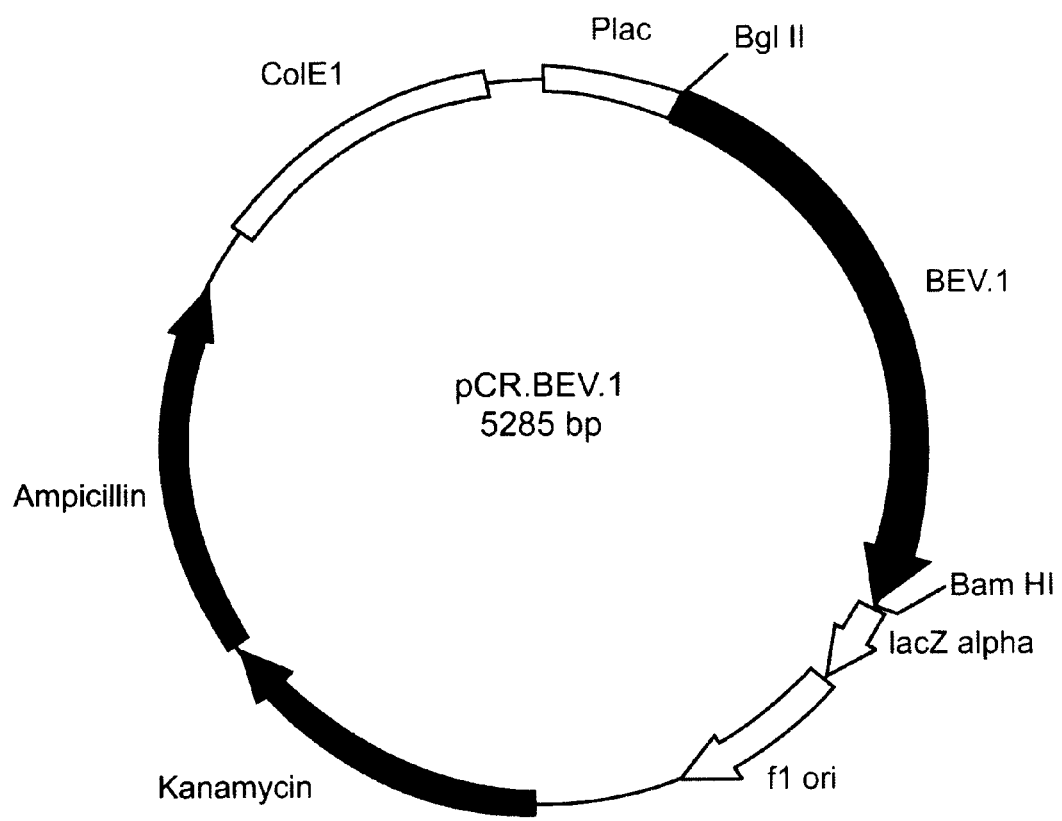
FIG. 6 is a copy of a diagrammatic representation of the plasmid pCR.BEV.1.

The amplified BEV polymerase structural gene was cloned into plasmid pCR2.1 to produce pCR.BEV.1 (FIG. 6).

Plasmid pCR.BEV.2

Figure 7:
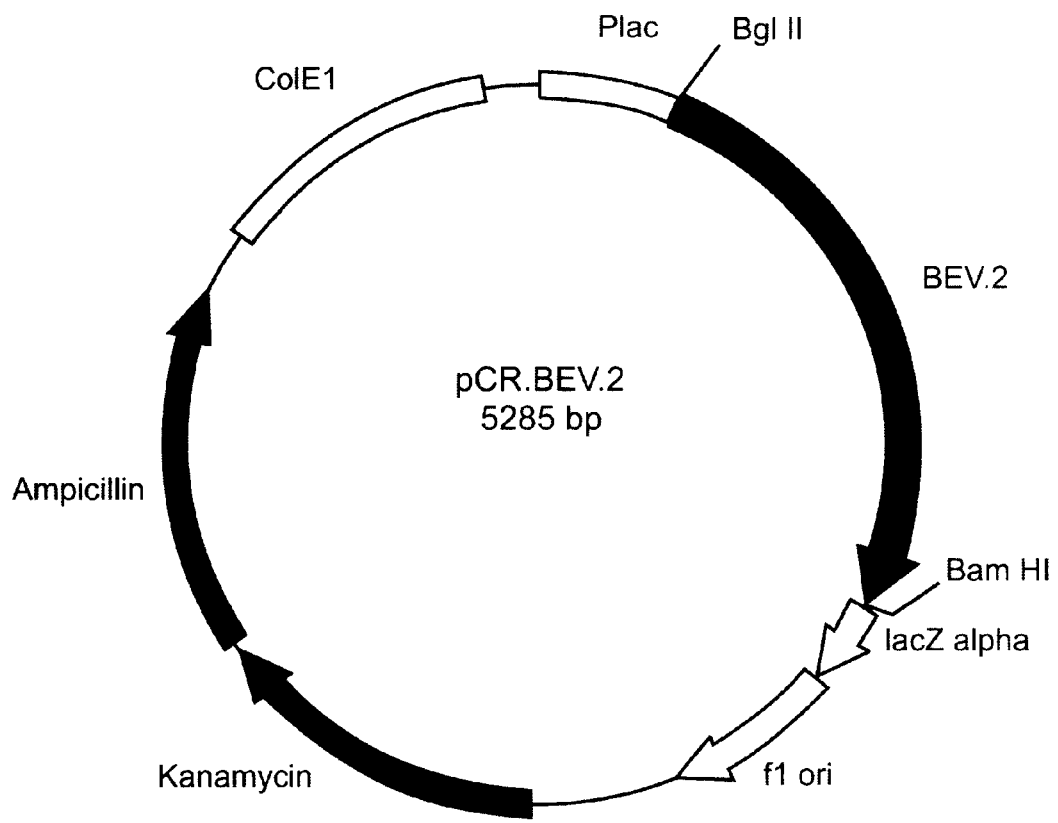
FIG. 7 is a copy of a diagrammatic representation of the plasmid pCR.BEV.2.

The complete BEV polymerase coding region was amplified from a full-length cDNA clone encoding same, using primers BEV-1 (SEQ ID NO:1) and BEV-3 (SEQ ID NO:3). Primer BEV-3 comprises a BamHI restriction enzyme site at positions 5 to 10 inclusive of SEQ ID NO:3 and the complement of a translation stop signal at positions 11 to 13 of SEQ ID NO:3. As a consequence, an open reading frame comprising a translation start signal and translation stop signal, contained between the Bgl II and BamHI restriction sites. The amplified fragment was cloned into pCR2.1 to produce plasmid pCR2.BEV.2 (FIG. 7).

Plasmid pCR.BEV.3

Figure 8:
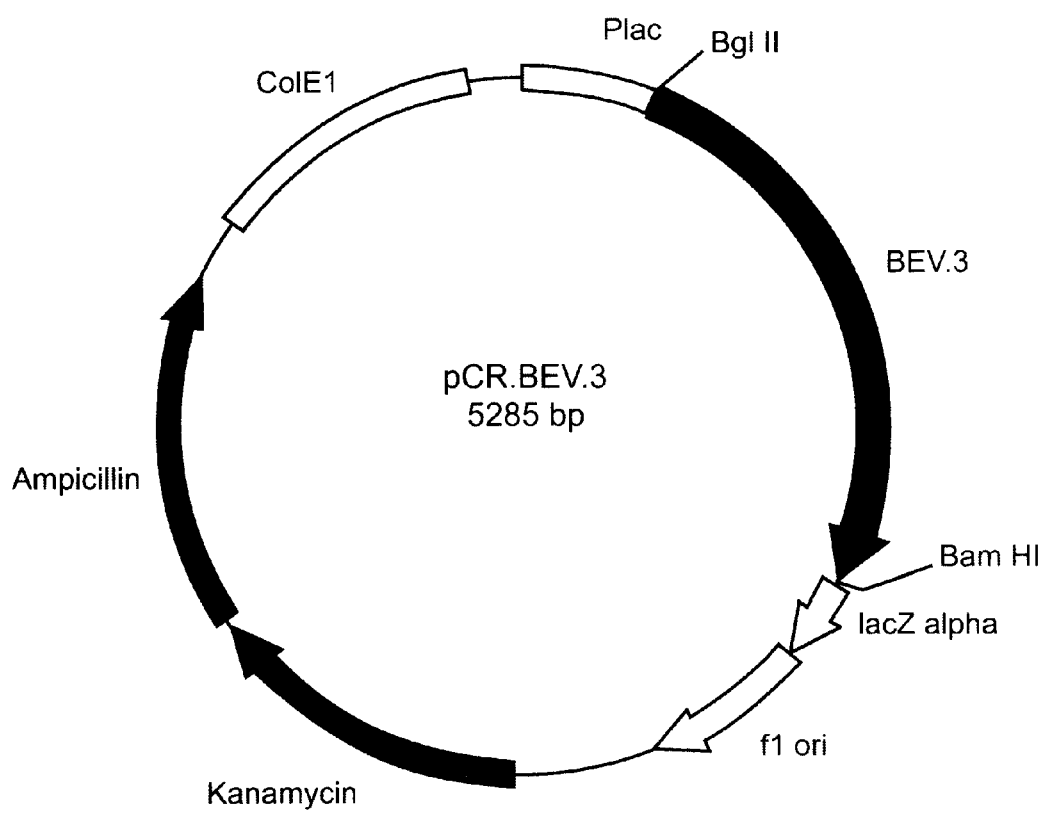
FIG. 8 is a copy of a diagrammatic representation of the plasmid pCR.BEV.3.

A non-translatable BEV polymerase structural gene was amplified from a full-length BEV polymerase cDNA clone using the amplification primers BEV-3 (SEQ ID NO:3) and BEV4 (SEQ ID NO:4). Primer BEV-4 comprises a BglII cloning site at positions 5–10 of SEQ ID NO:4 and sequences downstream of this BglII site are homologous to nucleotide sequences of the BEV polymerase gene. There is no fictional ATG start codon in the amplified DNA product of primers BEV-3 and 13BV4. The BEV polymerase is expressed as part of a polyprotein and, as a consequence, there is no ATG translation start site in this gene. The amplified DNA was cloned into plasmid pCR2.1 to yield plasmid pCR.BEV.3 (FIG. 8).

EXAMPLE 3

Synthetic Genes Comprising a BEV Polymerase Structural Gene Operably Connected to the CMV-IE Promoter Sequence Plasmid pEGFP.BEV.1

Figure 9:
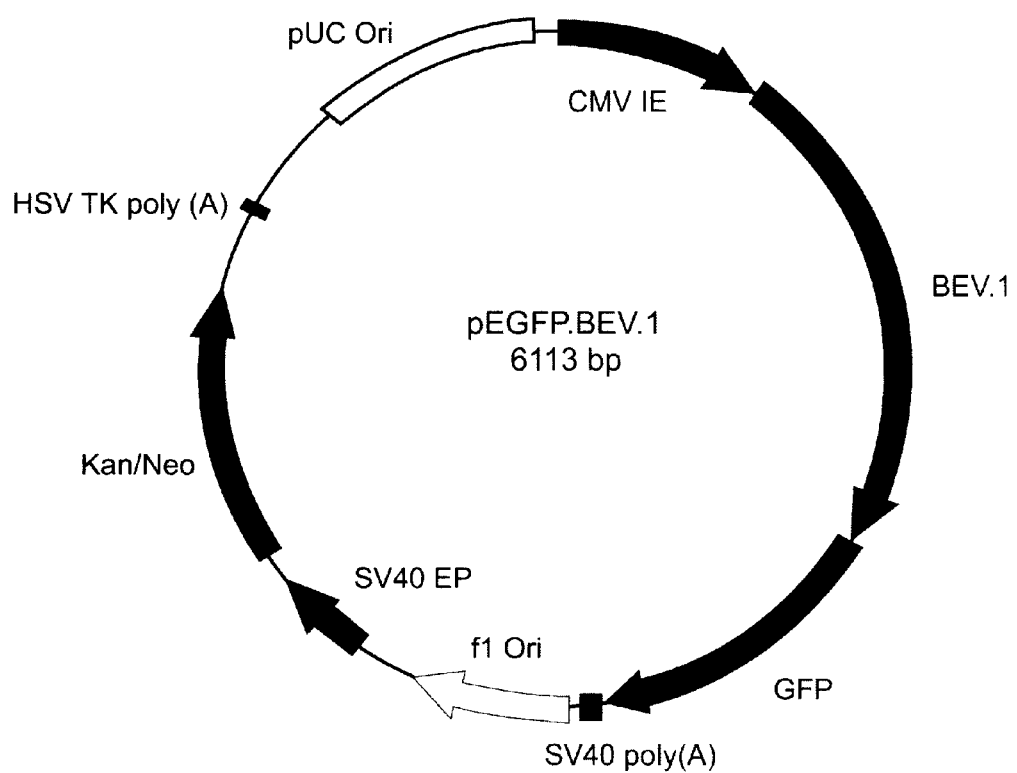
FIG. 9 is a copy of a diagrammatic representation of the plasmid pEGFP.BEV.1.

Plasmid pEGFP.BEV.1 (FIG. 9) is capable of expressing the BEV polymerase structural gene as a GFP fusion polypeptide under the control of the CMV-IE promoter sequence. To produce plasmid pEGFP.BEV.1, the BEV polymerase sequence from pCR.BEV.1 (FIG. 6) was cloned as a BglII-to-BamHI fragment into BglII/BamHI-digested pEGFP-N1 MCS (FIG. 1).

Plasmid pCMV.BEV.2

Figure 2:
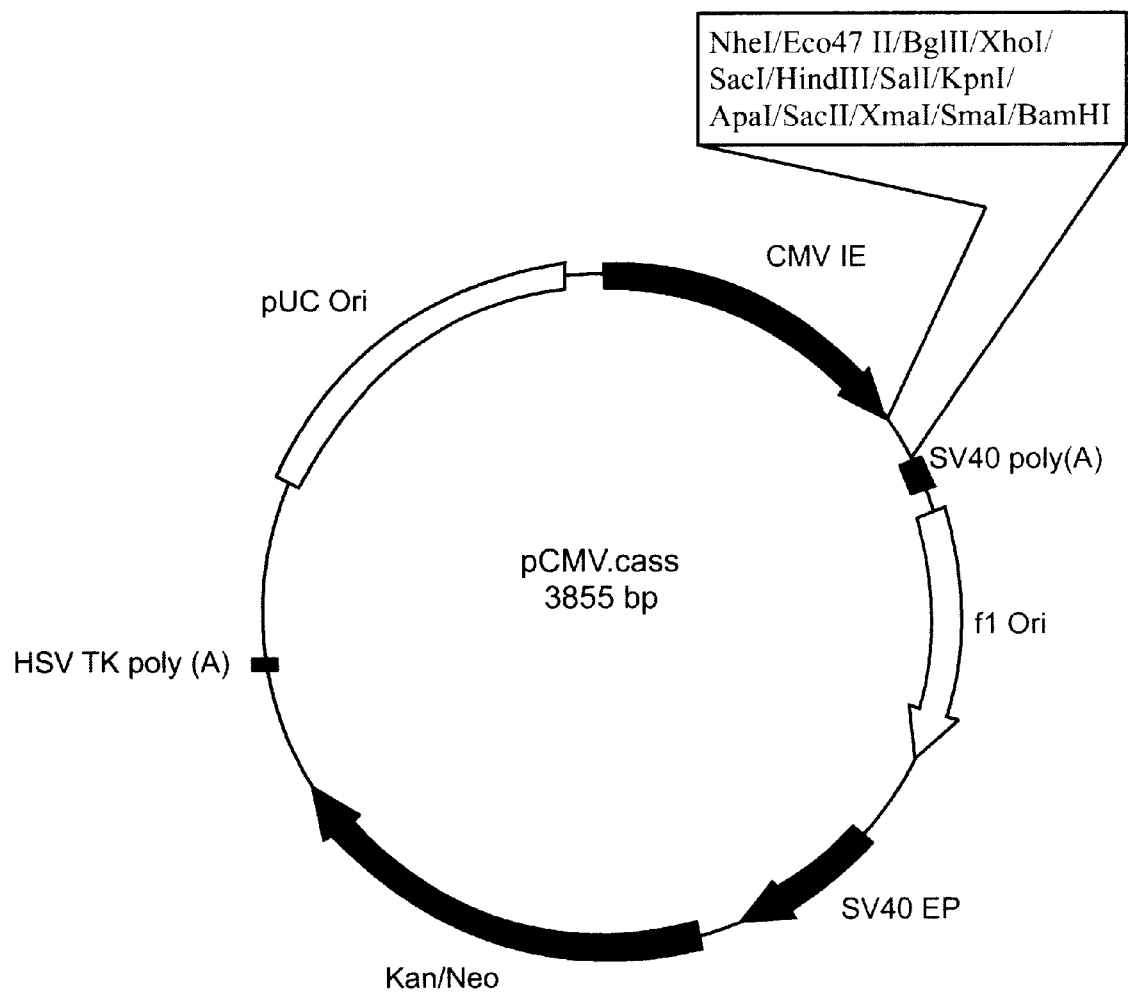
FIG. 2 is a copy of a diagrammatic representation of the plasmid pCMV.cass.
Figure 10:
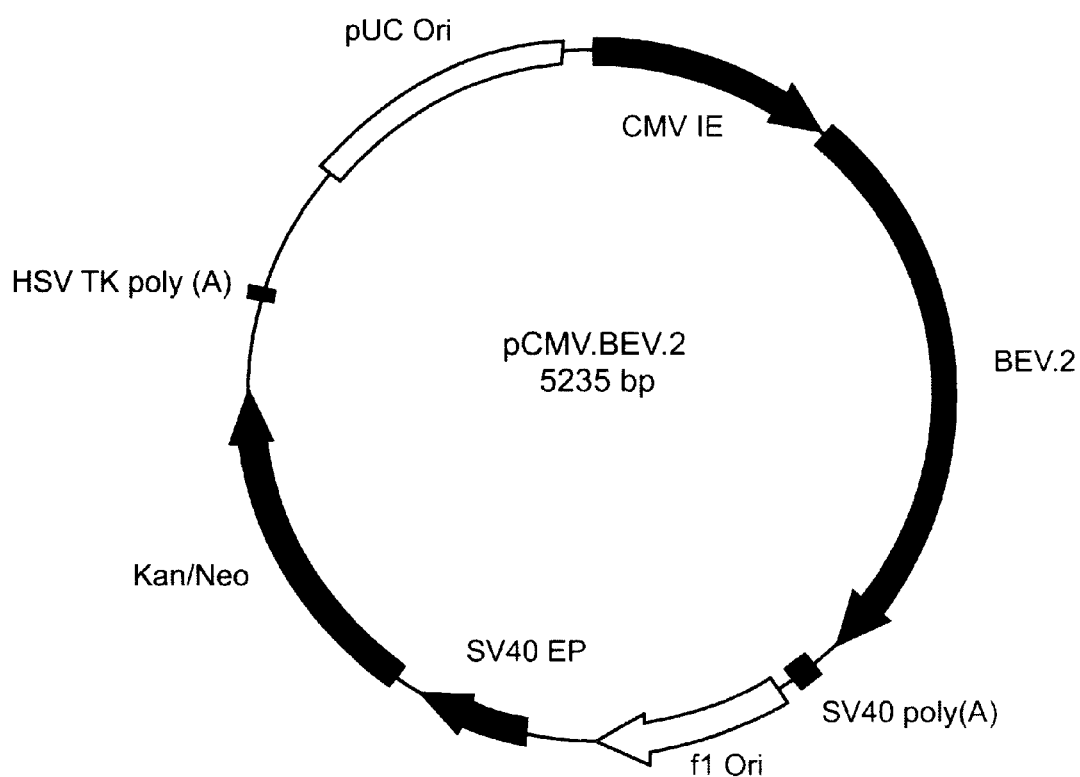
FIG. 10 is a copy of a diagrammatic representation of the plasmid pCMV.BEV.2.

Plasmid pCMV.BEV.2 (FIG. 10) is capable of expressing the entire BEV polymerase open reading frame under the control of CMV-IE promoter sequence. To produce pCMV.BEV.2, the BEV polymerase sequence from pCR-.BEV.2 (FIG. 7) was sub-cloned in the sense orientation as a BglII-to-BamHI fragment into BglII/BamHI-digested pCMV.cass (FIG. 2).

Plasmid pCMV.VEB

Figure 11:
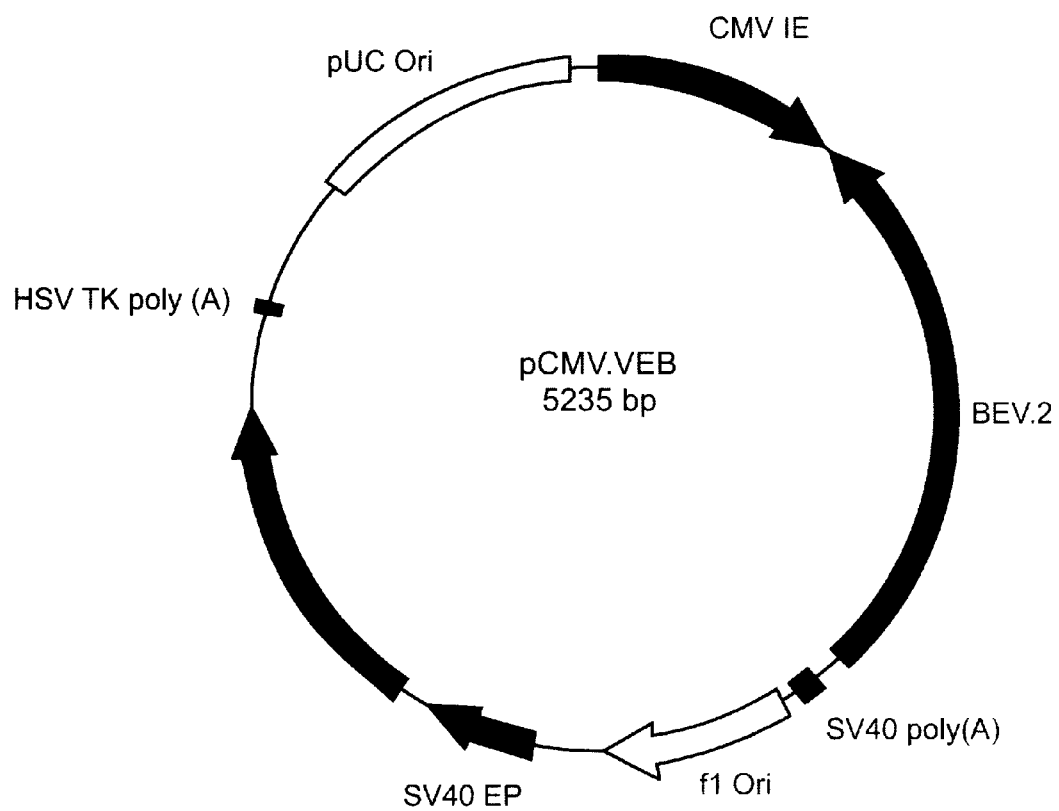
FIG. 11 is a copy of a diagrammatic representation of the plasmid pCMV.VEB.

Plasmid pCMV.VEB (FIG. 11) expresses an antisense BEV polymerase mRNA under the control of the CMV-IE promoter sequence. To produce plasmid pCMV.VEB, the BEV polymerase sequence from pCR.BEV.2 (FIG. 7) was sub-cloned in the antisense orientation as a BglII-to-BamHI fragment into BglII/BamHI-digested pCMV.cass (FIG. 2).

Plasmid pCMV.BEVnt

Figure 12:
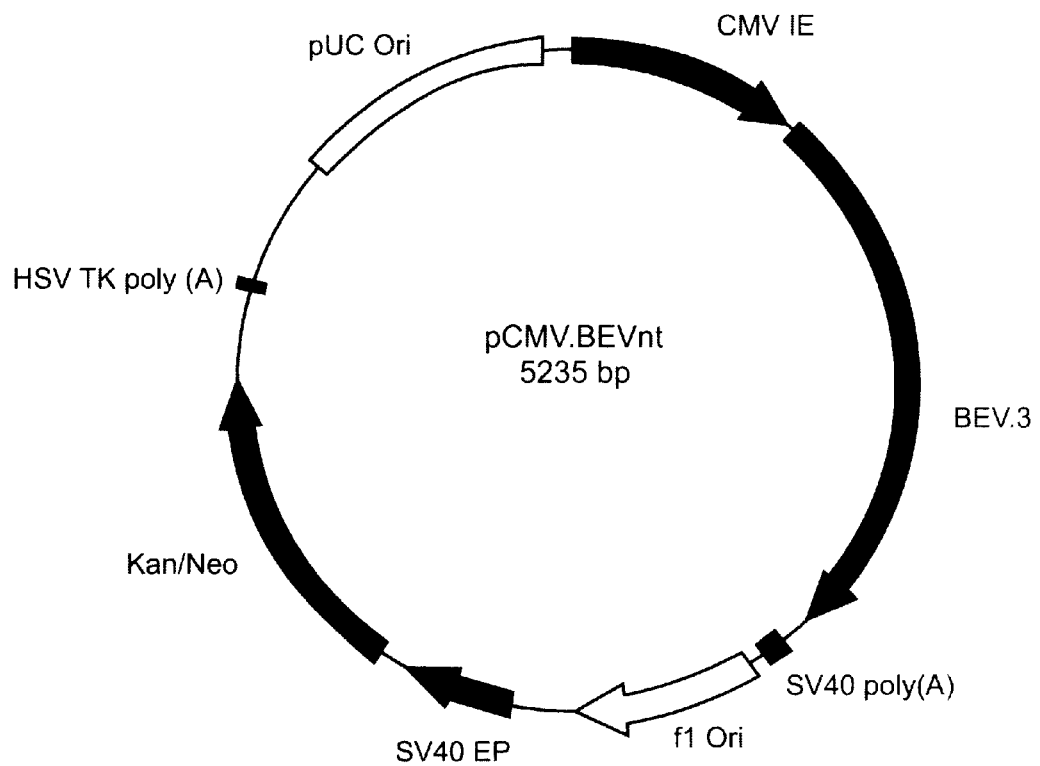
FIG. 12 is a copy of a diagrammatic representation of the plasmid pCMV.BEVnt

Plasmid pCMV.BEVnt (FIG. 12) expresses a non-translatable BEV polymerase structural gene in the sense orientation under the control of the CMV-IE promoter sequence. To produce pCMV.BEVnt, the BEV polymerase sequence from pCR.BEV.3 (FIG. 8) was sub-cloned in the sense orientation as a BglII-to-BamHI fragment into BglII/BamHI-digested pCMV.cass (FIG. 2).

Plasmid pCMV.BEVx2

Figure 13:
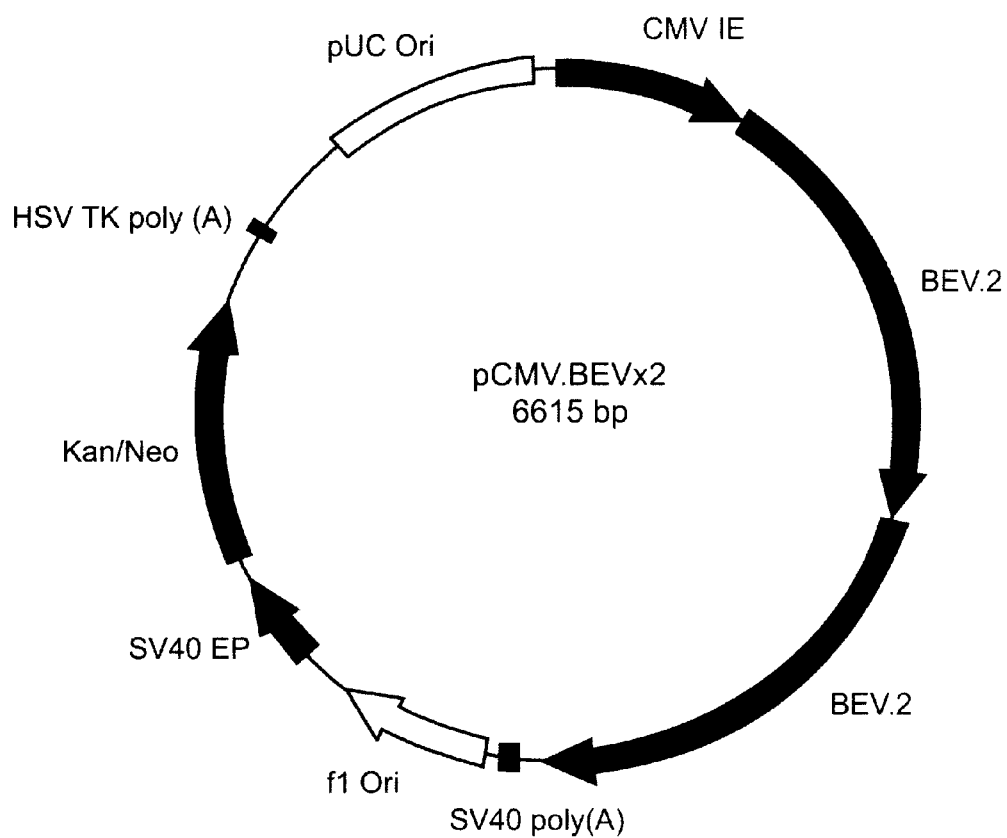
FIG. 13 is a copy of a diagrammatic representation of the plasmid pCMV.BEVx2.

Plasmid pCMV.BEVx2 (FIG. 13) comprises a direct repeat of a complete BEV polymerase open reading frame under the control of the CMV-IE promoter sequence. In eukaryotic cells at least, the open reading frame located nearer the CMV-IE promoter is translatable. To produce pCMV.BEVx2, the BEV polymerase structural gene from plasmid pCR.BEV.2 (FIG. 7) was sub-cloned in the sense orientation as a BglII-to-BamHI fragment into BamHI-digested pCMV.BEV.2 (FIG. 10), immediately downstream of the BEV polymerase structural gene already present therein.

Plasmid pCMV.BEV.VEB

Figure 14:
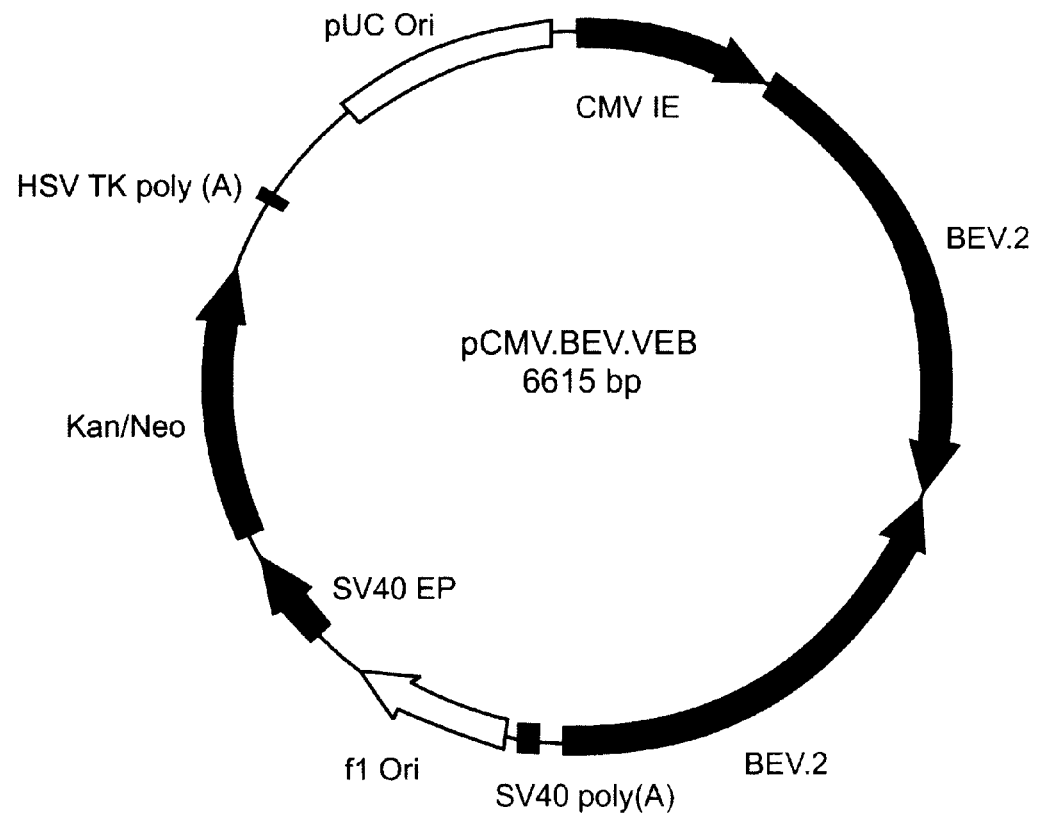

Plasmid pCMV.BEV.VEB (FIG. 14) comprises an inverted repeat or palindrome of a complete BEV polymerase open reading frame under the control of the CMV-IE promoter sequence. In eukaryotic cells at least, the open reading frame located nearer the CMV-IE promoter is translatable. To produce pCMV.BEV.VEB, the BEV polymerase structural gene from plasmid pCR.BEV.2 (FIG. 7) was sub-cloned in the antisense orientation as a BglII-to-BamHI fragment into BamHI-digested pCMV.BEV.2 (FIG. 10), immediately downstream of the BEV polymerase structural gene already present therein.

Plasmid pCMV.BEV.GFP.VEB

Figure 15:
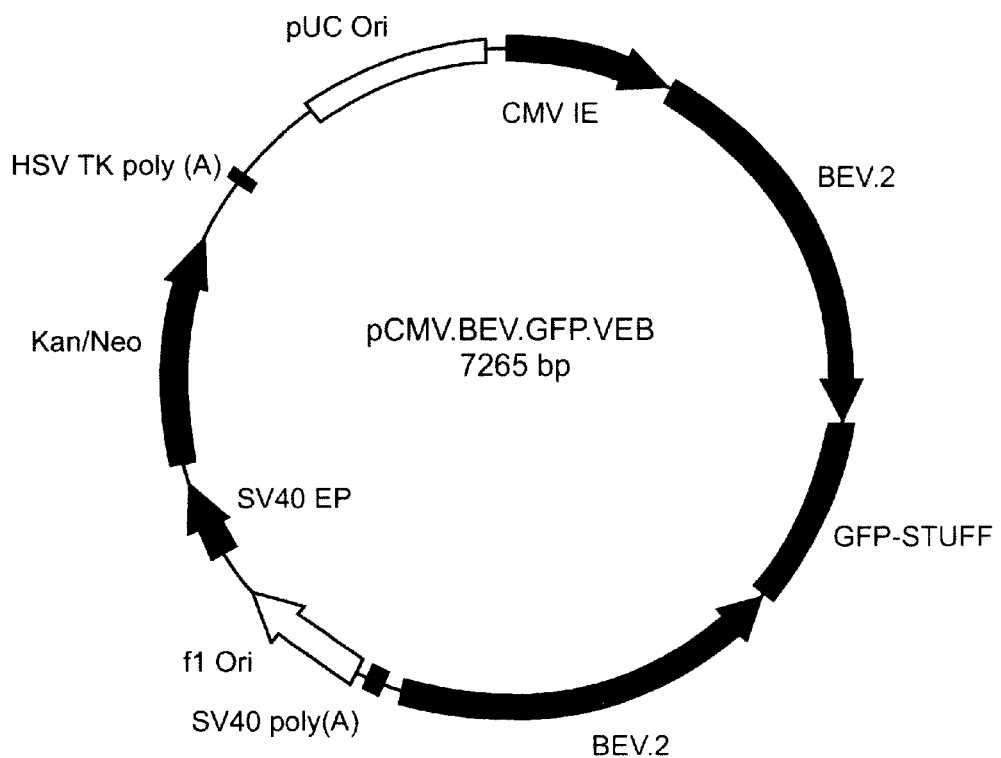
FIG. 15 is a copy of a diagrammatic representation of the plasmid pCMV.BEV.GFP.VEB.

Plasmid pCMV.BEV.GFP.VEB (FIG. 15) is similar to plasmid pCMV.BEV.VEB except that the BEV structural gene inverted repeat or palindrome is interrupted by the insertion of a GFP open reading frame (stuffer fragment) therein. To produce plasmid pCMV.BEV.GFP.VEB, the GFP stuffer fragment from pCR.Bgl-GFP-Bam (FIG. 3) was first sub-cloned in the sense orientation as a BglII-to-BamHI fragment into BamHI-digested pCMV.BEV.2 (FIG. 7) to produce an intermediate plasmid pCMV.BEV.GFP wherein the BEV polymerase-encoding and GFP-encoding sequences are contained within the same 5'-BglII-to-BamHI-3' fragment. The BEV polymerase structural gene from pCMV.BEV.2 (FIG. 7) was then cloned in the antisense orientation as a BglII-to-BamHI fragment into BamHI-digested pCMV.BEV.GFP. The BEV polymerase structural gene nearer the CMV-IE promoter sequence in plasmid pCMV.BEV.GFP.VEB is capable of being translated, at least in eukaryotic cells.

EXAMPLE 4

Synthetic Genes Comprising BEV Polymerase Structural Genes Operably Connected to Multiple Promoter Sequences Plasmid pCMV.BEV.SV40L-O Plasmid pCMV.BEV.SV40L-O (FIG. 16) comprises a translatable BEV polymerase structural gene derived from plasmid pCR.BEV.2 (FIG. 7) inserted in the sense orientation between the CMV-IE promoter and the SV40 late promoter sequences of plasmid pCMV.SV40L.cass (FIG. 5). To produce plasmid pCMV.BEV.SV40L-O, the BEV polymerase structural gene was sub-cloned as a BglII-to-BamHI fragment into BglII-digested pCMV.SV40L.cass DNA.

Plasmid pCMV.O.SV40L.BEV

Figure 17:
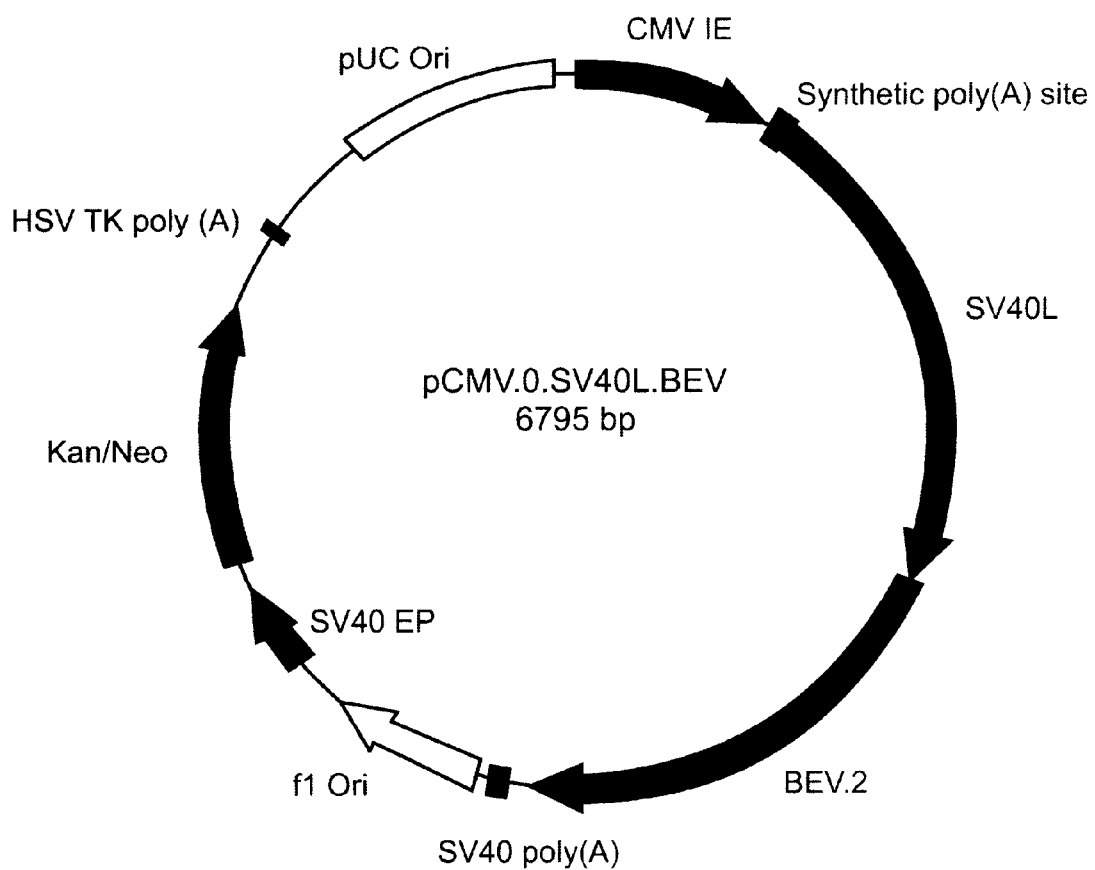
FIG. 17 is a copy of a diagrammatic representation of the plasmid pCMV.0.SV40L.BEV.

Plasmid pCMV.O.SV40L.BEV (FIG. 17) comprises a translatable BEV polymerase structural gene derived from plasmid pCR.BEV.2 (FIG. 7) cloned downstream of tandem CMV-IE promoter and SV40 late promoter sequences present in plasmid pCMV.SV40L.cass (FIG. 5). To produce plasmid pCMV.O.SV40L.BEV, the BEV polymerase structural gene was sub-cloned in the sense orientation as a BglII-to-BamHI fragment into BamHI-digested pCMV.SV40L.cass DNA.

Plasmid pCMV.O.SV40L.VEB

Figure 18:
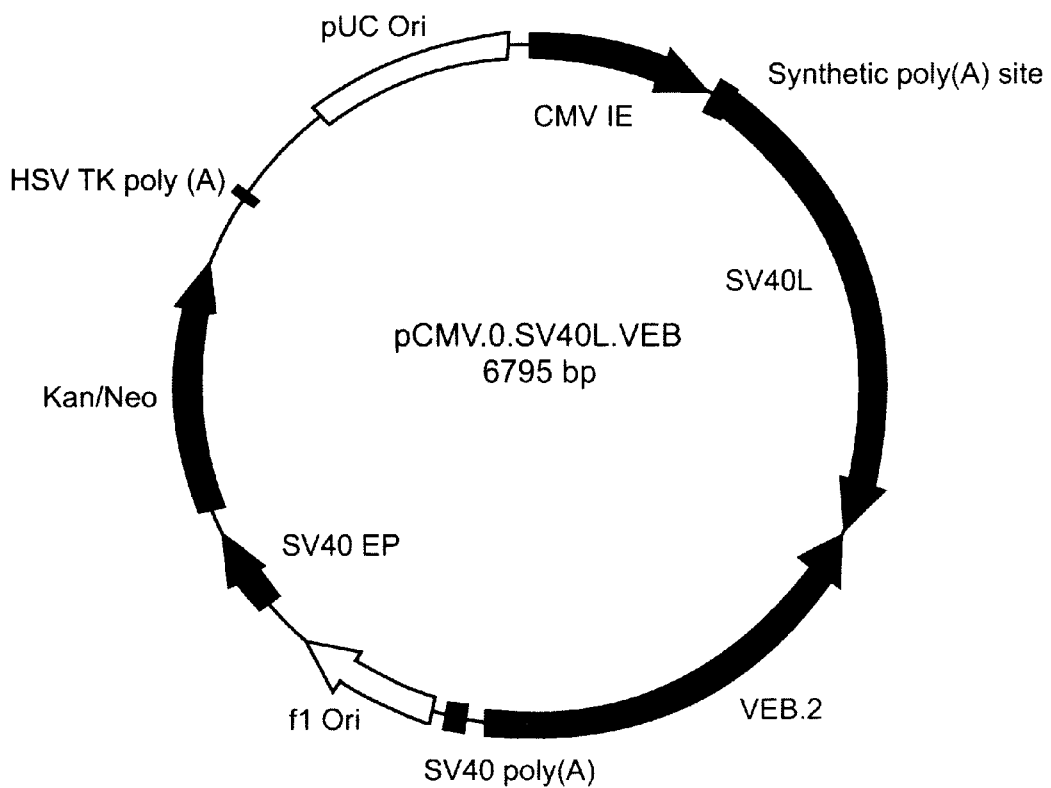
FIG. 18 is a copy of a diagrammatic representation of the plasmid pCMV.0.SV40L.VEB.

Plasmid pCMV.O.SV40L.VEB (FIG. 18) comprises an antisense BEV polymerase structural gene derived from plasmid pCR.BEV.2 (FIG. 7) cloned downstream of tandem CMV-IE promoter and SV40 late promoter sequences present in plasmid pCMV.SV40L.cass (FIG. 5). To produce plasmid pCMV.O.SV40L.VEB, the BEV polymerase structural gene was sub-cloned in the antisense orientation as a BglII-to-BamHI fragment into BamHI-digested pCMV.SV40L.cass DNA.

Plasmid pCMV.BEV.SV40L.BEV

Figure 16:
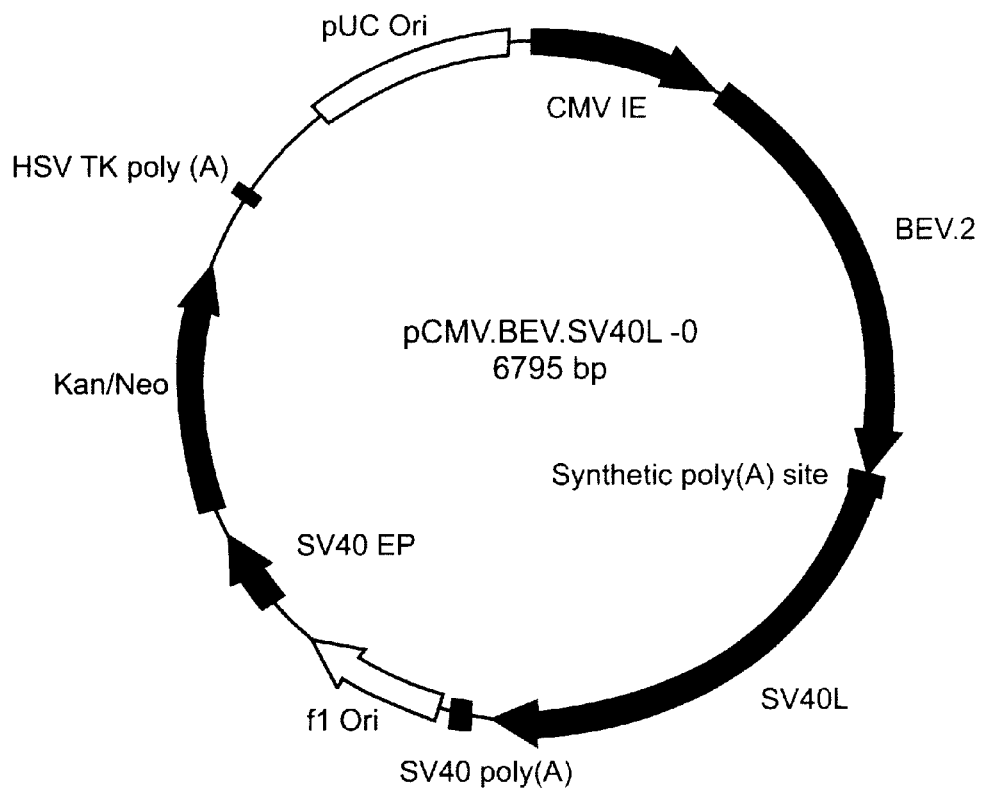
FIG. 16 is a copy of a diagrammatic representation of the plasmid pCMV.BEV.SV40L-0.
Figure 19:
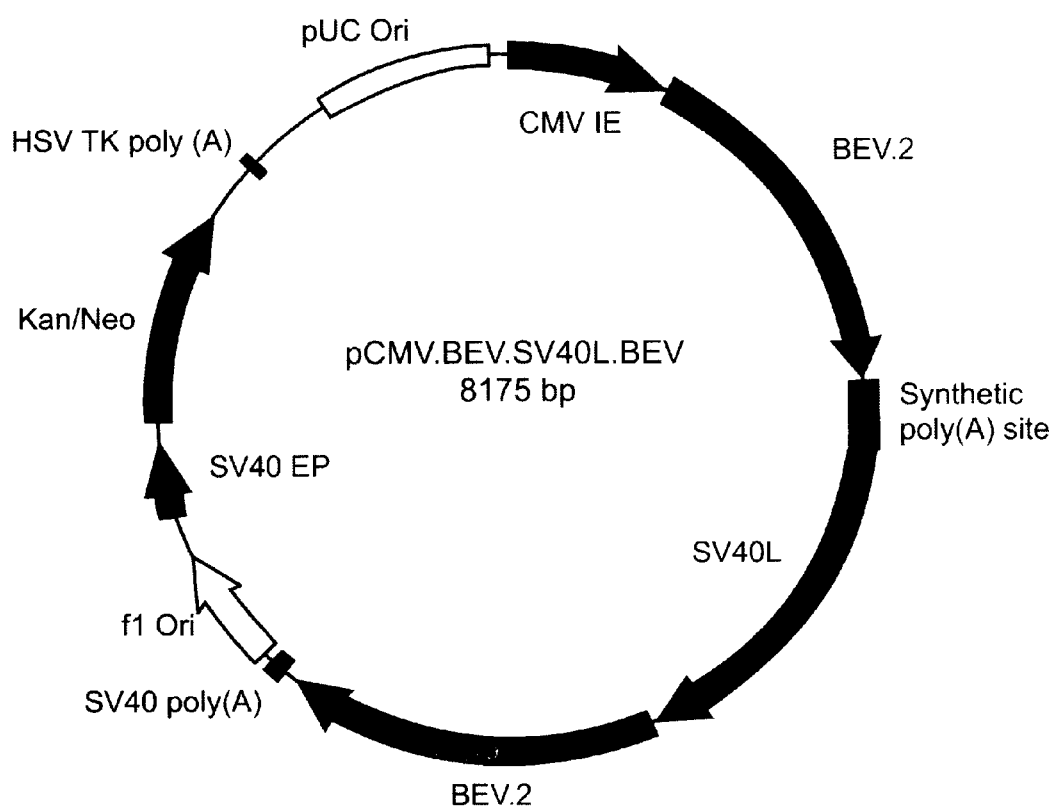
FIG. 19 is a copy of a diagrammatic representation of the plasmid pCMV.BEV.SV40L.BEV.

Plasmid pCMV.BEV.SV40L.BEV(FIG. 19) comprises a multiple structural gene unit comprising two BEV polymerase structural genes placed operably and separately under control of the CMV-IE promoter and SV40 late promoter sequences. To produce plasmid pCMV.BEV.SV40L.BEV, the translatable BEV polymerase structural gene present in pCR.BEV.2 (FIG. 7) was sub-cloned in the sense orientation as a BglII-to-BamHI fragment behind the SV40 late promoter sequence present in BamHI-digested pCMV.BEV.SV40L-O (FIG. 16).

Plasmid pCMV.BEV.SV40L.VEB

Figure 20:
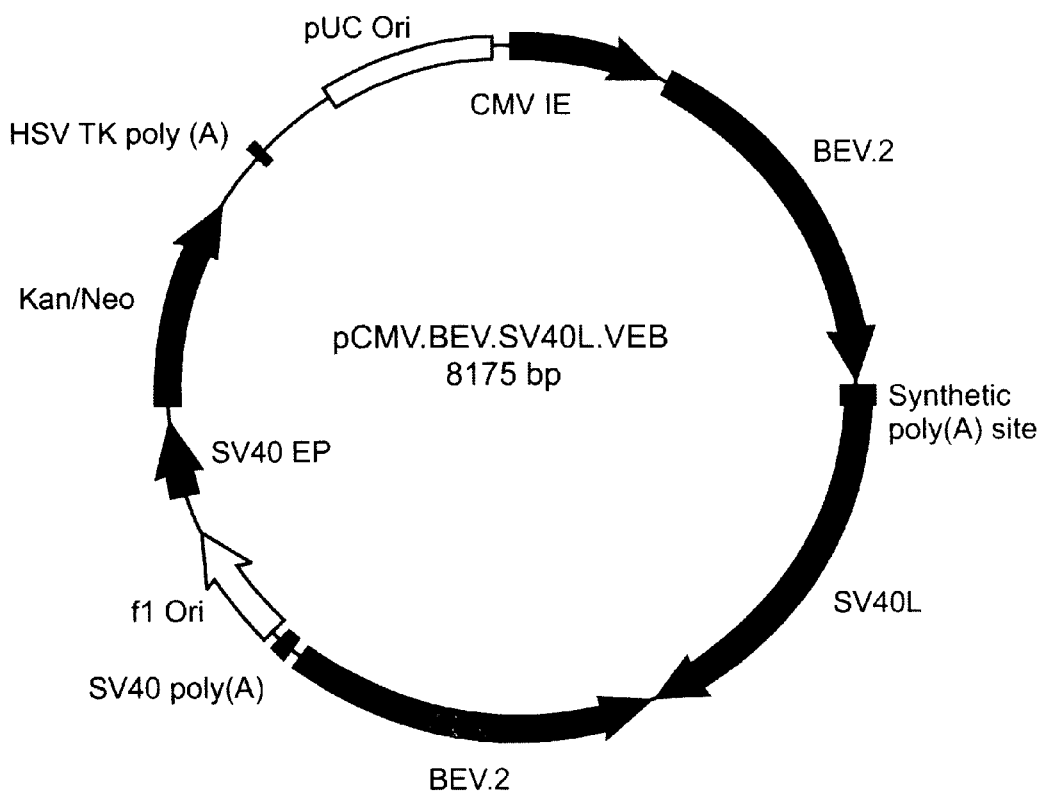
FIG. 20 is a copy of a diagrammatic representation of the plasmid PCMV.BEV.SV40L.VEB.

Plasmid pCMV.BEV.SV40L.VEB (FIG. 20) comprises a multiple structural gene unit comprising two BEV polymerase structural genes placed operably and separately under control of the CMV-IE promoter and SV40 late promoter sequences. To produce plasmid pCMV.BEV.SV40L.VEB, the translatable BEV polymerase structural gene present in pCR.BEV.2 (FIG. 7) was sub-cloned in the antisense orientation as a BglII-to-BamHI fragment behind the SV40 late promoter sequence present in BamHI-digested pCMV.BEV.SV40L-O(FIG. 16). In this plasmid, the BEV polymerase structural gene is expressed in the sense orientation under control of the CMV-IE promoter to produce a translatable mRNA, whilst the BEV polymerase structural gene is also expressed under control of the SV40 promoter to produce an antisense mRNA species.

Plasmid pCMV.SV40LR.cass

Plasmid pCMV.SV40LR.cass (FIG. 21) comprises the SV40 late promoter sequence derived from plasmid pCR.SV40L (FIG. 4), sub-cloned as a SalI fragment into the SalI site of the plasmid pCMV.cass (FIG. 2), such that the CMV-IE or the SV40 late promoter may drive transcription of a structural gene or a multiple structural gene unit, in the sense or antisense orientation, as desired. A multiple cloning site is positioned between the opposing CMV-IE and SV40 late promoter sequences in this plasmid to facilitate the introduction of a structural gene sequence. In order for expression of a structural gene sequence to occur from this plasmid, it must be introduced with its own transcription termination sequence located at the 3' end, because there are no transcription termination sequences located between the opposing CMV-IE and SV40 late promoter sequences in this plasmid. Preferably, the structural gene sequence or multiple structural gene unit which is to be introduced into pCMV.SV40LR.cass will comprise both a 5' and a 3' polyadenylation signal as follows:

(i) where the structural gene sequence or multiple structural gene unit is to be expressed in the sense orientation from the CMV IE promoter sequence and/or in the antisense orientation from the SV40 late promoter, the 5' polyadenylation signal will be in the antisense orientation and the 3' polyadenylation signal will be in the sense orientation; and (ii) where the structural gene sequence or multiple structural gene unit is to be expressed in the antisense orientation from the CMV IE promoter sequence and/or in the sense orientation from the SV40 late promoter, the 5' polyadenylation signal will be in the sense orientation and the 3' polyadenylation signal will be in the antisense orientation.

Figure 21:
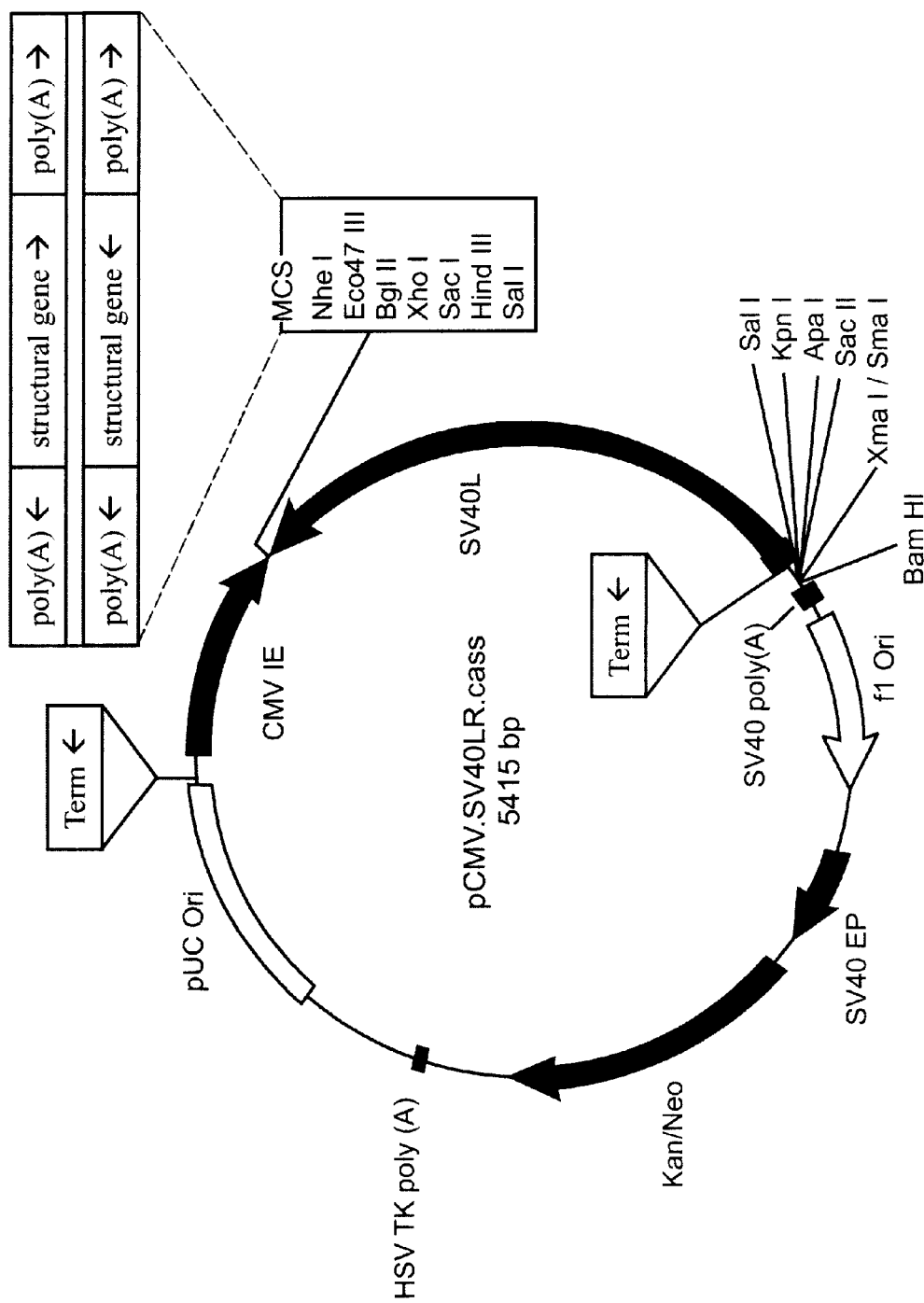
FIG. 21 is a copy of a diagrammatic representation of the plasmid pCMVSV40LR.cass.

Alternatively or in addition, suitably-oriented terminator sequences may be placed at the 5'-end of the CMV and SV40L promoters, as shown in FIG. 21.

Alternatively, plasmid pCMV.SV40LR.cass is further modified to produce a derivative plasmid which comprises two polyadenylation signals located between the CMV IE and SV40 late promoter sequences, in appropriate orientations to facilitate expression of any structural gene located therebetween in the sense or antisense orientation from either the CMV IE promoter or the SV40 promoter sequence. The present invention clearly encompasses such derivatives.

Plasmid pCMV.BEV.SV40LR

Figure 22:
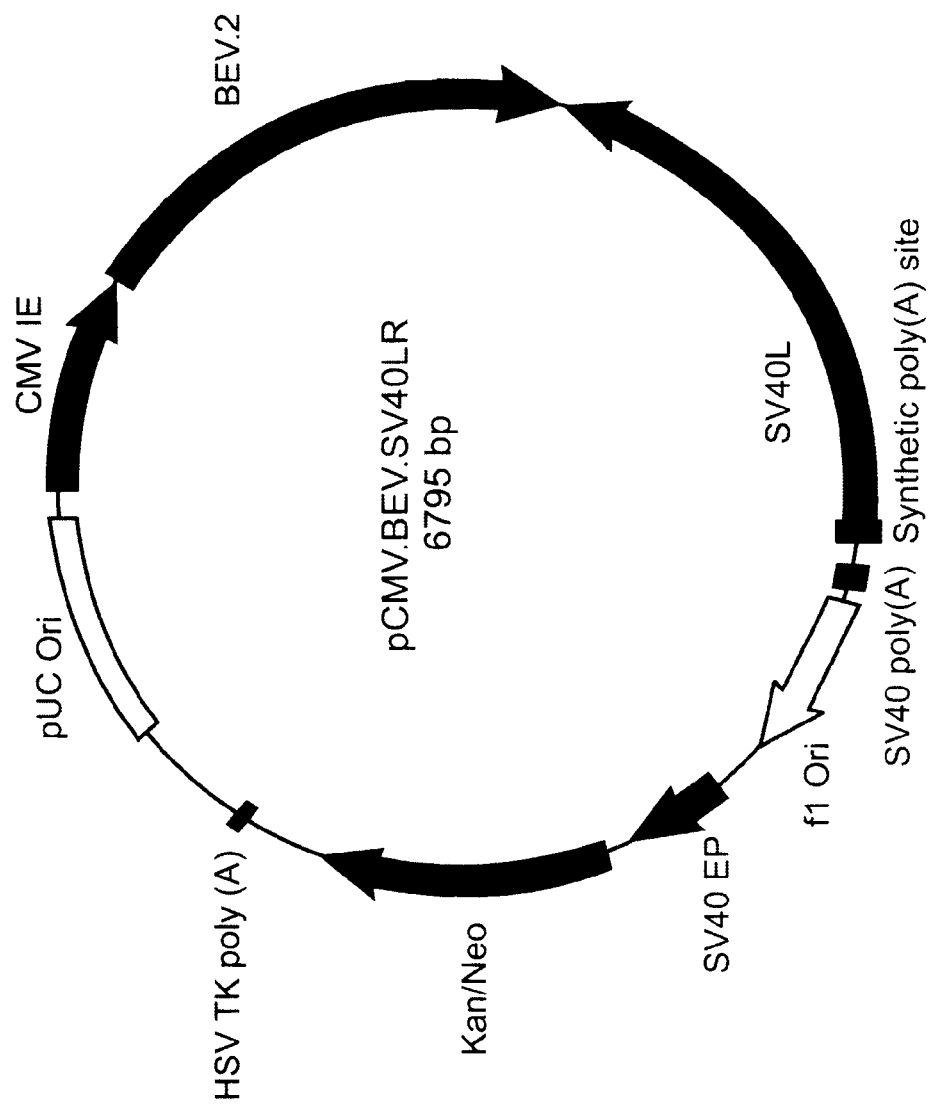
FIG. 22 is a copy of a diagrammatic representation of the plasmid pCMV.BEV.SV40LR.

Plasmid pCMV.BEV.SV40LR (FIG. 22) comprises a structural gene comprising the entire BEV polymerase open reading frame placed operably and separately under control of opposing CMV-IE promoter and SV40 late promoter sequences, thereby potentially producing BEV polymerase transcripts at least from both strands of the full-length BEV polymerase structural gene. To produce plasmid pCMV.BEV.SV40LR, the translatable BEV polymerase structural gene present in pCR.BEV.2 (FIG. 7) was sub-cloned, as a BglII-to-BamHI fragment, into the unique BglII site of plasmid pCMV.SV40LR.cass (FIG. 21), such that the BEV open reading frame is present in the sense orientation relative to the CMV-IE promoter sequence.

Those skilled in the art will recognise that it is possible to generate a plasmid wherein the BEV polymerase fragment from pCR.BEV.2 is inserted in the antisense orientation, relative to the CMV IE promoter sequence, using this cloning strategy. The present invention further encompasses such a genetic construct.

EXAMPLE 5

Synthetic Genes and Genetic Constructs Comprising the Tyrosinase Open Reading Frame Isolation of the Tyrosinase Open Reading Frame The tyrosinase structural gene is isolated by polymerase chain reaction, from mRNA derived from murine cells, using the following oligonucleotide primers under standard polymerase chain reaction conditions:

Tyr 5' (forward primer; SEQ ID NO:9):
  5'-CCCGGGGCTTAGTGTAAAACAGGCTGAGAG-3'; and Tyr 3' (reverse primer; SEQ ID NO:10):
  5'-CCCGGGCAAATCCCAGTCATTTCTTAGAAAC-3'.

Nucleotide residues 1 to 6 in each primer represent a SmaI cloning site. Nucleotides 7 to 30 of primer Tyr 5' correspond to the 5'-end of the murine tyrosinase cDNA sequence disclosed in GenBank Accession No. M20234 (Kwon et al, 1988). Nucleotides 7 to 31 of primer Tyr 3' correspond to the complement of the nucleotide sequence of the 3'-end of the murine tyrosinase cDNA sequence.

Plasmid pCR.tyr

Plasmid pCR.tyr is produced by sub-cloning the amplified tyrosinase structural gene into plasmid pCR2.1 (Example 1), substantially according to the manufacturer's protocol. Plasmid pCR.tyr can be used as a base plasmid to produce a range of genetic constructs designed to express the tyrosinase structural gene or a multiple structural gene unit comprising same, under the control of one or more promoter sequences.

Plasmid pCMV.TYR

Figure 23:
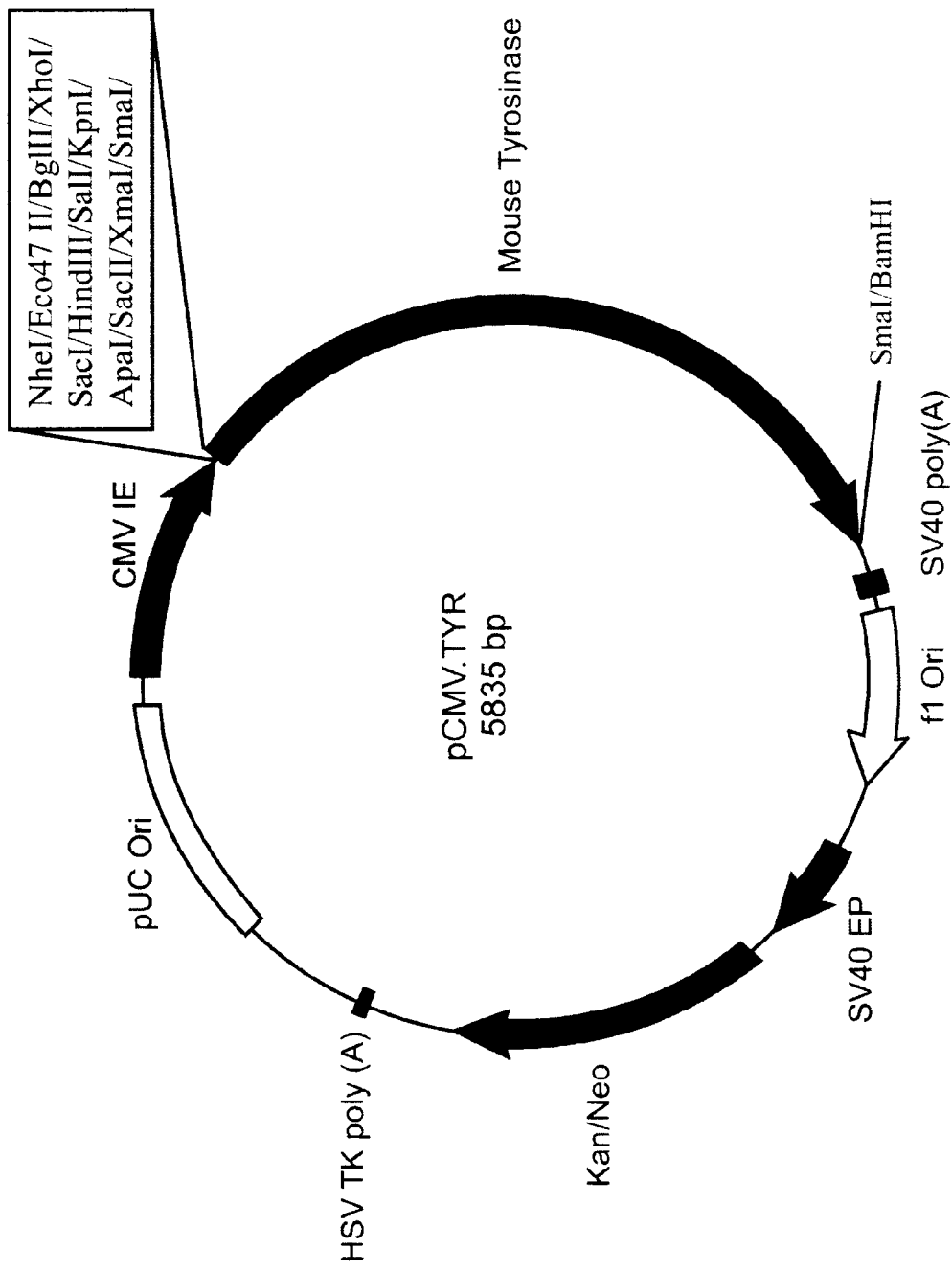
FIG. 23 is a copy of a diagrammatic representation of the plasmid pCMV.TYR.

Plasmid pCMV.TYR (FIG. 23) comprises the complete mouse tyrosinase cDNA sequence placed operably in connection, in the sense orientation, with the CMV-IE promoter sequence and upstream of the SV40 polyadenylation sequence. To produce pCMV.TYR, the fill-length mouse tyrosinase cDNA sequence was excised from plasmid pCRtyr by digestion with SmaI and then ligated, into the SmaI cloning site of pCMV.cass (FIG. 2). Clones possessing the tyrosinase structural gene in the sense orientation relative to the CMV-IE promoter were then selected.

Plasmid pCMV.TYRLIB

Figure 24:
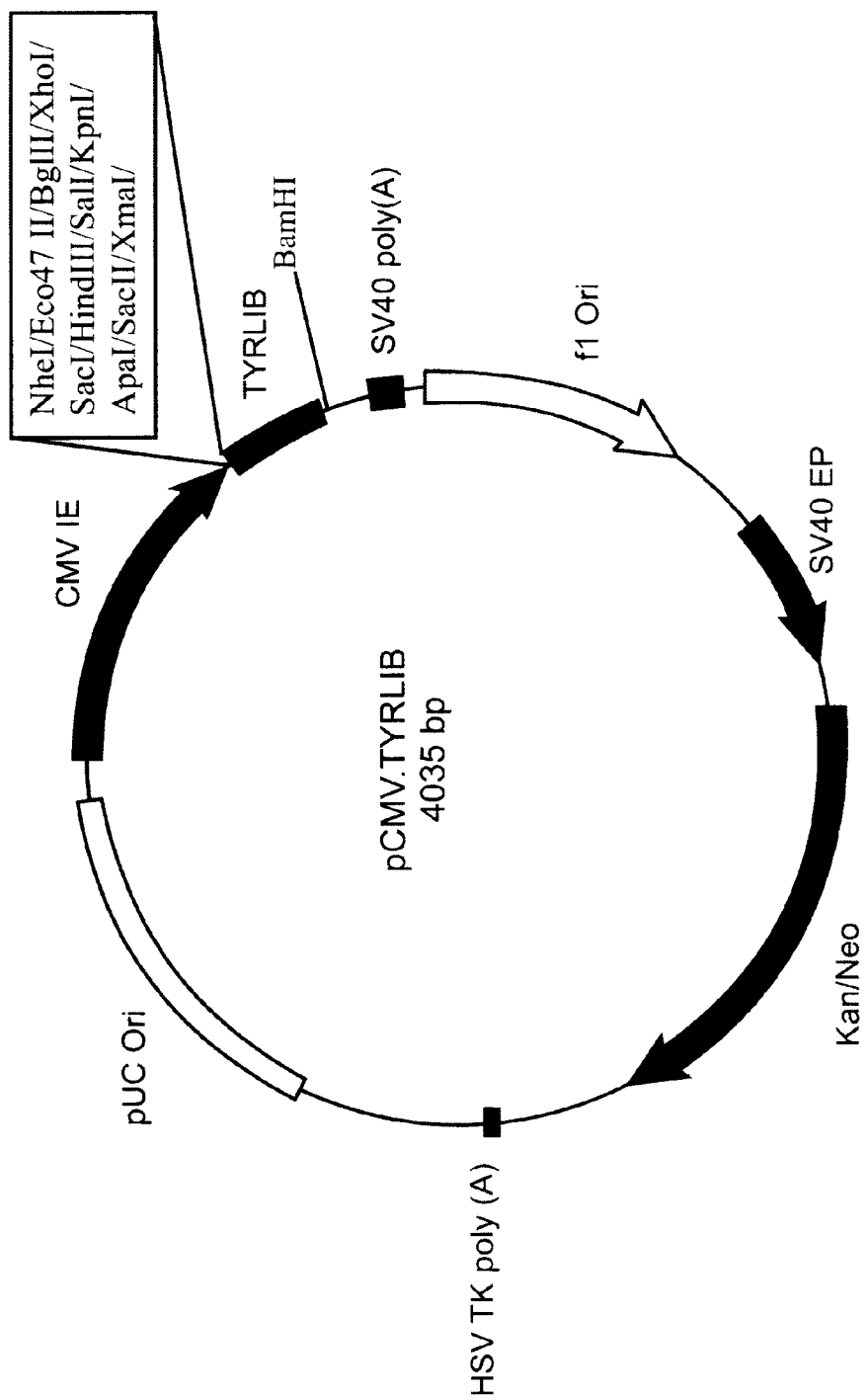
FIG. 24 is a copy of a diagrammatic representation of the plasmid PCMV.TYRLIB.

Plasmid pCMV.TYRLIB (FIG. 24) comprises a structural gene or multiple structural gene unit which comprises one or more tyrosinase gene fragments of 100 to 200 base pairs in length each, placed operably in connection with the CMV-IE promoter sequence and upstream of the SV40 polyadenylation signal. To produce pCMV.TYRLIB, blunt-ended fragments of the tyrosinase gene are ligated into SmaI-digested, dephosphorylated plasmid pCMV.cass DNA (FIG. 2). The tyrosinase gene fragments are produced, for example, by sonication or mechanical shearing and end-repair using T4 DNA polymerase. Accordingly, the structural gene insert in plasmid pCMV.TYRLIB is variable and an representative library of pCMV.TYRLIB plasmids, covering the complete tyrosinase gene sequence, may be produced using such procedures. The present invention clearly encompasses such representative libraries. Those skilled in the art will recognise that such procedures are also useful for structural genes other than tyrosinase and, as a consequence, the present invention clearly extends to synthetic genes and genetic constructs wherein the structural gene present in pCMV-.TYRLIB is a structural gene other than a tyrosinase gene fragment.

EXAMPLE 6

Synthetic Genes and Genetic Constructs Comprising the lacI Open Reading Frame

Plasmid pCMV.Lac

Figure 25:
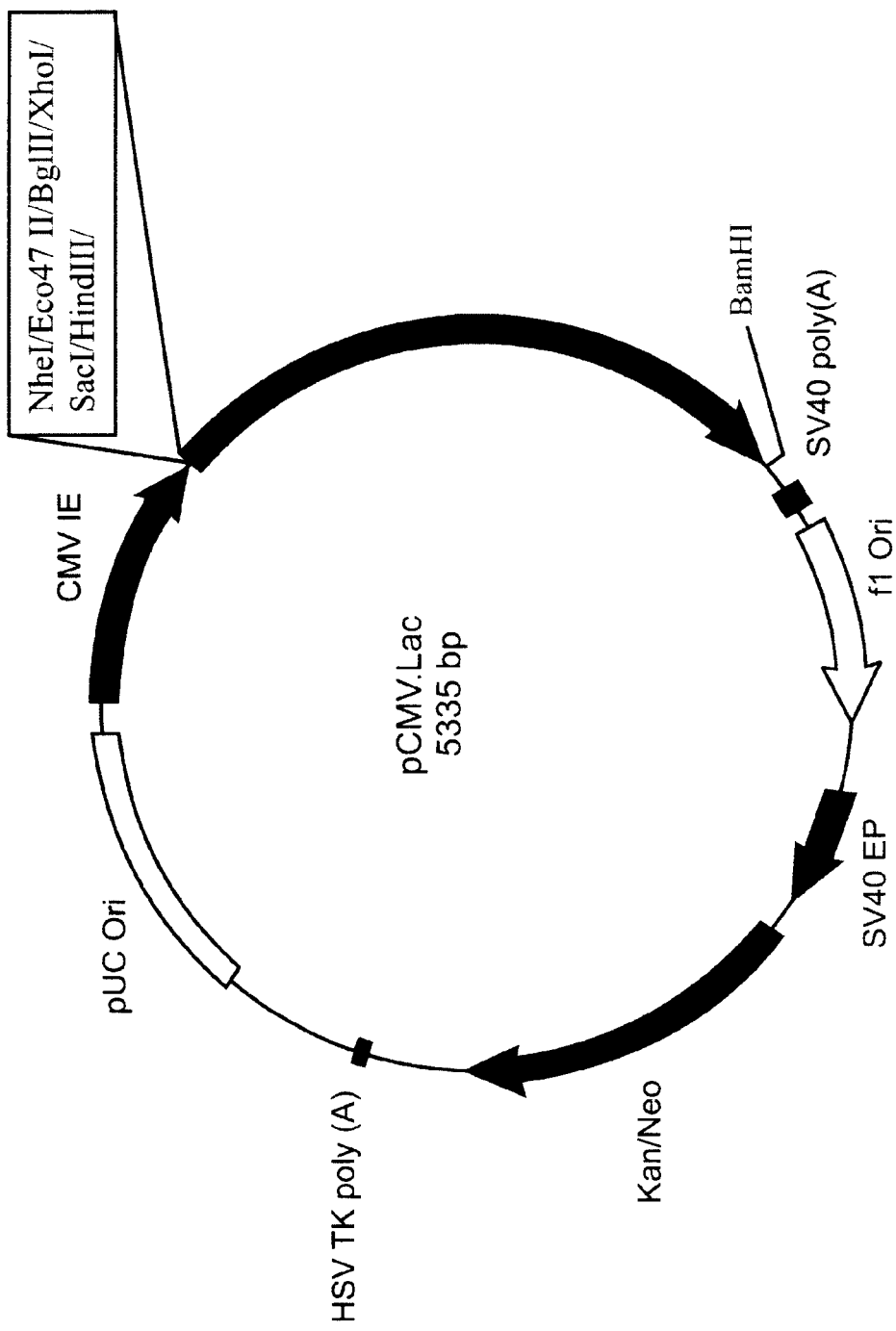
FIG. 25 is a copy of a diagrammatic representation of the plasmid pCMV.Lac.

Plasmid pCMV.Lac (FIG. 25) contains a CMV IE promoter driving expression of the lac repressor protein encoded by the *Escherichia coli* lacI gene. Accordingly, the open reading frame of the LacI gene is cloned in the sense orientation with respect to the CMV IE promoter sequence in this plasmid. This construct also contains the selectable marker for neomycin resistance.

To produce plasmid pCMV.Lac, the lacI gene was excised from plasmid pCMV.LacI (Stratagene) by digestion with HindIII and BsaBI and then ligated, in the sense orientation, into the multiple cloning site (MCS) of plasmid pCMV.cass (FIG. 2) which had been digested with HindIII and SmaI.

Plasmid pCMVLacI.OPRSV1.cass

Plasmid pCMVLacI.OPRSV1.cass (FIG. 26) is a dual expression construct in which the CMV-IE promoter drives expression of the LacI structural gene to produce the lac repressor protein and the OPRSVI promoter drives the expression of a second structural gene or multiple structural gene unit placed operably under control of lac repressor protein.

To produce plasmid pCMVLac.OPRSV1.cass, a DNA fragment comprising the OPRSVI promoter, SV40 intron, lac operator sequence, multiple cloning site (MCS) and TK poly(A) sequence was excised from plasmid pOPRSVI/MCS (Stratagene), by digestion with SnaB1 and AseI restriction enzymes, then end-filled using PfuI polymerase and ligated into the end-filled BglII cloning site of plasmid pCMVLacI (Stratagene).

EXAMPLE 7

Synthetic Genes and Genetic Constructs Comprising the lacI and Green Fluorescent Protein (GFP)Open Reading Frames

Plasmid pCMVLacI.OPRSV1.GFP.cass

Plasmid pCMVLacI.OPRSVI.GFP.cass (FIG. 27) is designed such that a structural gene or multiple structural gene unit can be fused to the 3' untranslated region of the lacI gene, by cloning directly into the unique BsaB1 cloning site which is located after the lacI stop codon and before an SV40 polyadenylation signal. Alternatively, the BSAB1 site may be modified to facilitate cloning, for example by the addition of linkers or adaptors. This construct also contains the antibiotic selectable marker for hygromycin resistance.

Figure 26:
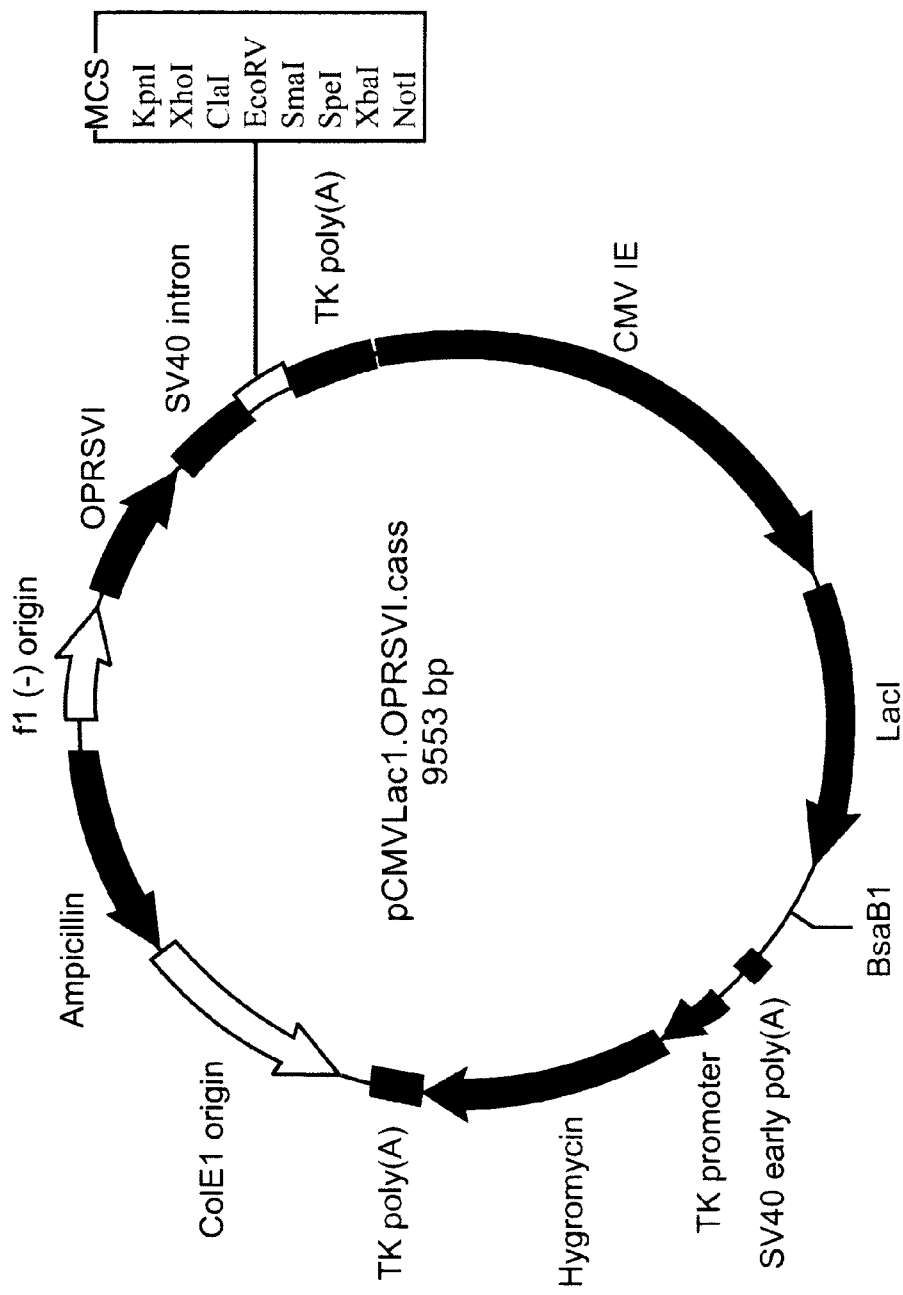
FIG. 26 is a copy of a diagrammatic representation of the plasmid pCMVLacI.OPRSV1.cass.

To produce plasmid pCMVLacI.OPRSVI.GFP.cass, the enhanced GFP coding sequence was excised from plasmid PEGFP-N1 MCS (FIG. 1) by digestion with XhoI and NotI and the DNA fragment thus produced was ligated into the XhoI and NotI cloning sites of the multiple cloning site present in plasmid pCMVLacI.OPRSVI.cass (FIG. 26).

EXAMPLE 8

Synthetic Genes and Genetic Constructs Comprising the lacI and Green Fluorescent Protein (GFP) and Tyrosinase Open Reading Frames

Plasmid pCMVLacI.TYR.OPRSV1.GFP

Figure 28:
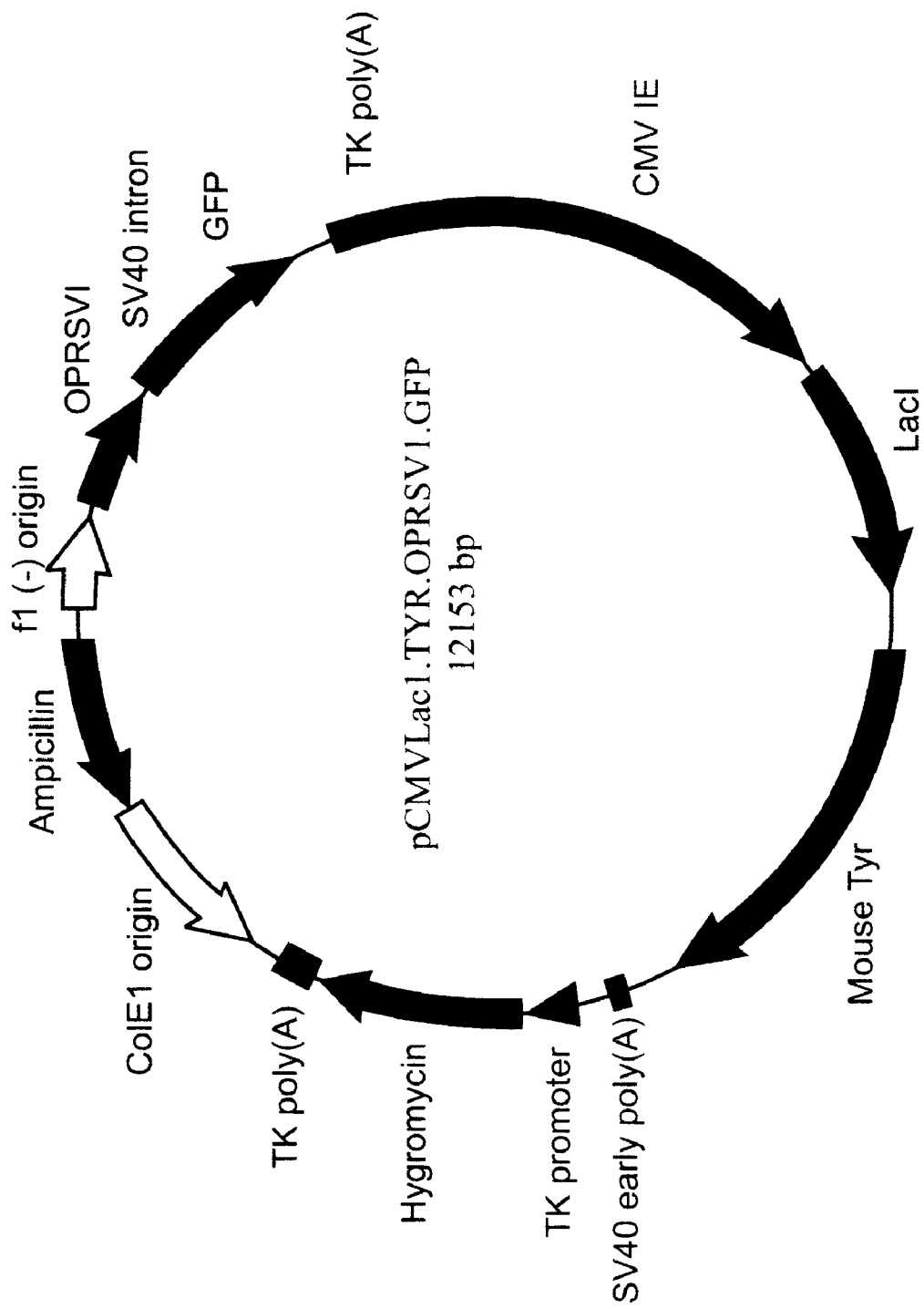
FIG. 28 is a copy of a diagrammatic representation of the plasmid pCMVLacI.TYR.OPRSV1.GFP.

Plasmid pCMVLacI.TYR.OPRSV/1.GFP (FIG. 28) is a dual construct in which the CMV IE promoter drives expression of the lacI gene and the mRNA of the mouse tyrosinase cDNA or a fragment thereof, whilst the OPRSVI promoter drives expression of GFP operably under control of the lacI gene. The construct is designed such that the mouse tyrosinase gene is fused to the 3' untranslated region of the lacI gene via a unique BsaB1cloning site. This cloning site is located after the stop codon of the lad coding sequence, but before the SV40 polyadenylation signal. The construct also contains the hygromycin-resistance gene as a selection marker.

Figure 27:
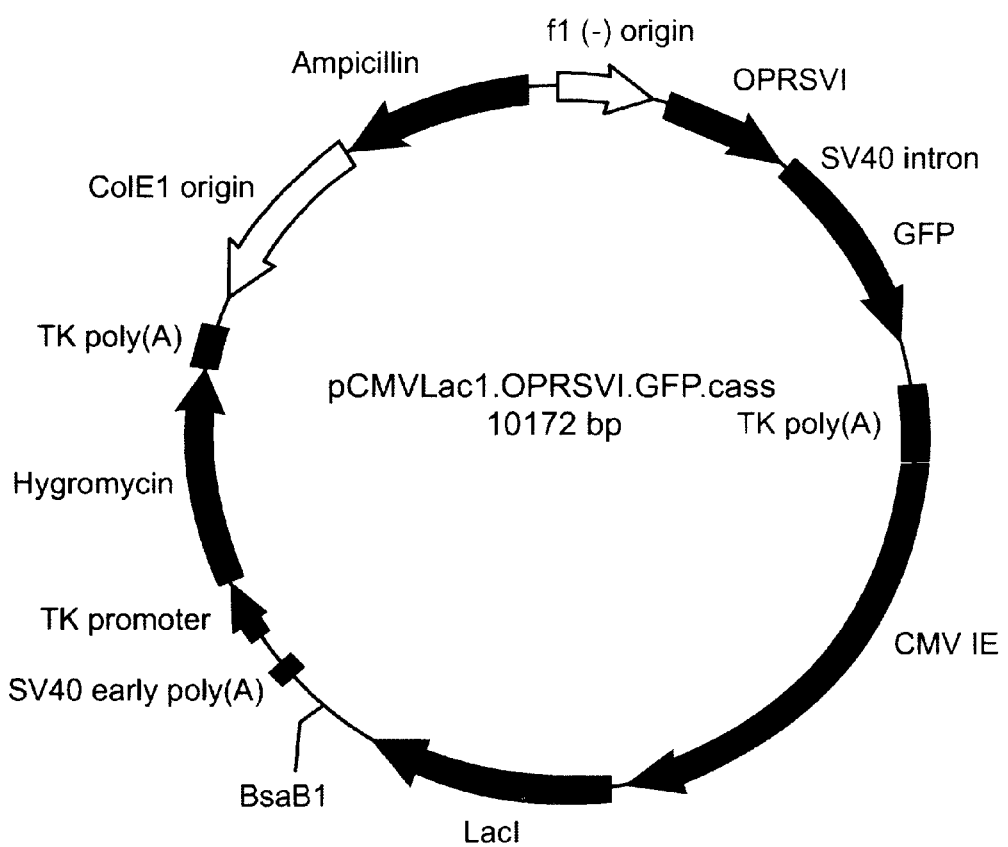
FIG. 27 is a copy of a diagrammatic representation of the plasmid pCMVLacI.OPRSV1.GPP.cass.

To produce plasmid pCMVLacI.TYR.OPRSV1.GFP, the complete tyrosinase gene present in plasmid pCR.tyr (Stratagene; Example 1) is isolated from host cells, digested with SmaI and ligated into BsaB1-digested and dephosphorylated plasmid pCMVLacI.OPRSVI.GFP.cass DNA (FIG. 27).

Equivalents

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

References

1. Ausubel, F. M. et al.(1987) In: Current Protocols in Molecular Biology, Wiley Interscience (ISBN 047140338).
2. Chalfie, M. et al (1994) *Science* 263: 802–805.
3. Cormack, B. et al (1996) *Gene* 173: 33–38.
4. Inouye, S. and Tsuji, F. I. (1994) *FEBS Leas.* 341: 277–280.
5. Kwon, B. S. et al. (1988) *Biochem. Biophys. Res. Comm.* 153:1301–1309.
6. Prasher, D. C. et al. (1992) *Gene* 111: 229–233.

What is claimed is:

1. An isolated genetic construct which is capable of delaying, repressing or otherwise reducing the expression of a target gene in an animal cell which is transfected with said genetic construct, wherein said genetic construct comprises at least two copies of a structural gene sequence, wherein said structural gene sequence comprises a nucleotide sequence which is substantially identical to at least a region of said target gene, and wherein said at least two copies of said structural gene sequence are placed operably under the control of a single promoter sequence which is operable in said cell, wherein at least one copy of said structural gene sequence is placed operably in the sense orientation under the control of said promoter sequence.

2. An isolated genetic construct which is capable of delaying, repressing or otherwise reducing the expression of a target gene in an animal cell which is transfected with said genetic construct, wherein said genetic construct comprises at least two copies of a structural gene sequence wherein each copy of said structural gene sequence is separately placed under the control of a promoter which is operable in said cell, and wherein said structural gene sequence comprises a nucleotide sequence which is substantially identical to at least a region of said target gene, wherein at least one copy of said structural gene sequence is placed operably in the sense orientation under the control of an individual promoter sequence.

3. An isolated genetic construct which is capable of delaying, repressing or otherwise reducing the expression of a target gene in an animal cell which is transfected with said genetic construct, wherein said genetic construct comprises at least two copies of a structural gene sequence, wherein said structural gene sequence comprises a nucleotide sequence which is substantially identical to at least a region of said target gene, and wherein said at least two copies of said structural gene sequence are placed operably under the control of a single promoter sequence which is operable in said cell, wherein at least one copy of said structural gene sequence is placed operably in the sense orientation under the control of said promoter sequence and wherein at least one other copy of said structural gene sequence is placed operably in the antisense orientation under the control of said promoter sequence.

4. An isolated genetic construct which is capable of delaying, repressing or otherwise reducing the expression of a target gene in an animal cell which is transfected with said genetic construct, wherein said genetic construct comprises at least two copies of a structural gene sequence and each copy of said structural gene sequence is separately placed under the control of a promoter which is operable in said cell, and wherein said structural gene sequence comprises a nucleotide sequence which is substantially identical to at least a region of said target gene, wherein at least one copy of said structural gene sequence is placed operably in the sense orientation under the control of an individual promoter sequence, and wherein at least one other copy of said structural gene sequence is placed operably in the antisense orientation under the control of another individual promoter sequence.

5. An isolated genetic construct which is capable of delaying, repressing or otherwise reducing the expression of a target gene in an animal cell which is transfected with said genetic construct, wherein said genetic construct comprises at least two copies of a structural gene sequence, wherein said structural gene sequence comprises a nucleotide sequence which is substantially identical to at least a region of said target gene, and wherein said at least two copies of said structural gene sequence are placed operably under the control of a single promoter sequence which is operable in said cell, wherein at least one copy of said structural gene sequence is placed operably in the sense orientation under the control of said promoter sequence, wherein at least one other copy of said structural gene sequence is placed operably in the antisense orientation under the control of said promoter sequence, and wherein said at least one copy of said structural gene sequence that is placed in the sense orientation relative to said promoter and said at least one copy of said structural gene sequence that is placed in the antisense orientation relative to said promoter are spaced from each other by a nucleic acid stuffer fragment.

6. An animal cell comprising the genetic construct of any one of claims 1–2 or 3–5.

7. A method of delaying or repressing the expression of a target gene in an animal cell, comprising transfecting said animal cell with a genetic construct, wherein said genetic construct comprises at least two copies of a structural gene sequence, wherein said structural gene sequence comprises a nucleotide sequence which is substantially identical to at least a region of said target gene, and wherein said at least two copies of said structural gene sequence are placed operably under the control of a single promoter sequence which is operable in said cell, wherein at least one copy of said structural gene sequence is placed operably in the sense orientation under the control of said promoter sequence.

8. The method according to claim 7, wherein at least one other copy of said structural gene sequence is placed operably in the antisense orientation under the control of said promoter sequence.

9. The method according to claim 8, wherein said copy of said structural gene sequence that is placed in the sense orientation relative to said promoter and said copy of said structural gene sequence that is placed in the antisense orientation relative to said promoter are spaced from each other by a nucleic acid stuffer fragment.

10. A method of delaying or repressing the expression of a target gene in an animal cell, comprising expressing in said animal cell a genetic construct, wherein said genetic construct comprises at least two copies of a structural gene sequence, wherein each copy of said structural gene sequence is separately placed under the control of a promoter which is operable in said cell, and wherein said structural gene sequence comprises a nucleotide sequence which is substantially identical to at least a region of said target gene, wherein at least one copy of said structural gene sequence is placed operably in the sense orientation under the control of an individual promoter sequence.

11. The isolated genetic construct according to any one of claims 1, 2 or 3–5 wherein said region of the target gene is 20 to 30 nucleotides long.

12. The method according to any one of claims 7–9 or 10 wherein said region of the target gene is 20 to 30 nucleotides long.

13. The isolated genetic construct according to any one of claims 1, 2 or 3–5, comprising two copies of said structural gene sequence.

14. The isolated genetic construct according to any one of claims 1, 2 or 3–5 wherein said region of the target gene is at least 30 nucleotides long.

15. The isolated genetic construct according to any one of claims 1, 2 or 3–5 wherein said structural gene sequence comprises a nucleotide sequence that is identical to said region of said target gene.

16. The method according to any one of claims 7–9 or 10, wherein said genetic construct comprises two copies of said structural gene sequence.

17. The method according to any one of claims 7–9 or 10, wherein said region of the target gene is at least 30 nucleotides long.

18. The method according to any one of claims 7–9 or 10, wherein said structural gene sequence comprises a nucleotide sequence that is identical to said region of said target gene.

19. An animal cell comprising the genetic construct according to claim 11.

20. An animal cell comprising the genetic construct according to claim 13.

21. An animal cell comprising the genetic construct according to claim 14.

22. An animal cell comprising the genetic construct according to claim 15.

* * * * *

UNITED STATES PATENT AND TRADEMARK OFFICE
CERTIFICATE OF CORRECTION

| | | |
|---|---|---|
| PATENT NO. | : 6,573,099 C1 | Page 1 of 1 |
| APPLICATION NO. | : 90/008096 | |
| DATED | : March 8, 2011 | |
| INVENTOR(S) | : Michael Wayne Graham, Peter Michael Waterhouse and Robert Norman Rice | |

It is certified that error appears in the above-identified patent and that said Letters Patent is hereby corrected as shown below:

Title page, item [75] should read as follows:

--Michael Wayne Graham, Peter Michael Waterhouse, and Robert Norman Rice--

Signed and Sealed this
Fourteenth Day of February, 2012

David J. Kappos
*Director of the United States Patent and Trademark Office*

(12) EX PARTE REEXAMINATION CERTIFICATE (8071st)
United States Patent
Graham

(10) Number: US 6,573,099 C1
(45) Certificate Issued: Mar. 8, 2011

(54) SYNTHETIC GENES AND GENETIC CONSTRUCTS COMPRISING SAME I

(75) Inventor: Michael Wayne Graham, St. Lucia (AU)

(73) Assignee: Commonwealth Scientific and Industrial Research Organization, Campbell, Australian Capital Territory (AU)

Reexamination Request:
No. 90/007,247, Oct. 4, 2004
No. 90/008,096, May 18, 2006

Reexamination Certificate for:
Patent No.: 6,573,099
Issued: Jun. 3, 2003
Appl. No.: 09/100,812
Filed: Jun. 19, 1998

(30) Foreign Application Priority Data

Mar. 20, 1998 (AU) .............................................. PP2492

(51) Int. Cl.
C12N 15/67 (2006.01)
C12N 15/63 (2006.01)
C12N 15/69 (2006.01)
C12N 15/82 (2006.01)
C12N 9/50 (2006.01)
C12N 9/10 (2006.01)
C12N 9/12 (2006.01)

(52) U.S. Cl. ..................... 435/455; 435/320.1; 435/325; 424/93.21; 424/93.2; 514/44 R; 536/24.5

(58) Field of Classification Search ........................ None
See application file for complete search history.

(56) References Cited

U.S. PATENT DOCUMENTS

| | | | |
|---|---|---|---|
| 3,931,397 A | 1/1976 | Harnden | |
| 4,130,641 A | 12/1978 | Ts'o et al. | |
| 4,283,393 A | 8/1981 | Field et al. | |
| 4,469,863 A | 9/1984 | Ts'o et al. | |
| 4,605,394 A | 8/1986 | Skurkovich | |
| 4,629,320 A | 12/1986 | Lersmacher et al. | |
| 4,689,320 A | 8/1987 | Kaji et al. | |
| 4,766,072 A | * 8/1988 | Jendrisak et al. | ........... 435/91.3 |
| 5,017,488 A | 5/1991 | McAllister et al. | |
| 5,024,938 A | 6/1991 | Nozaki et al. | |
| 5,034,323 A | 7/1991 | Jorgensen et al. | |
| 5,107,065 A | 4/1992 | Shewmaker et al. | |
| 5,173,410 A | 12/1992 | Ahlquist | |
| 5,190,931 A | 3/1993 | Inouye | |
| 5,198,346 A | 3/1993 | Ladner et al. | |
| 5,208,149 A | 5/1993 | Inouye | |
| 5,231,020 A | 7/1993 | Jorgensen et al. | |
| 5,270,163 A | 12/1993 | Gold et al. | |
| 5,272,065 A | 12/1993 | Inouye et al. | .............. 435/91.1 |
| 5,283,184 A | 2/1994 | Jorgensen et al. | |
| 5,349,126 A | 9/1994 | Chappell et al. | |
| 5,365,015 A | 11/1994 | Grierson et al. | |
| 5,405,775 A | 4/1995 | Inouye et al. | |
| 5,434,070 A | 7/1995 | Inouye et al. | |
| 5,453,566 A | 9/1995 | Shewmaker et al. | |
| 5,457,189 A | 10/1995 | Crooke et al. | |
| 5,474,935 A | 12/1995 | Chatterjee et al. | |
| 5,496,698 A | 3/1996 | Draper et al. | |
| 5,514,546 A | 5/1996 | Kool | |
| 5,530,192 A | 6/1996 | Murase et al. | |
| 5,578,716 A | 11/1996 | Szyf et al. | |
| 5,580,703 A | 12/1996 | Kotin et al. | |
| 5,580,767 A | 12/1996 | Cowsert et al. | |
| 5,583,021 A | 12/1996 | Dougherty et al. | |
| 5,597,718 A | 1/1997 | John et al. | |

(Continued)

FOREIGN PATENT DOCUMENTS

| | | |
|---|---|---|
| AU | B-34025/93 | 8/1995 |
| AU | 20891/91 | 10/1997 |
| AU | 20891/97 | 10/1997 |
| AU | 729454 | 5/1998 |
| AU | 729454 | 2/2001 |
| AU | 200195225 A1 | 1/2002 |
| CA | 2012312 | 9/1990 |
| CA | 2370628 A1 | 10/2000 |
| EP | 0213921 A2 | 3/1987 |
| EP | 0223399 | 5/1987 |
| EP | 0240208 | 10/1987 |
| EP | 0281380 A2 | 9/1988 |
| EP | 0286224 A2 | 10/1988 |
| EP | 0300680 A2 | 1/1989 |
| EP | 0303516 A2 | 2/1989 |
| EP | 0306347 A2 | 3/1989 |
| EP | 0308066 A2 | 3/1989 |
| EP | 0318281 A2 | 5/1989 |
| EP | 0325018 A2 | 7/1989 |
| EP | 0347501 A1 | 12/1989 |

(Continued)

OTHER PUBLICATIONS

Fire et al. Nature vol. 391 (Feb. 19, 1998) pp. 806–811.*
Fire et al., Development vol. 113 (1991) pp. 503–514.*
Cameron et al. Nuc. Acids Res. vol. 19(3) pp. 469–475.*
James, Antiviral Chem. & Chemother. vol. 2(4) (1991) pp. 191–214.*
Bissler, Frontiers in Bioscience 3 (Mar. 27, 1998) pp. 408–418.*
Chou et al. Nucleic Acids Research 31(10) pp. 2461–2474 (2003).*
Bussey et al. Nature Genetics: 38(1) (Aug. 2006) pp. 862–863.*
Gunsalus and Piano, Current Opinion in Cell Biology: 17 (2005) pp. 3–8.*

(Continued)

*Primary Examiner*—Padmashri Ponnaluri

(57) ABSTRACT

The present invention relates generally to synthetic genes for modifying endogenous gene expression in a cell, tissue or organ of a transgenic organism, in particular a transgenic animal or plant. More particularly, the present invention provides novel synthetic genes and genetic constructs which are capable of repressing delaying or otherwise reducing the expression of an endogenous gene or a target gene in an organism when introduced thereto.

U.S. PATENT DOCUMENTS

| | | | |
|---|---|---|---|
| 5,624,803 A * | 4/1997 | Noonberg et al. | 435/6 |
| 5,631,148 A | 5/1997 | Urdea | |
| 5,643,762 A | 7/1997 | Ohshima et al. | |
| 5,683,985 A | 11/1997 | Chu et al. | |
| 5,686,649 A | 11/1997 | Chua et al. | |
| 5,691,140 A | 11/1997 | Noren et al. | |
| 5,693,773 A | 12/1997 | Kandimalla et al. | |
| 5,707,835 A | 1/1998 | Haseloff et al. | |
| 5,714,323 A | 2/1998 | Ohshima et al. | |
| 5,739,309 A | 4/1998 | Dattagupta et al. | |
| 5,747,308 A | 5/1998 | Bebbington et al. | |
| 5,747,338 A | 5/1998 | Giese et al. | |
| 5,795,715 A | 8/1998 | Livache et al. | |
| 5,798,265 A | 8/1998 | Springer et al. | |
| 5,801,154 A | 9/1998 | Baracchini et al. | |
| 5,808,036 A | 9/1998 | Kool | |
| 5,814,500 A | 9/1998 | Dietz | |
| 5,850,026 A | 12/1998 | DeBonte et al. | |
| 5,858,981 A | 1/1999 | Schreiber et al. | |
| 5,859,347 A | 1/1999 | Brown et al. | |
| 5,874,555 A | 2/1999 | Dervan et al. | |
| 5,891,855 A * | 4/1999 | Florkiewicz | 514/26 |
| 5,908,779 A | 6/1999 | Carmichael et al. | |
| 5,939,600 A | 8/1999 | Goldbach et al. | |
| 5,952,546 A | 9/1999 | Bedbrook et al. | |
| 5,972,704 A | 10/1999 | Draper et al. | |
| 5,998,383 A | 12/1999 | Wright et al. | |
| 6,010,908 A | 1/2000 | Gruenert et al. | |
| 6,022,863 A | 2/2000 | Peyman | |
| 6,054,299 A * | 4/2000 | Conrad | 435/91.1 |
| 6,069,298 A | 5/2000 | Gengenbach et al. | |
| 6,133,024 A | 10/2000 | Helene et al. | |
| 6,150,585 A | 11/2000 | Goldbach et al. | |
| 6,225,290 B1 | 5/2001 | German et al. | |
| 6,291,504 B1 | 9/2001 | Nugiel et al. | |
| 6,344,316 B1 | 2/2002 | Lockhart et al. | |
| 6,350,575 B1 | 2/2002 | Lusky et al. | |
| 6,369,038 B1 | 4/2002 | Blumenfeld et al. | |
| 6,372,965 B1 | 4/2002 | Lightner et al. | |
| 6,423,885 B1 | 7/2002 | Waterhouse et al. | |
| 6,506,559 B1 * | 1/2003 | Fire et al. | 435/6 |
| 6,531,647 B1 | 3/2003 | Baulcombe et al. | |
| 6,573,099 B2 | 6/2003 | Graham | |
| 6,610,321 B1 | 8/2003 | Huang et al. | |
| 6,635,805 B1 | 10/2003 | Baulcombe et al. | |
| 6,849,448 B1 | 2/2005 | D'Apice et al. | |
| 6,995,258 B1 | 2/2006 | Rossi et al. | |
| 7,064,185 B2 | 6/2006 | Lau | |
| 7,138,565 B2 | 11/2006 | Waterhouse et al. | |
| 2002/0086356 A1 | 7/2002 | Tuschl et al. | |
| 2002/0114784 A1 | 8/2002 | Li et al. | |
| 2002/0150968 A1 | 10/2002 | Wang et al. | |
| 2002/0150986 A1 | 10/2002 | Lau | |
| 2002/0168707 A1 | 11/2002 | Graham | |
| 2003/0018993 A1 | 1/2003 | Gutterson et al. | |
| 2003/0027783 A1 | 2/2003 | Zemicka-Goetz | |
| 2003/0036197 A1 | 2/2003 | Glassman et al. | |
| 2003/0051263 A1 | 3/2003 | Fire et al. | |
| 2003/0055020 A1 | 3/2003 | Fire et al. | |
| 2003/0056235 A1 | 3/2003 | Fire et al. | |
| 2003/0061626 A1 | 3/2003 | Plaetinck et al. | |
| 2003/0074684 A1 | 4/2003 | Graham et al. | |
| 2003/0148519 A1 | 8/2003 | Engelke et al. | |
| 2003/0159161 A1 | 8/2003 | Graham et al. | |
| 2003/0165894 A1 | 9/2003 | Waterhouse et al. | |
| 2004/0022748 A1 | 2/2004 | Ananthapadmanabhan et al. | |
| 2004/0064842 A1 | 4/2004 | Graham et al. | |
| 2004/0106566 A1 | 6/2004 | Lin et al. | |
| 2004/0138168 A1 | 7/2004 | Satishchandran et al. | |
| 2004/0180439 A1 | 9/2004 | Graham et al. | |
| 2004/0214330 A1 | 10/2004 | Waterhouse et al. | |
| 2004/0234504 A1 | 11/2004 | Verma et al. | |
| 2004/0237145 A1 | 11/2004 | Graham et al. | |
| 2004/0266005 A1 | 12/2004 | Graham et al. | |
| 2005/0250208 A1 | 11/2005 | Graham et al. | |
| 2005/0251877 A1 | 11/2005 | Waterhouse et al. | |
| 2006/0014715 A1 | 1/2006 | Graham et al. | |
| 2006/0178335 A1 | 8/2006 | Waterhouse et al. | |
| 2007/0056057 A1 | 3/2007 | Waterhouse et al. | |
| 2007/0078105 A1 | 4/2007 | Waterhouse et al. | |
| 2008/0044906 A1 | 2/2008 | Waterhouse et al. | |
| 2008/0050342 A1 | 2/2008 | Fire et al. | |
| 2008/0081373 A1 | 4/2008 | Fire et al. | |
| 2008/0248576 A1 | 10/2008 | Fire et al. | |

FOREIGN PATENT DOCUMENTS

| | | |
|---|---|---|
| EP | 0350151 A2 | 1/1990 |
| EP | 0467349 | 1/1992 |
| EP | 0522880 | 1/1993 |
| EP | 0560156 | 9/1993 |
| EP | 0647715 | 4/1995 |
| EP | 0 465 572 B1 | 6/1995 |
| EP | 0779364 | 6/1997 |
| EP | 0242016 | 10/1997 |
| EP | 0 921 195 A1 | 6/1999 |
| EP | 0983370 B1 | 3/2000 |
| EP | 0426195 B1 | 10/2001 |
| EP | 0458367 B1 | 10/2001 |
| EP | 1 229 134 A2 | 8/2002 |
| GB | 2353282A A | 2/2001 |
| GB | 2377221 A | 9/2001 |
| JP | H09-110894 A | 4/1997 |
| JP | H09-227413 A | 9/1997 |
| WO | WO 89/05852 | 6/1989 |
| WO | WO 89/10396 | 11/1989 |
| WO | WO 90/11682 | 10/1990 |
| WO | WO-90/12094 A1 | 10/1990 |
| WO | WO-90/12488 A2 | 11/1990 |
| WO | WO-90/14090 A1 | 11/1990 |
| WO | WO 91/02069 | 2/1991 |
| WO | WO 91/16426 | 10/1991 |
| WO | WO 91/16440 | 10/1991 |
| WO | WO 92/04456 | 3/1992 |
| WO | WO 92/11375 | 7/1992 |
| WO | WO 92/11376 | 7/1992 |
| WO | WO 92/13070 | 8/1992 |
| WO | WO 92/17596 | 10/1992 |
| WO | WO-92/18522 A1 | 10/1992 |
| WO | WO 92/19732 | 11/1992 |
| WO | WO 92/21757 | 12/1992 |
| WO | WO 93/05159 | 3/1993 |
| WO | WO 93/10251 | 5/1993 |
| WO | WO 93/17098 | 9/1993 |
| WO | WO 93/23551 | 11/1993 |
| WO | WO 94/01550 | 1/1994 |
| WO | WO 94/09143 | 4/1994 |
| WO | WO 94/17194 | 8/1994 |
| WO | WO 94/18337 | 8/1994 |
| WO | WO 94/29465 | 12/1994 |
| WO | WO-95/03406 A2 | 2/1995 |
| WO | WO 95/07993 | 3/1995 |
| WO | WO 95/09920 | 4/1995 |
| WO | WO 95/10607 | 4/1995 |
| WO | WO 95/15378 | 6/1995 |
| WO | WO 95/15394 | 6/1995 |
| WO | WO-95/18223 A1 | 7/1995 |
| WO | WO-95/18854 A1 | 7/1995 |
| WO | WO 95/23225 | 8/1995 |
| WO | WO-95/34668 A2 | 12/1995 |
| WO | WO 96/08558 | 3/1996 |
| WO | WO-95/35706 A1 | 11/1996 |

| | | |
|---|---|---|
| WO | WO 97/01952 | 1/1997 |
| WO | WO-97/10360 A1 | 3/1997 |
| WO | WO-97/11170 A1 | 3/1997 |
| WO | WO 97/11170 | 3/1997 |
| WO | WO 97/13865 | 4/1997 |
| WO | WO 97/16559 | 5/1997 |
| WO | WO 92/18625 | 10/1997 |
| WO | WO 97/44450 | 11/1997 |
| WO | WO 97/44460 | 11/1997 |
| WO | WO-98/05770 A2 | 2/1998 |
| WO | WO 98/18811 | 5/1998 |
| WO | WO 98/37213 | 8/1998 |
| WO | WO 98/44138 | 10/1998 |
| WO | WO 98/53083 | 11/1998 |
| WO | WO-99/09045 | 2/1999 |
| WO | WO 99/09045 | 2/1999 |
| WO | WO 99/15682 | 4/1999 |
| WO | WO 99/25853 | 5/1999 |
| WO | WO 99/29879 | 6/1999 |
| WO | WO 99/32619 | 7/1999 |
| WO | WO 99/49029 | 9/1999 |
| WO | WO 99/53050 | 10/1999 |
| WO | WO 99/61631 | 12/1999 |
| WO | WO 99/61632 | 12/1999 |
| WO | WO 00/01846 | 1/2000 |
| WO | WO 00/44895 | 8/2000 |
| WO | WO 00/44914 | 8/2000 |
| WO | WO 00/63364 | 10/2000 |
| WO | WO 01/04313 A1 | 1/2001 |
| WO | WO 01/12824 A1 | 2/2001 |
| WO | WO 01/29058 A1 | 4/2001 |
| WO | WO 01/36646 A1 | 5/2001 |
| WO | WO 01/48183 A2 | 7/2001 |
| WO | WO 01/70949 A1 | 9/2001 |
| WO | WO 01/88114 A2 | 11/2001 |
| WO | WO 02/44321 A2 | 6/2002 |
| WO | WO 03/006477 A1 | 1/2003 |
| WO | WO 03/022052 A1 | 3/2003 |
| WO | WO 03/027298 A1 | 4/2003 |
| WO | WO 03/056012 A1 | 7/2003 |
| WO | WO 03/076619 A1 | 9/2003 |

OTHER PUBLICATIONS

Homann et al. Nuc. Acids Res.24:22 (1996) pp. 4395–4400.*

Wang et al., Nuc. Acids. Res.: 21:18 9 (1993) pp. 4383–4391*

Venkataram et al. Nature 382 (Aug. 1, 1996) pp. 471–473.*

U.S. Patent Publication No. 2005/0095199 A1, published May 5, 2005 (U.S. Appl. No. 10/482,888, filed Jun. 14, 2004; Steven Whyard et al.), including complete file history.

Office Action issued Oct. 1, 2009 in connection with U.S. Appl. No. 10/571,384, filed Jun. 1, 2006.

Allen et al. (2007) "Development of strategies for conditional RNA interference," J. Gene Med. 9: 287–298.

Wolff et al. (1995) "Mutational analysis of human U6 RNA: stabilizing the intramolecular helix blocks the splicesomal assembly pathway," Biochim. Biophys. Acta 1263: 39–44.

Image of U6 snoRNA secondary structure retrieved from http://gene.fudan.sh.cn/snoRNASecStruct/Box%20C&D/Homo%20sapiens/U16_ss_p0001.jpg on Sep. 17, 2009.

Bhargava A., et al. (2002) "Glucocorticoids prolong ca(2+) transients in hippocampal–derived H19–7 neurons by repressing the plasma membrane Ca 2+)–ATPase–1" Mol. Endocrinol. 16(7):1629–37.

Bhargava A., et al. (2004) "Long double–stranded RNA–mediated RNA interference as a tool to achieve site–specific silencine of hypothalamic neuropeptides" Brain Res Brain Res Protoc. (2):115–25.

Diallo M., et al. (2003) "Long endogenous dsRNAs can induce complete gene silencing in mammalian cells and primary cultures" Oligonucleotides. 13(5):381–92.

Fedoriw A.M., et al. (2004) "Transgenic RNAi reveals essential function for CTCF in H19 gene imprinting" Science. 303(5655):238–40.

Gan L., et al. (2002) "Specific interference with gene expression and gene function mediated by long dsRNA in neural cells" J. Neurosci Methods. 121(2):151–7.

Lazar, S. et al. (2004) "Selective degradation of cyclin B1 mRNA in rat oocytes by RNA interference (RNAi)" J Mol Endocrinol. 33 (1):73–85.

Stein P., et al. (2003) "Transgenic RNAi in mouse oocytes: a simple and fast approach to study gene function" Dev Biol. 256(1):187–93.

Svoboda P., et al. (2004) "Lack of homologous sequence–specific DNA methylation in response to stable dsRNA expression in mouse oocytes" Nucleic Acids Res. 32(12): 3601–6.

Svoboda, P., et al. (2004) "RNAi and expression of retrotransposons MuERV–L and IAP in preimplantation mouse embryos" Dev Biol. 269(1):276–85.

Yi C.E., et al. (2003) "Specific and potent RNA interference in terminally differentiated myotubes" J Biol Chem. 278(2): 934–9.

Yu J., et al. (2004) "Transgenic RNAi–mediated reduction of MSY2 in mouse oocytes results in reduced fertility" Dev Biol. 268(1):195–206.

Song J., et al. (2004) "Poly(U) and polyadenylation termination signals are interchangeable for terminating the expression of shRNA from a pol II promoter," Biochem Biophys Res Commun. 323(2):573–8.

Clemens MJ. (1997) "PKR—a protein kinase regulated by double–stranded RNA," Int J Biochem Cell Biol.; 29(7): 945–9.

Definition of "palindrome" (1999) Glossary of biotechnology and genetic engineering, p. 172, Zaid, A., et al., eds., Food and Agriculture Organization of the United Nations, Rome, Italy.

Giering J.C., et al. (2008 "Expression of shRNA from a tissue–specific pol II promoter is an effective and safe RNAi therapeutic," Mol. Ther. 16(9):1630–6.

Jacobs BL, Langland JO. "When two strands are better than one: the mediators and modulators of the cellular responses to double–stranded RNA," Virology (1996) 219 (2):339–49.

Memelink et al. (1992) "Structure and Regulation of Tobacco Extensin" The Plant Journal 4: 1011–1012.

Paul CP, Good PD, Winer I, Engelke DR. (2002) "Effective expression of small interfering RNA in human cells," Nat Biotechnol. 20(5):505–8.

Ruiz F, Vayssié L, Klotz C, Sperling L, Madeddu L. (1998) "Homology–dependent gene silencing in *Paramecium*," Mol Biol Cell. 9(4):931–43.

Sánchez Alvarado A, Newmark PA. (1999) "Double–stranded RNA specifically disrupts gene expression during planarian regeneration," Proc Natl Acad Sci U S A. 96(9):5049–54.

Tabara, Hiroaki et al. (1999) "The rde–1 Gene, RNA Interference, and Transposon Silencing in C. elegans", Cell, 99: 123–132.

Doelling JH and Pikaard C S (1995) "The minimal ribosomal RNA gene promoter of *Arabidopsis thaliana* includes a cirtical element at the transcription initiation site" Plant J. Nov; 8(5):683–92.

Sijen et al., Post–transcriptional gene–silencingRNAs on the attack or on the defense?, 2000, BioEssays, vol. 22, 520–513.

Ramezani et al (1997) "Inhibition of HIV–1 replication by retroviral vectors expressing monomeric and multimeric hammerhead ribozymes" Gene Therapy 4 861–867.

Dale et al. (2000) "A test of the model to predict unusually stable RNA hairpin loop stability" RNA 6 608–615.

Minks MA et al. (1979) "Structural requirements of double–stranded RNA for the activation of 2', 5'–oligo(A) polymerase and protein kinase of interferon–treated HeLa cells" J. Biol. Chem. vol. 254, No. 20: 10180–10183.

de Feyter R et al. (1996) "A ribozyme gene and an antisense gene are equally effective in conferring resistance to tobacco mosaic virus on transgenic tobacco" Mol Gen Genet. 250: 329–338.

Fire et al. (1998) "Potent and Specific Genetic Interference by Double–Stranded RNA in *Caenorhabditis elegans*" Nature 391 : 806–822.

Smith, Neil et al. (2000) "Total Silencing by introspliced hairpin RNAs" Nature, 407: 319–320.

Agami et al. (2002) "RNAi and Related Mechanisms And Their Potential Use For Therapy" Current Opinion in Chemical Biology 6:829–834.

Anderson, W.F. (1998) "Human Gene Therapy" 392(6679 Suppl.) :25–30.

Assaad, F.F., et al. (1993) "Epigenetic Repeat–Induced Gene Silencing (RIGS) in *Arabidopsis*" Plant Molecular Biology 22(6) :1067–1085.

Balandin T., and Castresana, C. (1997) "Silencing of a β–1–3–glucanase Transgene is Overcome During Seed Formation" Plant Molecular Biology 34(1) :125–137.

Barry et al. (1993) "Methylation induced premeiotically in ascobolus: coextension with DNA repeat legths and effect on transcript elongation" Proc. Natl. Acad. Sci. 90 : 4557–4561.

Baulcombe, D.C. (1996) "RNA as a Target and an Initiator of Post–Transcriptional Gene Silencing in Transgenic Plants," Plant Molecular Biology 32(1–2) : 79–88.

Becker, W.M., and Deamer, D.W. (1991) "The World of the Cell," pp. 474 to 477 (The Benjamin/Cummings Publishing Company, Inc., Redwood City, California, pub.).

Bevec et al. (1994) "Constitutive expression of chimeric Neo–Rev response element transcripts suppresses HIV–1 replication in human CD4+ T lymphocytes" Human Gene Therapy 5: 193–201.

Blomberg et al. (1990) "Control of Replication of Plasmid R1: the Duplex Between the Antisense RNA, CopA and its Target, CopT, is Processed Specifically in vivo and in vitro by Rnase III" The EMBO Journal 9:2331–2340.

Bingham, P.M. (1997) "Cosuppression Comes to the Animals" Cell 90(3): 385–387.

Bramlage et al. (1998) "Designing Ribozymes for the Inhibition of Gene Expression," Tibtech, 16:434–438.

Brantl et al. (1991) "Copy Number Control of the Streptococcal Plasmid plP501 Occurs at Three Levels" Nucleic Acids Research 20 : 395–400.

Braun and Hemenway (1992) "Expression of Amino–Terminal Portions or Full–Length Viral Replicase Genes in Transgenic Plants Confers Resistance to Potato Virus X Infection" Plant Cell 4:735–744.

Brigneti, Gianinna et al. (1998) "Viral pathogenicity determinants are suppressors of transgene silencing in *Nicotiana benthamiana*" EMBO Journal, 17 (22) : 6739–6746.

Brederode et al. (1995) "Replicase–Mediated Resistance to Alfalfa Mosaic Virus" Virology 207 : 467–474.

Brussian, J.A. et al., (1993) "An Arabidopsis Mutant with a Reduced Level of cabl40 RNA is a Result of Cosuppression" The Plant Cell, American Society of Plant Physiologists, Rockville, MD, USA, 5 : 667–677.

Berns, K., et al. (2004) "A large–scale RNAi screen in human cells identifies new components of the p53 pathway," Nature 428 : 431–437.

Byzova et al. (2004) "Transforming Petals Into Sepaloid Organs in Araidopsis and Oilseed Rape: Implementation of the Hairpin RNA Mediated Gene Silencing Technology in an Organ–Specific Manner" Plants 218 : 379–87.

Cameron et al. (1989) "Specific Gene Suppression by Engineered Ribozymes in Monkey Cells" Proc. Natl. Acad. Sci. USA 86 : 9139–9143.

Caplen et al. (2002) "A New Approach to the Inhibition of Gene Expression" Trends In Biotechnolgy 20 : 49–51.

Carr et al. "Resistance to Tobacco Mosaic Virus Induced by the 54–k Da Gene Sequence Requires Expression of the 54–k Da Protein" Mol. Plant–Micorb. Interact 5 : 397–404.

Chen et al. (2003) "Temporal and Spatial Control of Gene Silencing in Transgenic Plants by Inducible Expression of Double Stranded RNA" The Plant Journal 36 : 731–40.

Chuah et al. (1994) "Inhibition of human immunodeficiencyvirus Type–1 by retroviral vectors expressing antisense–TAR" Human Gene Therapy 5: 1467–1475.

Cogoni, C., et al. (1994) "Suppression of Gene Expression by Homologous Transgenes" Antonie Van Leeuwenhoek 65(3) : 205–209.

Cogoni, C., et al. (1996) "Transgene Silencing of the al–1 Gene in Vegetative Cells of Neurospora is Mediated by a Cytoplasmic Effector and Does not Depend on DNA–DNA Interactions or DNA Methylation" The EMBO Journal 15(12) : 3153–3163.

Cogoni, C., et al. (1997) "Isolations of Quelling–Defective (qde) Mutants Impaired in Posttranscriptional Transgene–Induced Gene Silencing in Neurospora Crassa" PNAS 94 (19) : 10233–10238.

Cogoni, Carlo et al. (1999) "Gene silencing in Neurospora crassa requires a protein homologous to RNA–dependent RNA polymerase" Nature, vol. 399: 166–169.

Cogoni, Carlo et al. (1999) "Posttranscriptional Gene Silencing in Neurospora by a RecQ DNA Helicase" Science, 286: 2342–2344.

Courtney–Gutterson, N., et al. (1994) "Modification of flower color in florist's chrysanthemum: production of a white–flowering variety through molecular genetics," Biotechnology (N.Y.) 12(3) : 268–271.

Covey et al. (1997) "Plants Combat Infection by Gene Silencing," Nature 385 : 781–782.

Citron et al. (1990) "The c4 Repressors of Bacteriophages P1 and P7 Are Antisense RNAs" Cell 62 : 591–598.

Dale et al. (1990) "Intra–and Intermolecular Site–Specific Recombination in Plant Cells Mediated by Bacteriophage P1 Recombinase" Gene 91 : 79–85.

Dalmay, Tamas, et al. (2000) "An RNA–Dependent RNA Polymerase Gene in *Arabidopsis* Is Required for Posttranscriptional Gene Silencing Mediated by a Transgene but Not by a Virus" Cell, 101: 543–553.

Davis, BM et al. (1997) "Expansion of a CUG trinucleotide repeat in the 3' untranslated region of myotonic dystrophy protein kinase transcripts results in nuclear retention of transcripts," Proc. Nat. Acad. Sci. USA 94 : 7388–7393.

de Carvalho F., et al. (1992) "Suppression of β–1 3, –glucanase Transgene Expression in Homozygous Plants" The EMBO Journal 11(7) : 2595–2602.

de Carvalho Niebel, F., et al. (1995) "Post–transsscriptional Cosuppression of β–1, 3–glucanase Genes Does Not Effect Acculmulation of Transgene Nuclear mRNA" The Plant Cell 7(3) : 347–358.

Denoya et al. (1986) "Translational Autoregulation of ermC 23S rRNA Methyltransferase Expression in *Bacillus subtillis*" Journal of Bacteriology 113–1141.

Depicker, A., et al. (1997) "Post–transcriptional Gene Silencing in Plants" Current Opinion in Cell Biology 9(3) : 373–382.

Ding, S.W. (2000) "RNA silencing" Current Opinion in Biotechnology, 11: 152–156.

Domeier, Mary Ellen et al. (2000) "A Link Between RNA Interference and Nonsense–Mediated Decay in *Caenorhabiditis elegans*" Science, 289 : 1928–1930.

Donahue C.P. et al. (1997) "Kinetics of Hairpin Ribozyme Cleavage in Yeast" RNA 3:961–973.

Dorer et al. (1994) "Expansion of transgene repeats cause heterochromatin formation and gene silencing in Drosophilia" Cell 77: 993–1002.

Dorer, D.R. and Henikoff, S. (1997) "Transgene Repear Arrays Interact with Distant Dieterochromatin and Cause Silencing in cis and trans" Genetics 147(3) :1181–1190.

Eckner et al. (1991) "Mature mRNA 3' End Formation Stimulates RNA Export From the Nucleus," EMBO J. 10:3513–3522.

Egli and Braus (1994) "Uncoupling of mRNA 3' Cleavage and Polyadenylation by Expression of a Hammerhead Ribozyme in Yeast," J. Biol. Chem. 269:27378–27383.

Engdahl, H.M., et al. (1997) "A Two Unit Antisense RNA Cassette Test System for Silencing of Target Genes" Nucleic Acids Research 25(16) : 3218–3227.

English, J.J., et al. (1996), "Suppression of Virus Accumulation in Transgenic Plants Exhibiting Silencing of Nuclear Genes", The Plant Cell 8(2) : 179–188.

Exhibit A from *Benitec Australia Ltd. v. Nucleonics, Inc.*, Civil Litigation Action No. 04–174 (D. Del.) (JJF), filed Mar. 22, 2004; Exhibit A, 380 pages, submitted Jan. 28, 2005.

Exhibit B from *Benitec Australia Ltd. v. Nucleonics, Inc.*, Civil Litigation Action No. 04–174 (D. Del.) (JJF), filed Mar. 22, 2004; Exhibit B, 20 pages, submitted Jan. 28, 2005.

Faske, M. et al. (1997) "Transgenic Tobacco Plants Expressing Pea Chloroplast Nmdh cDNA in Sense and AntiSense Orientation," Plant Physiol., Am. Soc. Of Plant Physiologists, Lancaster, PA, 115:705–715.

Garcia et al. (2004) "A Classical Arabinogalactan Protein in Essential for the Initiation of Female Gametogenesis in *Arabidopsis*" The Plant Cell 16:2614–28.

Garrick, D., Fiering, S., Martin, D.I. and Whitelaw, E. (1998) "Repeat–Induced Gene Silencing in Mammals", Nature Genetics 18(1) : 56–59.

Gervaix et al. (1997) "Multigene antiviral vectors inhibit diverse human immunodeficiency virus type 1 clades" Journal of Virology 71(4) : 3048–3053.

Gilbert, S.F. (1997) "Development Biology" 5th ed., Sinauer Associates Inc., Sunderland, MA, pubs.

Gitlin, L., et al. (2005) "Poliovirus escape from RNA interference: short interfering RNA–target recognition and implications for therapeutic approaches," J. Virol. 79: 1027–1035.

Goodwin et al. (1996) "Genetic and Biochemical Dissection of Transgenic RNA–Mediated Virus Resistance" Plant Cell 8:95–105.

Graham, M.W. et al. (1996) "Co–suppression, Anti–Sense and Synthetic Viral Resistance: a Common Mechanism!" Symposium 4–3; Abstract for talk given by Michael Graham at the Lorne Genome Conference, Victoria, Austrialia, Feb. 1996.

Guo et al, (2003) "A Chemical Regulated Inducible RNAi System in Plants" The Plant Journal 34:383–92.

Gura, Trisha (2000) "A silence that speaks volumes" Nature, 404: 804–808.

Hama et al. (1990) "Organization of the Replication Control Region of Plasmid Collb–P9" Journal of Bacteriology 1983–1991.

Hamilton, A.J., et al. (1998) "A Transgene with Repeated DNA Causes High Frequency, Post–Transcriptional Suppression of ACC–Oxidase Gene Expression in Tomato" The Plant Journal 15(6) : 737–746.

Hamilton, Andrew J. et al. (1999) "A Species of Small Antisense RNA in Posttranscriptional Gene Silencing in Plants" Science, 286: 950–952.

Hamilton et al. (1990) "Antisense Gene That Inhibits Synthesis of the Hormone Ethylene in Transgenic Plants" Nature 346:284–287.

Hammond, Scott M. et al. (2000) "An RNA–directed nuclease mediates post–transcriptional gene silencing in Drosophila cells" Nature, 404: 293–296.

Haseloff et al. (1988) "Simple RNA Enzymes With New and Highly Specific Endonuclease Activities," Nature 334 : 585–591.

Heard, D.J., et al. (1995) "An upstream U–snRNA gene–like promoter is required for transcription of the *Arabidopsis thaliana* 7SL RNA gene," Nucleic Acids Res. 23(11) : 1970–6.

Hergersberg, M. (1998) Inaugural Dissertation, Unversität Koln.

Hobbs et al. (1990) "The Effect of T–DNA Copy Number, Position and Methylation on Reporter Gene Expression in Tobacco Transformants" Plant Mol. Biol. 15:851–864.

Ingelbrecht et al. (1994) "Postranscriptional Silencing of Reporter Transgenes in Tobacco Corrects with DNA Methylation" 91:10502–10506.

Itaya A et al., (2001) "Potato spindle tuber viroid as Inducer of RNA Silencing in Infected Tomato," Plant Microbe In. 14(11) : 1332–1334.

Jorgensen, R. (1990) "Altered Gene Expression in Plants Due to Trans Interactions Between Homologous Genes" Trends in Biotechnology 8(12) : 340–344.

Jorgensen, R.A., et al. (1996) "Chalcone Synthase Cosuppression Phenotypes in Petunia Flowers: Comparison of Sense vs. Antisense Constructs and Single–Copy vs. Complex T–DNA Sequences" Plant Molecular Biology 3115) : 957–973.

Jorgensen et al. (1987) "T–DNA is Organized Predominantly In Inverted Repeat Structures in Plants Transformed with Agrobacterium Tumefaciens C58 Derivatives" Mol. Gen. Genet. 207:471–477.

Kappel, C.A., et al. (1992) "Regulating gene expression in transgenic animals," Curr. Opin. Biotechnol. 3(5) : 548–53.

Katsuki, Motoya et al. (1988) "Conversion of Normal Behavior to Shiverer by Myelin Basic Protein Antisense cDNA in Transgenic Mice" Science, 241: 593–595.

Kawcheck et al. (1991) "Sense and Antisense RNA–Mediated Resistance to Potato Leafroll Virus in Russet Burbank Potato Plants" 4:247–253.

Kelton, C.A., et al. (1992) "The cloning of the human follicle stimulating hormone receptor and its expression in COS–7, CHO, Y–1 cells," Mol. Cell. Endocrinol. 89(1–2) : 141–51.

Knoester, M., et al. (1997) "Modulation of Stress–Inducible Ethylene Biosynthesis by Sense and Antisense Gene Expression in Tobacco" Plant Science 126(2) : 173–183.

Kook, Yoon Hoh et al. (1994) "The effect of antisense inhibition of urokinase receptor in human squamous cell carcinoma on malignancy" The EMBO Journal, 13(17) : 3983–3991.

Kuipers et al. (1995) "Factors Affecting the Inhibition by Antisense RNA of Granule–Bound Starch Synthase Gene Expression in Potato" Mol. Gen. Genet. 246:745–755.

Kunz, C., et al. (1996) "Developmentally Regulated Silencing and Reactivaation of Tobacco Chitinase Transgene Expression" The Plant Journal 10(3) : 437–450.

Kubo et al. (1989) "mRNA Secondary Structure in an Open Reading Frame Reduces Translation Efficiency in *Bacillus subtilis*" Journal of Bacteriology 171: 4080–4082.

Kumagai et al. (1995) "Cytoplasmic Inhibition of Carotenoid Biosynthesis With Virus–Derived RNA" Genetics 92:1679–1683.

Lee, K.Y., et al., (1997) "Post–transcriptional Gene Silencing of ACC Synthase in Tomato Results from Cytoplasmic RNA Degradation" The Plant Journal 1215) : 1127–1137.

Lee et al. (1994) "Inhibition of human immunodeficiency virus type 1 human T cells by a potent Rev response element decoy consisting of 13–nucleotide minimal Rev–binding domain" Journal of Virology 68(12) : 8254–8264.

Lee et al. (2003) "Making A Beter RNAi Vector for Drosophila: Use of Intron Spacers" Methods 30:322–9.

Leech et al. (1993) "Expression of myb–related Genes in the Moss, Physcomitrella patens" The Plant Juornal 3 : 51–61.

Li et al. (2005) "The Cotton ACTIN1 Gene is Functionally Expressed in Fibers and Participates in Fiber Elongation" The Plant Cell 17:859–75.

Lindbo, John et al. (1993) "Induction of a Highly Specific Antiviral State in Transgenic Plants: Implications for Regulation of Gene Expression and Virus Resistance" The Plant Cell, 5(12) : 1749–1759.

Lindbo & Dougherty (1992) "Pathogen–Derived Resistance to a Potyvirus: Immune and Resistant Phenotypes in Transgenic Tobacco Expressing Altered Forms of a Potyvirus Coat Protein Nucleotide Sequence" Mol. Plant Micro. Int. 5:144–153.

Lindbo & Dougherty (1992) "Untranslatable Transcripts of the Tobacco Etch Virus Coat protein Gene Sequence Can Interfere With Tobacco Etch Virus Replication in Transgenic Plants and Protoplasts" Virology 189:725–733.

Lindbo, John et al. (2001) "Virus–Mediated Reprogramming of Gene Expression in Plants" Current Opinion in Plant Biology, 4:181–185.

Lisziewicz et al. (1993) "Inhibition of human immunodeficiency virus type 1 replication by regulated expression of a polymeric Tat activation response RNA decoy as a strategy for gene therapy in AIDS" PNAS 90: 8000–8004.

Liu, Z. et al. (1994) "An Efficient New Method to Inhibit Gene Expression" Molecular Biotechnology 2:107, 109–118.

Liu, Z. et al. (1994) "Nuclear Antisense RNA: An Efficient New method to Inhibit Gene Expression," Molecular Biotechnology 2: 107–118.

Liu, Z. et al. (1994) "Targeted Nuclear Antisense RNA Mimics Natural Antisense–Induced Degradation of Polyoma Virus Early RNA" PNAS 91 : 4258–4262.

Longstaff et al. (1993) "Extreme Resistance to Potato Virus× Infection in Plants Expressing a Modified Component of the Putative Viral Replicase" EMBO J. 12:379–386.

Liziewicz et al. (1991) "Tat–Regulated Production of Multimerized TAR RNA Inhibits HIV–I Expression" The New Biologist 3:82–89.

Lo et al. (1992) "Inhibition of Replication of HIB–1by Retroviral Vectors Expressing tat–Antisense an Anti–tat Ribozyme RNA" Virology 190:176–183.

Lovett et al. (1990) "Translational Attenuation as the Regulator of Inducible cat Genes" Journal of Bacteriology 172 : 1–6.

Marathe, R.P (1997) "CIS–Repeat Induced Gene Silencing in Tobacco," Ph.D. Thesis, University of South Carolina.

Marathe, R.P. et al. (1997) "Cis Repeat Induced Gene Silencing in Tobacco," Abstract P10141.

Marx, Jean (2000) "Interfering With Gene Expression" Science, 288: 1370–1372.

Matzke, M.A., et al. (1998) "Epigenetic Silencing of Plant Transgenes as a Consequence of Diverse Cellular Defence Responses" Cellular and Molecular Life Sciences 54(1): 94–103.

Memelink et al. (1992) "Structure and Regulation of Tobacco Extension" The Plant Journal 4 : 1011–1012.

Mette, et al. (1999) "Production of Aberrant Promoter Transcripts Contributes to Methylation and Silencing of Unlinked Homologous Promoters in trans," The EMBO Journal 18 : 241–248.

Meyer, P. (1995) "Understanding and Controlling Transgene Expression" TIBTECH 13 : 332–337.

Meyer, P. (1996) "Homology–Dependent Gene Silencing in Plants" Ann. Rev. Plant Physiol. Plant Mol. Biol. 47 : 23–48.

Meyer, P. (1996) "Repeat–induced Gene Silencing—Common Mechanisms in Plants and Fungi" Biological Chemistry Hoppe–Seyler 377(2) : 87–95.

Miller et al. (1991) "A Satellite RNA of Barley Yellow Dwarf Virus Contains a Novel Hammerhead Structure in the Self–Cleavage Domain" Virology 183 : 711–720.

Moroni, Maria Cristina et al. (1992) "EGF–R Antisense RNA Blocks Expression of the Epidermal Growth Factor Receptor and Suppresses the Transforming Phenotype of a Human Carcinoma Cell Line" J. Bio. Chem., 267(4) : 2714–2722.

Mueller, E., et al. (1995) "Homology–dependent Resistance–13 Transgenic Virus Resistance in Plants Related to Homology–Dependent Gene Silencing" The Plant Journal 7(6) : 1001–1013.

Napoli, C, et al. (1990 "Introduction of a Chimeric Chalcone Synthase Gene into Petunia Results in Reversible Co–Suppression of Homologous Genes in Trans" The Plant Cell 2(4) : 279–289.

Nellen, W. and Lichtenstein C. (1993) "What Makes a Messenger RNA Anti–Sensitive?" Trends in Biochemical Sciences 18(11) : 419–423.

Ngo, V.N., et al. (2006) "A loss–of–function RNA interference screen for molecular targets in cancer," Nature 441:106–110.

O'Brien et al. (2002) "Molecular Analysis of the Stylar–Expressed Solanum Chacoense Small Asparagine–rich Protein Family Related to the HT Modifier of Gametophytic Self–Incompatibility in Nicotiana" The Plant Journal 22 : 985–96.

Paddison, P.J., et al. (2002) "Stable suppression of gene expression by RNAi in mammalian cells," Proc. Natl. Acad. Sci. U.S.A. 99:1443–1448.

Paddison, P.J., et al. (2004) "A resource for large–scale RNA interference–based screens in mammals" Nature 428:427–431.

Palauqui, J.C., et al. (1997) "Systemic Acquired Silencing Transgene–specific Post–transscriptional Silencing is Transmitted by Grafting from Silenced Stocks to Non–silenced scions" The EMBO Journal 16: 4738–4745.

Palauqui, Jean–Christophe et al. (1998) "Transgenes are dispensable for the RNA degradation for the RNA degradation step of cosuppression" Plant Biology, 95: 9675–9680.

Pal–Bhadra, M., Bhadra U. and Birchler, J.A. (1997) "Cosuppression in Drosophila: Gene Silencing of Alcohol Dehydrogenase by White–Adh Tarnsgenes is Polycomb Dependent" Cell 90 (3) : 479–90.

Pang, S.Z., et al. (1997) "Nontarget DNA Sequences Reduce the Transgene Length Necessary for RNA–mediated Tospovirus Resistance in Transgenic Plants" PNAS 94 (15) : 8261–8266.

Pang et al. (1996) "Post–transcriptional Transgene Silencing and Consequent Tospovirus Resistance in Trangenic Lettuce are Affected by Transgene Dosage and Plant Development" Plant J. 9:899–909.

Papefthimiou et al. (2001) "Replicating potato spindle tuber viroid RNA is accomplished by short RNA fragments that are characteristic of post–transcriptional gene silencing," Nucleic Acids Res. 29(11) : 2395–2400.

Parrish, S. et al. (2000) "Functional Anatomy of a dsRNA Trigger: Differential Requirement for the Two Trigger Strands in RNA Interference" Mol. Cell 6:1077–1087.

Park, Y.D., et al. (1996) "Gene Silencing Mediated by Promotor Homology Occurs at the Level of Transcription and Results in Meiotically Heritable Alterations in Methylation and Gene Activity" The Plant Journal 9 (2) : 183–194.

Park, W.S., et al. (2001) "Specific inhibition of HIV–1 gene expression by double–stranded RNA," Nucleic Acids Research Suppl. 1:219–220.

Park, W.S., et al. (2002) "Prevention of HIV–1 infection in human peripheral blood mononuclear cells by specific RNA interference," Nucleic Acids Res. 30:4830–4835.

Perkel, J.M. (2006) "Off–Target Effects Plague Drosophila RNAi" The Scientist, pp. 1–5.

Polyadenylation, Wikipedia, 3 pages, http://en.wikipedia.org/wiki/Polyadenylation (Feb. 20, 2007).

Powell et al. (1990) "Protection Against Tobacco Mosaic Virus Infection in Transgenic Plants Requires Accumulation of Coat Protein Rather than Coat Protein RNA Sequences" Virology 175 : 124–130.

Powell–Abel et al. (1986) "Delay of Disease Development in Trangenic Plants that Express the Tobacco Mosaic Virus Coat Protein Gene" Science 232 : 738–743.

Proud et al. (1995) "PKR: a New Name and New Roles" TIBS 241–246.

Que, Q., et al. (1998) "Homology–based Control of Gene Expression Patterns in Transgenic Petunia Flowers" Developmental Genetics 22 (1) : 100–109.

Que, Q., et al., (1998) "Distinct Patterns Of Pigment Suppression Are Produced By Allelic Sense And Antisense Chalcone Synthase Transgenes In Petunia Flowers" The Plant Journal 13 : 401–409.

Redenbaugh et al. (1992)"Safety Assessment of Genetically Engineered Fruits and Vegetables—A Case Study of the FlavrSavr™ Tomato," CRC Press, Boca Raton, FL.

Robbins, M.A., and Rossi, J.J. (2005) "Sensing the danger in RNA," Nature Med. 11 : 250–251.

Romano, N., et al. (1992) "Quelling: Transient Inactivation of Gene Expression in Neurospora Crassa by Transformation with Homologous Sequences" Molecular Microbiology 6(22) : 3343–3353.

Rubio et al., (1999) "Broad Spectrum Protection Against Tombusviruses Elicited by Defective Interfering RNAs in Transgenic Plants" J. Virology 73 : 5070–5078.

Sadiq, M., et al. (1994) "Developmental Regulation of Antisense–mediated Gene Silencing in Dictyostelium" Antisense Research & Development 4(4) : 263–267.

Sambrook, J., et al. "Molecular Cloning. A Laboratory Model," 2nd ed., pp. 16.1 to 16.81 (Cold Spring Harbor Laboratory Press, Cold Spring Harbor, New York, pub.).

Samuel et al. (2002) "Double–Jeopardy: Both Overexpression and Suppression of a Redox–Activated Plant Mitogen–Activated Protein Kinase Rende Tobacco Plants Ozone Sensitive" The Plant Cell 14 : 2059–69.

Sanford, J.C., et al. (1985) "The Concept of Parasite–Derived Resistance–Deriving Resistance Genes from the Parasite's own Genome," J. Theor. Biol. 13 : 395–405.

Savin, K.W., et al. (1995) "Antisense ACC Oxidase RNA, Delays Carnation Petal Senescence," Hortscience 30 (5) : 970–972.

Scherr et al. (2003) "Gene Silencing Mediated by Small Interfering RNA's in Mammalian Cells" Current Medicinal Chemistry 10 : 245–256.

Schiebel, W. et al. (1993a) "RNA–directed RNA Polymerase from Tomato Leaves" The Journal of Biological Chemistry 268(16) : 11858–11867.

Schiebel, W. et al. (1993b) "RNA–directed RNA Polymerase from Tomato Leaves" The Journal of Biological Chemistry 268(16) : 11858–11867.

Schiedner, G., et al. (1998) "Genomic DNA transfer with a high–capacity adenovirus vector results in improved in vivo gene expression and decreased toxicity," Nat. Genet. 18(2) : 180–3.

Sheehy, R.E. et al. (1998), "Reduction of Polygalacturonase Activity in Tomato Fruit by Antisense RNA" Proc. Natl. Acad. Sci, USA 85 : 8805–8809.

Shi, Y. (2000) "Mammalian RNAi for the masses" Trends Genet. 19(1) : 9–12.

Silva, J.M., et al. (2005) "Second–generation shRNA libraries covering the mouse and human genomes" Nat Genet. 37 : 1281–1288.

Sijen, T., et al. (1996), "RNA–mediated Virus Resistance—Role of Repeated Transgenes and Delineation of Targeted Regions", The Plant Cell 8(12) : 2277–2294.

Smardon, Anne et al. (2000) "EGO–1 is related to RNA–directed RNA polymerase and functions in germ–line development and RNA interference in C. elegans" Current Biology, 10(4) : 169–178.

Smith, Neil et al. (1994) "Transgenic Plant virus Resistance Mediated by Untranslatable Sense RNAs: Expression, Regulation, and Fate of Nonessential RNAs" Plant Cell 6:1441–1453.

Smyth, D.R. (1997) "Gene Silencing: Cosuppression at a Distance" Current Biology 7(12) : R793–795.

Stam, M., et al. (1997) "The Silence of Genes in Transgennic Plants" Annals of Botany 79(1) : 3–12.

Sullenger, B.A. et al. (1991) "Analysis of trans–Acting Response Decoy RNA–Mediated Inhibition of Human Immunodeficiency Virus Type 1 Transactivation" Journal of Virology 65 (12) : 6811–6816.

Sun et al. (1995) "Resistance to human immunodeficiency virus type 1 infection conferred by transduction of human peripheral blook lymphocytes with ribozyme, antisense, or polymeric transactivation response element constructs" PNAS 92: 7272–7276.

Sun et al., (1995) "Target Sequence–Specific Inhibition of HIV–1 Replication by Ribozymes Directed to tat RNA" Nucleic Acides Research 23 : 2909–2913.

Swaney, S. et al. (1995) "RNA–Mediated Resistance with Nonstructural Genes from the Tobacco Etch Virus Genome," MPMI 8 (6) : 1005–1011.

Tabara, H., et al. (1998) "RNAi in C. elegans: Soaking in the Genome Sequence," Science 282 (5388) : 430–431.

Tabara, Hiroaki et al., (1999) "The rde–1 Gene, RNA Interference, and Transposon Silencing in C. elegans", Cell, 99: 123–132.

Takahashi et al. (1997) "Development of Necrosis and Activation of Disease Resistance in Transgenic Plants with Severely Reduced Catalase Levels" The Plant Journal 11 : 993–1005.

Tanzer, M.M., et al. (1997) "Characterization of Post–Transcriptionally Suppressed Transgene Expression that Confers Resistance to Tobacco Etch Virus Infection in Tobacco" The Plant Cell 9(8) : 1411–1423.

Thomas, C.L., et al. (2001) "Size constraints for targeting post–transcriptional gene silencing and for RNA–directed methylation in *Nicotiana benthamiana* using a potato virus× vector," Plant J. 25(4) : 417–25.

Thompson et al. (1995) "Improved Accumulation and Acitivty of Ribozyme Expressed From a tRNA–based RNA Polymerase III Promoter" Nucleic Acids Research 23 : 2259–2268.

Touchette (1996) "Gene Therapy—Not Ready for Prime Time (News)" Nat. Med. 2(1) 7–8.

Tuschl, Thomas et al. (1999) "Targeted mRNA degradation by double–stranded RNA in vitro" Genes & Development, 13: 3919–3197.

Trojan, J., et al. (1992) "Loss of tumorigenicity of rat glioblastoma directed by episome–based antisense cDNA transcription of insulin–like growth factor I," Proc. Natl. Acad. Sci. USA 89:4874–4878.

Vacheret, H. Nussaume, et al. (1997) "A Transciptionally Active State is Required for Post–Transcriptional Silencing (Cosuppression) of Nitrate Reductase Host Genes and Transgenes" The Plant Cell 9 (8) : 1495–1504.

Vaish et al. (1998) "Recent Developments in the Hammerhead Ribozyme Field" Nucleic acids Res. 26:5237–5242.

Van Blokland et al. (1996) "Post–Transcriptional Suppression of Chalcone Synthase Genes in Petunia Hybrida and the Accumulation of Unspliced pre–mRNAA, Mechanisms and Applications of Gene Silencing ".

Van Blokland, R. et al. (1994) "Transgene–mediated Suppression of Chalcone Synthase Expression in Petunia hygrida Results from an increase in RNA Turnover" The Plant Journal 6(6)861–877.

Van der Krol, A.R., et al. (1990) "Flavonoid Genes in Petunia: Addition of a Limited Number of Gene Copies May Lead to a Suppression of Gene Expresson" The Plant Cell 2(4) : 291–299.

Van der Krol, et al. (1990) "Inhibition of Flower Pigmentation by Antisense CHS Genes: Promoter and Minimal Sequence Requirements for the Antisense Effect" Plant Molecular Biology 14(4): 457–466.

van Eldik et al. (1998) "Silencing of β1, 3–glucanase Genes in Tobacco Correlates With an Increased Abundance of RNA Degradation of Intermediates," Nucleic Acids Res 26:5176–5181.

van Houdt et al. (1997) "Post–Transcriptional Silencing of a Neomycin Phosphotransferase II Transgene Correlates With the Accumulation of Unproductive RNAs and With Increased Cytosine Methylation of 3' Flanking Regions," Plant Journal 12:379–392.

Vaucheret et al. (1992) "Inhibition of Tobacco Nitrite Reductase Activity by Ezpression of Antisense RNA" The Plant Journal 2:559–569.

Verma et al. (1997) "Gene Therapy—Promises, Problems and Prospects" Nature 389:239–242.

Vickers, T.A., et al. (2003) "Efficient Reduction of Target RNAs by Small Interfering RNA and RNase H–dependent Antisense Agents. A comparative analysis" J. Biol. Chem.; 278(9):7108–7118.

Voinnet, Olivier et al. (1998) "Systemic Spread of Sequence–Specific Transgene RNA Degradation in Plants Is Initiated by Localized Introduction of Ectopic Promoterless DNA" Cell, 95: 177–187.

Wall, RJ (1996) "Transgenic Livestock: Progress and Prospects for the Future" Theriogenology 45:57–68.

Wang et al (1997) "A factor IX–deficient mouse model for hemophilia B gene therapy" PNAS 94:11563–11566.

Wassenegger and Pelissier (1998) "A Model for RNA–Mediated Gene Silencing in Higher Plants," Plant Mol. Bio. 37:349–362.

Wassenegger, Michael et al. (1999) "Signalling in gene silencing", Elsevier Science, 4(6) : 207–209.

Welch P.J. et al. (1998) "Expression of Ribozymes in Gene Transfer Systems to Modulate Target RNA Levels" Current Opinion in Biotechnology 9:486–496.

Wesley SV et al. (2001) "Construct design for efficient, effective and high–throughput gene silencing in plants," Plant J. 27(6):581–590.

Weerasinghe et al. (1991) "Resistance to Human Immunodeficiency Virus Type 1 (HIV–1) Infenction In Human CD4 Lymphocyte–Derived Cell Lines Conferred by Using Retroviral Vectors Expressing an HIV–1 RNA–Specific Ribozyme" Journal of Virology 65:5531–5534.

Xu, M., et al. (1989) "Immunoglobulin kappa gene expression after stable integration. II. Role of the intronic MAR and enhancer in transgenic mice," J. Biol Chem. 264(35 :21190–5.

Yamamoto, T., et al. (2002 "Double–stranded nef RNA interferes with human immunodeficiency virus type 1 replication," Microbio. Immunol. 46:809–817.

Yu et al. (1995) "In Vitro and in Vivo Characterization of a Second Functional Hairpin Ribozyme Against HIV–1" Virology 26:381–386.

Yu, M., et al. (1993) "A hairpin ribozyme inhibits expression of diverse strains of human immunodeficiency virus type 1," Proc. Natl. Acad. Sci. USA 90:6340–6344.

Erratum to Yu, M., et al. (1993) "A hairpin ribozyme inhibits expression of diverse strains of human immunodeficiency virus type 1," Proc. Natl. Acad. Sci. USA 90(17):8303.

Zamore, Phillip D. et al. (2000) "RNAi: Double–Stranded RNA Directs the ATP–Dependent Cleavage of mRNA at 21 to 23 Nucleotide Intervals", Cell 101: 25–33.

Zhang et al. (2004) "Single Processing Center Models for Human Dicer and Bacterial RNase III," Cell (118): 57–68.

Zhao, Y. et al. (2001) "Use of a vector based on Potato Virus X in a whole plant assay to demonstrate nuclear targeting of Potato spindle tuber viroid," J. Gen. Virol. 83:1491–1497.

Zhou et al. (1994) "Inhibition of HIV–1 in Human T–Lymphocytes by Retrovirally Transduced anti–tat and rev Hammerhead Ribozymes" Gene 149:33–39.

Zrenner et al. (1995) "Evidence of the Crucial Role of Sucrose Synthase for Sink Strength Using Transgenic Potato Plants" The Plant Journal 7:97–107.

Alberts, B., et al. (1989) "Molecular Biology of the Cell" 2nd ed., pp. 102, 486487 and 532–535 (Garland Publishing, Inc., New York, NY, pubs.).

De Lange, P., et al. (1995) "Suppressive of Flavonoid Flower Pigmentation Genes in Petunia Hybrida by the Introduction of Antisense and Sense Genes" Current Topics in Microbiology and Immunology 197: 57–75.

Singer, M.J., et al. (1995) "Genetic and Epigenetic Inactivation of Repetitive Sequences in Neurospora Crassa: RIP, DNA Methylation, and Quelling" Current Topics in Microbiology and Immunology 197: 165–177.

Viville, S. (1997) "Mouse Genetic Manipulation via Homologous Recombination," pp. 307–321, in "Transgenic Animals Generation and Use," (Houdebine, L.M., ed.), Harwood Academic Pubishers, France, pubs.

U.S. Patent No. 7,138,565 B2, issued Nov. 21, 2006 (U.S. Appl. No. 10/152,808, filed May 23, 2002; Peter Michael Waterhouse and Ming–Bo Wang), including complete file history.

Petition to Make Special Under 37 CFR 1.102(d) submitted Jul. 28, 2004 in connection with U.S. Appl. No. 10/821,726, filed Apr. 8, 2004.

U.S. Patent Publication No. 2007–0078105, published Apr. 4, 2007 (U.S. Appl. No. 11/607,062, filed Dec. 1, 2006; Peter Michael Waterhouse et al.), including complete file history.

Office Action issued May 12, 2009 in connection with U.S. Appl. No. 11/607,062, filed Dec. 1, 2006.

Restriction Requirement issued May 4, 2009 in connection with U.S. Appl. No. 11/841,737, filed Aug. 20, 2007.

Definition of "copy" (1995) Webster's New World Dictionary, p. 135, Neufeldt, V., and Sparks, A.N., eds., Simon & Schuster Inc., New York, NY.

Plasmid map for pCR2.1.

Yang, D., et al. (2000) "Evidence that processed small dsRNAs may mediate sequence–specific mRNA degradation during RNAi in *Drosophila* embryos," Curr. Biol. 10(19):1191–1200.

Gross, H.J., et al. (1982) "Nucleotide Sequence and Secondary Structure of Citrus Exocortis and Chrysanthemum Stunt Viroid," Eur. J. Biochem. 121 (2):249–57.

Yu, J.Y., et al. (2002) "RNA interference by expression of short–interfering RNAs and hairpin RNAs in mammalian cells," Proc. Natl. Acad. Sci. USA 99(9):6047–52.

Kumar M and Carmichael G (1998) "Antisense RNA: Function and Fate of Duplex RNA in Cells of Higher Eukaryotes" Microbiol. Mol. Biol. Rev. 62(4): 1415–1434.

Wu H et al. (1998) "Identification and Partial Purification of Human Double Strand RNase Activity" J Biol Chem, vol. 273, Issue 5, 2532–2542.

Sachs A. and Wahle E. (1993) "Poly(A) tail metabolism and function in eucaryotes" J. Biol. Chem. 268: 22955–22958.

Lodish et al. (c1999) "Molecular Cell Biology" Chapter 11, Section 11.2 (New York: W. H. Freeman & Co.).

Huang Y and Carmichael G (1996) "Role of polyadenylation in nucleocytoplasmic transport of mRNA" Mol. Cell. Biol. 16: 1534–1542.

Kim S & Wold BJ (1985) "Stable Reduction of Thymidine Kinase Activity in Cells Expressing High Levels of Anti–Sense RNA" Cell vol. 42, 129–138.

Tuschl T. (2002) "Expanding small RNA interference" Nat Biotechnol. May;20(5):446–8.

Noonberg SB et al. (1994) "In vivo generation of highly abundant sequence–specific oligonucleotides for antisense and triplex gene regulation" Nucleic Acids Research vol. 22 No. 14:2830–2836.

Szyf et al. (1992) "Induction of Myogenic Differentiation by an Expression Vector Encoding the DNA Methyltransferase cDNA Sequence in the Antisense Orientation" J. Biol. Chem., 267:12831–12836.

Wallace RB et al. (1979) "Hybridization of synthetic oligodeoxyribonucleotides to phi chi 174 DNA: the effect of single base pair mismatch." Nucleic Acids Res.6(11):3543–57.

U.S. Appl. No. 60/068,562, filed Dec. 23, 1997, Andrew Fire et al.

U.S. Appl. No. 10/571,384, filed Sep. 10, 2004, Peter Michael Waterhouse et al.

Abdurashitov et al., "BstAPI, an ApaBI Isoschizomer, Cleaves DNA at 5'–GCANNNN↓NTGC–3'," *Nucleic Acids Research*, 1997, vol. 25, No. 12, pp. 2301–2302.

Barabino et al., "Inactivation of the Zebrafish Homologue of Chx10 by Antisense Oligonucleotides Causes Eye Malformations Similar to the Ocular Retardation Phenotype," *Mechanisms of Development*, 1997, vol. 63, pp. 133–143.

Bhan et al., "2',5'–Linked oligo–3'deoxyribonucleoside Phosphorothioate Chimeras: Thermal Stability and Antisense Inhibition of Gene Expression," *Nucleic Acids Research*, 1997, vol. 25, No. 16, pp. 3310–3317.

Buchman et al., "Comparison of Intron–Dependent and Intron–Independent Gene Expression," *Molecular and Cellular Biology*, 1988, vol. 8, No. 10, pp. 4395–4405.

Day et al., "Expression of an Antisense Viral Gene in Transgenic Tobacco Confers Resistance to the DNA Virus Tomato Golden Mosaic Virus," Pro. Natl. Acad. Sci., 1991, vol. 88, pp. 6721–6725.

Dhalla et al., "chk–YB–1b, a Y–box Binding protein Activates Transcription from Rat α1(I) Procollagen Gene Promoter," Biochem J., 1998, vol. 336, pp. 373–379.

Haselbeck et al., "Minimum Intron Requirements for tRNA Splicing and Nuclear Transport in Xenopus Oocytes," Biochemistry, 1993, vol. 32, pp. 8575–8581.

Ma et al., "Design and Synthesis of RNA Miniduplexes via a–Synthetic Linker Approach," *Biochemistry*, 1993, vol. 32, pp.1751–1758.

McGarry et al., "Inhibition of Heat Shock Protein Synthesis by Heat–inducible Antisense RNA," *Proc. Natl. Acad. Sci.*, 1986, vol. 83, pp. 399–403.

Powell–Coffman et al., "Onset of *C. elegans* Gastrulation is Blocked by Inhibition of Embryonic Transcription with an RNA Polymerase Antisense RNA," *Development Biology*, 1996, vol. 178, pp. 472–483.

Stam et al, "Post–Transcriptional Silencing of Chalcone Synthase in *Petunia* by Inverted Transgene Repeats," *The Plant Journal*, 1997, vol. 12, No. 1, pp. 63–82.

Swamynathan et al., "Chicken YB–2, a Y–Box Protein is a Potent Activator of Rous Sarcoma Virus Long Terminal Repeat–Driven Transcription in Avian Fibroblasts," *Journal of Virology*, 1997, vol. 71, No. 4, pp. 2873–2880.

Levin, et al., Methods of Double–Stranded RNA–mediated Gene Inactivation in *Arabidopsis* and Their Use to Define an Essential Gene in Methionine Biosynthesis, *Plant Molecular Biology*, 2000, vol. 44, pp. 759–775.

Tang, et al., Self–stabilized Antisense Oligodeoxynucleotide Phosphorothioates: Properties and Anti–HIV Cavity, *Nucleic Acids Research*, 1993, vol. 21, No. 11, pp. 2729–2735.

U.S. Patent Application Publication No. US–2003/–0056235, publication date—Mar. 20, 2003, "Genetic Inhibition by Double–Stranded RNA", Fire et al.

Amendment and Reply to Office Action filed Nov. 4, 2005 in U.S. Appl. No. 10/282,996.

Final Office Action dated Jan. 25, 2006 issued by the USPTO for U.S. Appl. No. 10/282,996

U.S. Appl. No. 11/218,999, filed Sep. 2, 2005, Graham et al.

Agrawal (1996) Trends Biochem. Sci. 14: 376.
Akgün (Sep. 1997) Mol. Cell. Biol. 17: 5559.
Akhtar (1996) J. Antimicrob. Chemother. 38: 159.
Bahner (1996) J. Virol. 70: 4352.
Barbeau (1996) Biochim. Biophys. Acta 1307: 220.
Baum (1983) Biochem. Biophys. Res. Commun. 114: 41.
Bigler (1995) EMBO J. 14: 5710.
Bisat (1988) Nucl. Acids Res. 13: 6067.
Branch (Feb. 1998) Trends Biochem. Sci. 23; 45.
Brown (Jan. 1993) J. Biol. Chem. 268: 713.
Brummelkamp et al. (Apr. 2002) Science 296: 550–553.
Buchan (1994) Br. J. Pharmacol. 112: 1251.
Caplen et al. (2000) "dsRNA—mediated gene silencing in cultured *Drosphila* cells: a tissue culture model for the analysis of RNA interference" Gene 252: 95–105.
Chernajovsky (1996) DNA Cell Biol. 15: 965.
Christy (1988) Mol. Cell. Biol. 8: 1093.
Clusel (1993) Nucl. Acids Res. 21: 3405.
Clusel (1995) Gene Expression 4: 301.
Coleman et al. (1984) "The use of RNAs complementary to specific mRNAs to regulate the expression of individual bacterial genes" Cell 37: 429–36.
Decoy (1995) J. Clin. Invest. 95: 2749.
Dobrikova (1996) FEBS Lett. 383:327.
Dolnick (1997) Pharm. Ther. 75: 179.
Dougherty (1995) Curr. Opin. Cell Biol. 7: 399.
Dronkert (2000) Mol. Cell. Biol. 20: 3147.
Elroy–Stein (1990) Proc. Nat'l Acad. Sci. USA 87: 6743.
Escudé (Apr. 1996) Proc. Nat'l Acad. Sci. USA 93: 4365.
Faruqi (Oct. 1997) J. Immunol. 159: 3989.
Fiaschi (Nov. 1997) FEBS Lett. 417: 130.
Finkler (1992) Mol. Genet. Genomics 233: 395.
Fuerst (1986) Proc. Nat'l Acad. Sci. USA 83: 8122.
Gao (1997) Nucl. Acids Res. 25: 4740.
Gessani (1989) J. Interferon Res. 9:543.
Gimmi (1989) Nucl. Acids Res. 17: 6983.
Giovannangeli (Jan. 1997) Proc. Nat'l Acad. Sci. USA 94: 79.
Graham, G. (1992) BioTech. 13: 780.
Graham, G. (May 1990) Proc. Nat'l Acad. Sci. USA 87: 5817.
Graham, G. et al. (1990) "RNA transcripts of the Human Immunodeficiency Virus Transactivation Response Element can inhibit action of the viral transactivator" Proc. Nat'l Acad. Sci. USA 87: 5817–21.
Groger (1989) Gene 81: 285.
Hacker (1995) Devel. 121: 1603.
Haines (1991) J. Cell. Biochem. 46: 9.
Harbinder (Nov. 1997) Proc. Nat'l Acad. Sci. USA 94: 13128.
Harcourt (1998) Virol. 252: 179.
Harfe (1998) Genes Devel. 12: 2623.
Henderson (May 1993) Genetics 134: 57.
Hirashima (1989) J. Biochem. 106: 163.
Hirashima (Oct. 1986) Proc. Nat'l Acad. Sci. USA 83: 7726.
Imazeki (Mar. 1988) J. Virol. 62: 861.
Kennerdell et al. (Jul. 2000) Nature Biotechnology 17: 896–898.
Kibler et al. (1997) "Double–Stranded RNA is a Trigger for Apoptosis in Vaccinia Virus–Infected Cells." Journal of Virology 71: 1992–2003.
Klaff (1996) Plant Mol. bio. 32: 89.
Krystal (Jan. 1990) Mol. Cell. Biol. 10: 4180.
Lee (1993) Cell 75: 843.
Lee (1996) Infect. immun. 64: 4802.
Mace (1991) Res. Virol. 142: 213.
Matthieu 91992) Annals N.Y. Acad. Sci. 660: 188.
Mayne (1988) Gene 66: 65.
McCormack (1992) Viorol 188: 47.
McNair (1994) J. Gen. Virol. 75: 1371.
Mercola (1995) Cancer Gene Ther. 2: 47.
Mette (2000) EMBO J. 19: 5194.
Mikoshiba (1990) Ann. N.Y. Acad. Sci. 605: 166.
Morishita (1996) Hypertension 27: 502.
Morris (Aug. 2004) Science 305: 1289.
Nagy (Feb. 1995) J. Biol. Chem. 270: 2755.
Noguchi (Aug. 1994) J. Biol. Chem. 269: 29161.
Palmiter (1984) Cell 36: 869.
Pe'ery (1997) Methods 11: 371.
Peyman (Jan. 1997) *Basic Science of Vascular Disease* (Chapter 17, p. 17).
Pratt (1988) Nucl. Acids Res. 16: 3497.
Raponi (May 2003) Nucl. Acids Res. 31: 4481.
Ratcliff (Jun. 1997) Science 276: 1558.
Resnekov (Jun. 1989) J. Biol. Chem. 264: 9953.
Reuben (1994) Biochim. Biophys. Acta 1219: 321.
Robertson (1996) Nucl. Acids Res. 24: 1465.
Rocheleau (Aug. 1997) Cell 90: 707.
Rodriguez (Oct. 1990) J. Virol. 64: 4851.
Roy (Aug. 1990) Eur. J. Biochem. 191: 647.
Ruskin (1993) Genetics 133: 43.
Sabl (1996) Genetics 142: 447.
Schmitt (1986) Differentiation 30: 205.
Seife et al. (2003) "Breakthrough of the Year" Science 302: 2038–45.

Shaffer (2004) Biotech News 24: 30.
Sharp (1999) Gene Devel. 13: 139.
Silverman (1992) J. Biol. Chem. 267: 9738.
Simons (1988) Gene 72: 35.
Smolinski (1995) Blood 85: 2945.
Smythe (1995) Inflamm. Res. 44: 11.
Sonoda (1996) Vaccine 14: 277.
Sullenger (1990) Cell 63: 601.
Sun (Oct. 1994) Proc. Nat'l Acad. Sci. USA 91: 9715.
Sweetser (1988) Proc. Nat'l Acad. Sci. USA 85: 9611.
Symington (2002) Microbiol. Mol. Biol. Rev. 66: 630.
Tabara (1998) Science 282: 369.
Tanaka (1994) Nucl. Acids Res. 22: 3069.
Tavernarakis et al. (Feb. 2000) Nature Genetics 24: 180–183.
Timmons (Nov. 1998) Nature 395: 854.
Tosic (1990) EMBO J. 9: 401.
Usdin (1993) BioTech. 14: 222.
Van Steeg (1991) Biochem. J. 274: 521.
Volloch (1994) Nucl. Acids Res. 22; 5302.
Wagner et al.. (1998) "Double–stranded RNA poses puzzle" Nature 391: 744–45.
Wang (1994) Biol. Reprod. 51: 1022.
Waterhouse (1999) Proc. Nat'l Acad. Sci. USA 95: 13959.
Williams (1986) Nature 322: 275.
Wolffe (1997) Current Biol. 7: R796.
Wu (1994) J. Interferon Res. 14: 357.
Wu (1996) J. Biol. Chem. 271: 1756.
Xiong (1995) Endocrin. 136: 1828.
Yarney (1993) Mol. Cell. Endroc. 93: 219.
Yu (1994) Gene Therap. 1: 13.
Zakharyan (1986) Doklady Akadem; Nauk SSR 288: 1251.
Zhenhua (1991)Chinese J. Biotech. 7: 279.
Decision to refuse a European patent application dated Jul. 11, 2005, filed in EP 99 910 039.9.
Appeal against decision to refuse a European patent application issued Jul. 11, 2005, filed in EP 99 910 039.9.
Minutes of Oral Proceeding dated Jul. 12, 2005, filed in EP 99 910 039.9.
Reply to Summons to attend Oral Proceeding filed May 13, 2005 in European Patent Application No. 99 910 039.9–2401.
Request for correction of minutes filed Aug. 2, 2005 in EP 99 910 039.9.
In re Opposition to Australian Patent Application No. 743316, Statement of Grounds and Particulars of Opposition.
In re Opposition to Australian Patent Application No. 743316, Statutory Declaration of Dr. Michael Wayne Graham.
In re Opposition to Australian Patent Application No. 743316, Declaration of Dr. Peter Waterhouse.
In re Opposition to Australian Patent Application No. 743316, Declaration of Dr. Robert De Feyter.
In re Opposition to Australian Patent Application No. 743316, Statutory Declaration of Ming–Bo Wang.
In re Opposition to Australian Patent Application No. 743316, Statutory Declaration of Dr. Robert Norman Rice.
In re Opposition to Australian Patent Application No. 743316, Statutory Declaration of Neil Andrew Smith.
In re Opposition to Australian Patent Application No. 743316, Statutory Declaration of Geoffrey Alan Ellacott.
In re Opposition to Australian Patent Application No. 743316, Statutory Declaration of Kenneth Clifford Reed.

In re Opposition to Australian Patent Application No. 743316, Statutory Declaration of William John Pickering.
Table describing sequences used to inhibit viral replication.
Annex A filed in EP 99 910 039.9.
Annex B filed in EP 99 910 039.9.
Annex C filed in EP 99 910 039.9.
Annex D filed in EP 99 910 039.9.
Cohli et al., Inhibition of HIV–1 multiplication in a human CD4+ lymphocytic cell line expressing antisense and sense RNA molecules containing HIV–1 packaging signal and Rev response element(s), *Antisense Research and Development*, 4:19–26 (1994).
European Search Report mailed Jun. 3, 2005, for European patent application No. 04015041, filed Mar. 19, 1999, 4 pages.
Bass, Brenda L. (May 24, 2001) "RNA Interference: The Short answer," Nature, 411:428–429.
Harborth, Jens et al. (2001) "Identification of Essential Genes in Cultured Mammalian Cells Using Small Interfering RNAs," Journal of Cell Science, 114:4557–4565.
Manche, Lisa et al. (Nov. 1992) "Interactions Between Double–Stranded RNA Regulators and the Protein Kinase DAI," Molecular and Cellular Biology, 12(11):5238–5248.
Paddison, Patrick J. et al. (Jul. 2002) "RNA Interference: The New Somatic Cell Genetics?" Cancer Cell, 2:17–23.
U.S. Appl. No. 09/646,807, Graham et al.
International Search Report mailed on May 10, 1999, for PCT patent application No. PCT/AU99/00195, filed on Mar. 19, 1999: 3 pages.
International Search Report mailed on May 10, 2001, for PCT patent application No. PCT/AU01/00297, filed on Mar. 16, 2001: 3 pages.
International Search Report mailed on Nov. 14, 2002, for PCT patent application No. PCT/AU02/01326, filed on Sep. 27, 2002; 5 pages.
Written Opinion mailed on Apr. 17, 2004, for PCT application No. PCT/AU03/01177 filed Sep. 9, 2003: 7 pages.
Hungarian Patent Office Search Report mailed Jul. 13, 2004 for Hungarian patent application No. P0101225, 1 page.
Agrawal, Sudhir et al. (1995) "Self–Stabilized Oligonucleotides as Novel Antisense Agents" pp. 105–120.
Agrawal et al. (2003) "RNA Interference: Biology, Mechanism, and Applications" Microb. Mol. Biol. Rev. 67:657–685.
Angell, S.M., et al. (1997), "Consistent Gene Silencing in Transgenic Plants Expressing a Replicating Potato Virus X RNA", The EMBO Journal 16(12):3675–3684.
Bahramian, Mohammad B. and Zarbl, Helmut (1999) "Transcriptional and Posttranscriptional Silencing of Rodent α1(I) Collagen by a Homologous Transcriptionally Self–Silenced Transgene" Molecular and Cellular Biology, vol. 19, No. 1:274–283.
Bhan, Purshotam et al. (1997) "2',5'–Linked Oligo–3'–deoxyribonucleoside Phosphorothiate Chimeras: Thermal Stability and Antisense Inhibition of Gene Expression" Nucleic Acids Research, vol. 1, No. 16: 3310–3317.
Billy, E. et al. (2001) "Specific interference with gene expression induced by long, double–stranded RNA in mouse embryonal teratocarcinoma cell lines." Proceedings of the National Academy of Sciences of the United States of America 98(25) 14428–33.
Birchler, James A. (2000) "Making noise about silence: repression of repeated genes in animals" Current Opinion in Genetics & Development 10: 211–216.

Boldin, Mark P. et al. (1996) "Involvement of MACH, a Novel MORT1/FADD–Interacting Protease, in Fas/APO–1– and TNF Receptor–Induced Cell Death" Cell 85: 803–815.

Borecky, L. et al. (1981–1982) "Therapeutic Use of Double–Stranded RNAs in Man" Tex Rep Biol Med 14: 575–581.

Braich, Ravinderjit and Damha, Masad J. (1997) "Regiospecific Solid–Phase Synthesis of Branched Oligonucleotides. Effect of Vicinal 2',5'– (or 2',3'–) and 3',5'– Phosphodiester Linkages on the Formation of Hairpin DNA" Bioconjugate Chem, 8: 370–377.

Brummell, David A. et al. (2003) "Inverted repeat of a heterologous 3'–untranslated region for high–efficiency high–throughput gene silencing" The Plant Journal 33: 793–800.

Brummelkamp, R. et al. (2002) "A System for Stable Expression of Short Interfering RNAs in Mammalian Cells" Science vol. 296: 550–553.

Carthew (2001) "Gene Silencing By Double–Stranded RNA" Curr. Op. Cell. Biol. 13: 244–248.

Cogoni, Carlo and Giuseppe Macino (2000) "Post–transcriptional gene silencing across kingdoms" Current Opinion in Genetics & Development 10: 638–643.

Couzin, Jennifer (2002) "Small RNAs Make Big Splash" Science 298: 2296–2297.

Czauderna, Frank et al. (2003) "Structural Variations and Stabiling Modifications of Synthetic siRNAs in Mammalian Cells" Nucleic Acids Research vol. 31, No. 11: 1–12.

Doench, John G. et al. (2003) "siRNA Can Function as miRNAs" Genes and Development 17:438–442.

Dykxhoorn, D. et al. (2003) "Killing the Messenger: Short RNAs that Silence Gene Expression." Nature Reviews Molecular Cell Biology vol. 4: 457–467.

Elbashir, S.M. et al. (2001) "Duplexes of 21–nucleotide RNAs mediate RNA interference in cultured mammalian cells." Nature 411(6836): 494–8.

Elbashir, Sayda M. et al. (2001) "Functional Anatomy of siRNAs for mediating Efficient RNAi in Drosophila Melanogaster Embryo Lysate" The EMBO Journal, vol. 20, No. 23: 6877–6888.

Elbashir, Sayda M. et al. (2002) "Analysis of Gene Function in Somatic Mammalian Cells Using Small Interfering RNAs" Methods 26: 199–213.

Fire, A. (1999) "RNA–triggered gene silencing" Trends Genet. 15(9): 358–363.

Fire, A. et al. (1991) "Production of antisense RNA leads to effective and specific inhibition of gene expression in *C. elegans* muscle" Development 113: 503–514.

Flavell, R. B. (1994) "Inactivation of Gene Expression in Plants as a Consequence of Specific Sequence Duplication" Proc. Natl. Acad. Sci. 99:3490–3496.

Fraser et al. (1996) "Effects of c–myc first exons and 5' synthetic hairpins on RNA translation in oocytes and early embryos of *Xenopus laevis*" Oncogene 12(6):1223–30.

Giordano, E. et al. (2000) "RNAi Triggered By Symmetrically Transcribed Transgenes in Drosophila Melanogaster" Genetics, 160:637–648.

Goff, Deborah J. e al. (1997) "Analysis of Hoxd–13 and Hoxd–11 Misexpression in Chick Limb Buds Reveals that Hox Genes Affect Both Bone Condensaton and Growth" Development 124: 627–636.

Good, et al. (1997) "Expression of small, therapeutic RNAs in human cell nuclei" Gene Ther. 4(1): 45–54.

Grant, Sarah R. (1999) "Dissecting the Mechanisms of Posttranscriptional Gene Silencing: Divide and Conquer" Cell 96: 303–306.

Grasby, Jane A. et al. (1995) "Purine Functional Groups in Essential Residues of the Hairpin Ribozyme Required for Catalytic Cleavage of RNA" Biochemistry 34: 4068–4076.

Griffey, Richard H. et al. (1996) "2'O–Aminopropyl Ribonucleotides: A Zwitterrionic Modification That Enhances The Exonuclease Resistance and Biological Activity of Antisense Oligonucleotides" J. Med. Chem 39: 5100–5109.

Gryaznov, Sergei M. and Letsinger, Robert L. (1993) "Template Controlled Coupling and Recombination of Oligonucleotide Blocks Containing Thiophosphoryl Groups" Nucleic Acids Research, vol. 21, No. 6: 1403–1408.

Ha, Ilho et al. (1996) "A Bulged 1in–4/1in–14 RNA Duplex is Sufficient For *Caenorhabditis elegans* 1in–14 Temporal Gradient Formation" Gene and Development 10: 3041–3050.

Hannon Gregory J. (2002) "RNA Interference" Nature, vol. 418: 244–251.

Hoke, Glenn D. et al. (1991) "Effects of Phosporothioate Capping On Antisense Oligonucleotide Stability, Hybridization and Antiviral Efficacy Versus Herpes Simplex Virus Infection" Nucleic Acids Research, vol. 19, No. 20: 5743–5748.

Jorgensen et al. (1999) "Do Unintended Antisense Transcripts Contribute To Sense Cosuppression in Plants" TIG 15:11–12.

Kennerdell, J. R. et al. (2000) "Heritable Gene Silencing in Drosophila Using Double–Stranded RNA" Nature Biotechnology, 18:896–898.

Kennerdell, Jason R. and Carthew, Richard W. (1998) "Use of dsRNA–Mediated Genetic Interference to Demonstrate that Frizzled and Frizzled 2 Act in the Wingless Pathway" Cell, vol. 95: 1017–1026.

Kibler, Karen V. et al. (1997) "Double–Stranded RNA is a Trigger for Apoptosis in Vaccinia Virus–Infected Cells" Journal of Virology 71 (3): 1992–2003.

Kitabwalla, Moiz and Ruprecht Ruth M. (2002) "RNA Interference—A New Weapon Against HIV and Beyond" N Engl J Med, vol. 347, No. 17: 1364–1367.

Klink et al. (2000) The Efficacy of RNAi in the Study of the Plant Cytoskeleton J. Plant Growth Reg. 19: 371–384.

Kowolik, Claudia M. and Jee, Jiing–Kuan (2002) "Preferential Transduction of Human Hepatocytes with Lentiviral Vectors Pseudotyped By Sendai Virus F Protein" Molecular Therapy, vol. 5, No. 6: 762–769.

Kowolik, Claudia M. (2001) "Locus Control Region of the Human CD2 Gene in a Lentivirus Vector Confers Position–Independent Transgene Expression" Journal of Virology, vol. 75, No. 10: 4641–4648.

Kozak (1989) "Circumstances and mechanisms of inhibition of translation by secondary structure in eucaryotic mRNAs" Mol. Cell. Biol. 9:5134–5142.

Kreutzer R. et al. "Specific Inhibition of Viral Gene Expression by Double–Stranded RNA in Vitro" Fall Meeting S169.

Kumar, Madhur and Carmichael, Gordon G. (1998) "Antisense RNA: Function and Fate of Duplex RNA in Cells of Higher Eukaryotes" Microbiology and Molecular Biology Reviews, vol. 62, No. 4: 1415–1434.

Li, Y.X. et al. (2000) "Double–Stranded RNA Injections Produces Null Phenotype in Zebrafish" Dev. Biol. 217(2):394–405, Erratum in: Dev. Biol. (2000) 220(2):432.

Liebhaber et al. (1992) "Translation inhibition by an mRNA coding region secondary structure is determined by its proximity to the AUG initiation codon"0 J. Mol. Biol. 226:609–621.

Lin, Rueyling and Avery, Leon (1999) "Policing Rogue Genes" Nature vol. 402: 128–129.

Lingelbach et a., (1988) "An extended RNA/RNA duplex structure within the coding region of mRNA does not block translational elongation" Nuc. Acids Res. 16 3405–3414.

Lipinski, Christopher A. et al. (1997) "Experimental and Computational Approaches to Estimate Solubility and Permeability in Drug Discovery and Development Settings" Advanced Drug Delivery Reviews 23: 3–25.

Lisziewicz et al. (1991) "Tat–Regulated Production of Multimerized TAR RNA Inhibits HIV–1 Gene Expression" New Biologist 3:82–89.

Loomis et al. (1991) "Antisense RNA Inhibition of expression of a pair of tandemly repeated genes results in a delay in cell–cell adhesion in Dictyostelium" Antisense Res. Dev.1:255–260.

Ma, Michael Y.X. et al. (1993) "Design and Synthesis of RNA Miniduplexes via a Synthetic Linker Approach" Biochemistry 32; 1751–1758.

Majumdar, Alokes et al. (1998) "Targeted Gene Knockout Mediated by Triple Helix Forming Oligonucleotides" Nature Genetics vol. 20: 212–214.

Marathe, Rajendra et al. (2000) "RNA virues as inducers, suppressors and targets of post–transcriptional gene silencing" Plant Molecular Biology 43: 295–306.

Matzke, Marjori and Antonius, J.M. Matzke (2003) "RNAi Extends Its Reach" Science: 1060–1061.

Matzke, Marjori A. and A. J. M. Matzke (1995) "How and Why Do Plants Inactivate Homologous (Trans)genes" Plant Physiol. 107: 679–685.

McKenzie, et al. (1999) "Xenotransplantation" Eds. Ginns et al. Transplantation, Science Inc.: 827–874.

McManus et al. (2002) "Gene Silencing in Mammals By Small Interfering RNAs" Nat. Rev. Genet. 3 (10): 737–747.

Metzlaff et al. (1997) "RNA–Mediated RNA Degradation and Chalcone Synthase A Silencing in Petunia" Cell 88:845–854.

Mikoshiba et al. (1991) "Molecular biology of myelin basic protein: gene rearrangement and expression of anti–sense RNA in myelin–deficient mutants" Comp. Biochem. Physiol. 98:51–61.

Milhaud, Pierre G. et al. (1991) "Free and Liposome–Encapsulated Double–Stranded RNAs as Inducers of Interferon, Interleukin–6, and Cellular Toxicity" Journal of Interferon Research 11: 261–265.

Montgomery, Mary K. and Fire, Andrew (1998) "Double–Stranded RNA as a Mediator in Sequence–Specific Genetic Silencing and Co–Suppression" TIG, vol. 14, No. 7: 255–258.

Montgomery, Mary K. et al. (1998) "RNA as a Target of Double–Stranded RNA–Mediated Genetic Interference in *Caenorhabditis elegans*" Proc. Natl. Acad. Sci. vol. 95: 15502–15507.

Moss, Eric G. et al. (1997) "The cold Shock Domain Protein LIN–28 Controls Development Timing in *C. elegans* and is Regulated by the lin–4 RNA" Cell, vol. 88: 637–646.

Ngo, Huan et al. (1998) "Double–Stranded RNA Induces mRNA Degradation in *Trypanosoma brucei* "Proc. Natl. Acad. Sci. vol. 95: 14687–14692.

Nielsen, Paul et al. (1997) "A Novel Class of Conformationally Restricted Oligonucleotide Analogues: Synthesis of 2',3'–Bridged Monomers and RNA–Selective Hybridisation" Chem. Commun., pp. 825–826.

Nikiforov, Theo T. and Connolly, Bernard A. (1992) "Oligodeoxynucleotides Containing 4–thiothymidine and 6–thiodeoxyguanosine as affinity labels for the Eco RV Restriction Endonuclease and Modification Methylase" Nucleic Acids Research, vol. 20, No. 6: 1209–1214.

Oates, Andrew C. et al. (2000) "Too Much Interference: Injection of Double–Stranded RNA Has Nonspecific Effects in the Zebrafish Embryo" Developmental Biology 224: 28–28.

Okano et al. (1991) "Myelin basic protein gene and the function of antisense RNA in its repression in myelin–deficient mutant mouse" J. Neurochem. 56:560–567.

Paddison, Patrick J. et al. (2002) "Short Hairpin RNAs (shRNAs) Induce Sequence–Specific Silencing in Mammalian Cells" Genes and Development 16: 948–958.

Pegram, Mark D. et al. (1998) "Phase II study of Receptor–Enhanced Chemosensitivity Using Recombinant Humanized Anti–p185$^{HER2/neu}$ Monoclonal Antibody Plus Cisplatin in Patients With HER2/Neu–Overexpressing Metastatic Breast Cancer Refractory to Chemotherapy Treatment" Journal of Clinical Oncology, vol. 16, No. 8: 2659–2671.

Pelletier et al. (1985) "Insertion mutagenesis to increase secondary structure within the 5' noncoding region of a eukaryotic mRNA reduces translational efficiency" Cell, 40:515–526.

Peng, Hairong et al. (2001) "Development of an MFG–Based Retroviral Vector System for Secretion of High Levels of Functionally Active Human BMP4" Molecular Therapy, vol. 4, No. 2: 95–104.

Piccin, et al. (2001) "Efficient and Heritable Functional Knock–out of an Adult Phenotype in *Drosophila* using a GAL–4–Driven Hairpin RNA Incorporating a Heterologous Spacer" *Nucleic Acids Research*, 29(12) E55:1–5.

Plasterk et al. (2000) "The Silence of the Genes" Curr. Op. Gen. Dev. 10:562–567.

Putlitz, Jasper Zu and Jack R. Wands (1999) Specific Inhibition of Hepatitis B Virus Replication by Sense RNA Antisense & Nucleic Acid Drug Development 9: 241–252.

Que et al. (1997) "The Frequency and Degree of Cosuppression by Sense Chalcone Synthase Transgenes Are Dependent on Transgene Promoter Strength and Are Reduced by Premature Nonsense Codons in the Transgene Coding Sequence" Plant Cell 9: 1357–1368.

Regalado, A. (Aug. 2002). "Turning Off Genes Sheds New Light On How They Work" *The Wall Street Journal*, 4 pages.

Sarver et al. (1990) "Ribozymes as Potential Anti–HIV–1 Therapeutics Agents" Science 247:1222–1225.

Schaller (2003) "The Role of Sterols in Plant Growth and Development" Prog. Lipid Res. 42:163–175.

Schmidt, Frank R. (2004) "RNA Interference Detected 20 years ago" Nat. Biotechnol. 22: 267–268.

Schmidt, F. R. et al. (1983) "Cycloheximide Induction of Aflatoxin Synthesis in a Nontoxigenic Strain of *Aspergillus flavus*" Bio/Technology 1: 794–795.

Schmidt, Frank R. et al. (1986) "Viral Influences on Aflatoxin Formation by *Aspergillus flavus*" Appl Microbiol. Biotechnol. 24: 248–252.

Schramke, Vera and Robin Allshire (2003) "Hairpin RNAs and Retrotransposon LTRs Effect RNAi and Chromatin–Based Gene Silencing" Science 301: 1069–1074.

Schwarz, Dianne S. et al. (2002) "Evidence that siRNAs Function as Guides, Not Primers in the *Drosophila* and Human RNAi Pathways" Molecular Cell, vol. 10: 537–548.

Selker (1999) "Gene Silencing: repeats that count" Cell 97(2): 157–160.

Sharp, Phillip (1999) "RNAi and Double–Stranded RNA" Genes and Development 13(2): 139–141.

Shi, Yang and Mello, Craig (1998) "A CBP/p300 Homolog Specifies Multiple Differentiation Pathways in *Caenorhabditis elegans*" Genes and Development (12)7: 943.

Sinha, Nanda D. (1997). "Large–Scale Synthesis: Approaches to Large–Scale Synthesis of Oligodeoxynecleotides and their Analog" Antisense From Technology to Therapy Lab Manual and Textbook, vol. 6: pp. 30–58.

Skripkin, Eugene et al. (1996) "Psoralen Crosslinking Between Human Immunodeficiency Virus Type 1 RNA and Primer tRNA$_3^{Lys}$" Nucleic Acids Research, vol. 24, No. 3: 509–514.

Steinecke et al. (1992) "Expression of a Chimeric Ribozyme Gene Results in Endonucleolytic Cleavage of a Target mRNA and a Concomitant Reduction of Gene Expression in vivo" Nucleic Acids Res. 23:2259–2268.

Strauss, Evelyn (1999) "Candidate Gene Silencers' Found" Science vol. 286, p. 886.

Sullenger et al. (1990) "Expression of Chimeric tRNA–Driven Antisense Transcripts Renders NIH 3T3 Cells Highly Resistant to Moloney Murine Leukemia Virus Replication" Mol. Cell. Biol. 10:6512–6523.

Sullenger et al. (1993) "Tethering Ribozymes to a Retroviral Packaging Signal for Destruction of Viral RNA" Science 262:1566–1569.

Svoboda, P. et al. (2000) "Selective reduction of dormant maternal mRNAs in mouse oocytes by RNA interference." Development 127(19): 4147–4156.

Svoboda, P. et al. (2001) "RNAi in Mouse Oocytes and Preimplantation Embryos: Effectiveness of Hairpin dsRNA" *Biochem Biophys Res Commun.*, 287(5): 1099–1104.

Tavernarakis, Nektarios et al. (2000) "Heritable and inducible genetics interference by double–stranded RNA encoded by transgenes" Nature Genetics 24: 180–183.

Tijsterman et al. (2002) "The Genetics of RNA Silencing" Ann. Rev. Genet. 36:489–519.

Timmons, Lisa and Fire, Andrew (1998) "Specific Interference by Ingested dsRNA" Nature, vol. 395: 854.

Uhlmann, Eugen and Peyman, Anusch (1990) "Antisense Oligonucleotides: A New Therapeutic Principle" Chemical Reviews, vol. 9, No. 4: 544–584.

Ui–Tei, Kumiko et al. (2000) "Sensitive assay of RNA interference in *Drosophila* and Chinese hamster cultured cells firefly luciferase gene as target" Federation of European Biochemical Societies Letters 479: 79–82.

Wargelius, Anna et al. (1999) "Double–Stranded RNA Induces Specific Developmental Defects in Zebrafish Embryos" Biochemical and Biophysical Research Communications 263: 156–161.

Watson (1988) "A new revision of the sequence of plasmid pBR322" Gene 70:399–403.

Weaver et al. (1981) "Introduction by molecular cloning of artifactual inverted sequences at the 5' terminus of the sense strand of bovine parathyroid hormone cDNA" PNAS 78: 4073–4077.

Wess, Ludger and Haan, Keith (2003) "Early Days for RNAi" BioCentury, vol. 11, No. 12: A1–23.

Yam, Priscilla Y. et al. (2002) "Design of HIV Vectors for Efficient Gene Delivery into Human Hematopoietic Cells" Molecular Therapy, vol. 5, No. 4: 479–484.

Yamamoto, Rika et al. (1997) "Inhibition of Transcription by the TAR RNA of HIV–1 in a Nuclear Extract of HeLa Cells" Nucleic Acids Research, vol. 25, No. 17: 3445–3450.

Yang, S. et al. (2001) "Specific double–stranded RNA interference in undifferentiated mouse embryonic stem cells." Molecular and Cellular Biology 21(22): 7807–16.

Yee, Jiing–Kuan and Zaia, John A. (2001) "Prospects for Gene Therapy Using HIV–Based Vectors" Somatic Cell and Molecular Genetics, vol. 26, Nos. 1/6: 159–173.

Zhao et al. (1993) "Generating Loss–of–Function Phenotype of the Fushi Tarazu Gene with a Targeted Ribozyme in *Drosophila*" Nature 365:448–451.

Agrawal et al. (2000) "Antisense therapeutics: is it as simple as complementary base recognition?" Molecular Medicine Today 6: 72–81.

Cameron et al. (1994) "Multiple Domains in a Ribozyme Construct Confer Increased Suppressive Activity in Monkey Cells" Antisense Research and Development 4: 87–94.

Harborth et al. (2003) "Sequence, Chemical, and Structural Variation of Small Interfering RNAs and SHort Hairpin RNAs and the Effect on Mammalian Gene Silencing" Antisense and Nucleic Acid Drug Development 13: 85–105.

Holen et al. (2002) "Positional effects of short interfering RNAs targeting the human coagulation trigger Tissue Factor" Nucleic Acids Research 30 (8): 1757–1766.

Jen et al. (2000) "Suppression of Gene Expression by Targeted Disruption of Messenger RNA: Available Options and Current Strategies" Stem Cells 18: 307–319.

McManus et al. (2002) "Gene Silencing using micro–RNA designed hairpins" RNA 8: 842–850.

McManus et al. (2002) "Small Interfering RNA–Mediated Gene Silencing in T Lymphocytes" Journal of Immunology 169: 5754–5760.

Opalinska et al. (2002) "Nucleic–Acid Therapeutics: Basic Principles and Recent Applications" Nature Reviews 1; 503–514.

Randall et al. (2003) "Clearance of replicating hepatitis C virus replicon RNAs in cell culture by small interfering RNAs" PNAS 100 (1): 235–240.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-3 and 8-9 are cancelled.

Claims 4-7 and 10-22 are determined to be patentable as amended.

New claims 23-41 are added and determined to be patentable.

4. An isolated [genetic] *double-stranded DNA* construct which is capable of delaying, repressing or otherwise reducing the expression of a target gene in an animal cell which is transfected with said [genetic] *double-stranded DNA* construct, wherein said [genetic] *double-stranded DNA* construct comprises at least two *identical* copies of a structural gene sequence and each *identical* copy of said structural gene sequence is separately placed under the control of a promoter which is operable in said cell, and wherein said structural gene sequence comprises a nucleotide sequence which is substantially identical to [at least] a region of said target gene, wherein at least one *identical* copy of said structural gene sequence is placed operably in the sense orientation under the control of an individual promoter sequence, and wherein at least one other *identical* copy of said structural gene sequence is placed operably in the antisense orientation under the control of another individual promoter sequence.

5. An isolated [genetic] *double-stranded DNA* construct which is capable of delaying, repressing or otherwise reducing the expression of a target gene in an animal cell which is transfected with said [genetic] *double-stranded DNA* construct, wherein said [genetic] *double-stranded DNA* construct comprises at least two *identical* copies of a structural gene sequence, wherein said structural gene sequence comprises a nucleotide sequence which is substantially identical to [at least] a region of said target gene, and wherein said at least two *identical* copies of said structural gene sequence are placed operably under the control of a single promoter sequence which is operable in said cell, wherein at least one *identical* copy of said structural gene sequence is placed operably in the sense orientation under the control of said promoter sequence, wherein at least one other *identical* copy of said structural gene sequence is placed operably in the antisense orientation under the control of said promoter sequence, and wherein said at least one *identical* copy of said structural gene sequence that is placed in the sense orientation relative to said promoter and said at least one *identical* copy of said structural gene sequence that is placed in the antisense orientation relative to said promoter are spaced from each other by a nucleic acid stuffer fragment.

6. An animal cell comprising the [genetic] *double-stranded DNA* construct of [any one of claims 1-2 or 3-] *claim 5*.

7. A method of delaying or repressing the expression of a target gene in an animal cell, comprising transfecting said animal cell with a [genetic] *double-stranded DNA* construct, wherein said [genetic] *double-stranded DNA* construct comprises at least two *identical* copies of a structural gene sequence, wherein said structural gene sequence comprises a nucleotide sequence which is substantially identical to [at least] a region of said target gene, and wherein said at least two *identical* copies of said structural gene sequence are placed operably under the control of a single promoter sequence which is operable in said cell, wherein at least one *identical* copy of said structural gene sequence is placed operably in the sense orientation under the control of said promoter sequence *and wherein at least one other identical copy of said structural gene sequence is placed operably in the antisense orientation under the control of said promoter sequence, wherein said identical copy of said structural gene sequence that is placed in the sense orientation relative to said promoter and said identical copy of said structural gene sequence that is placed in the antisense orientation relative to said promoter are spaced from each other by a nucleic acid stuffer fragment*.

10. A method of delaying or repressing the expression of a target gene in an animal cell, comprising expressing in said animal cell a [genetic] *double-stranded DNA* construct, wherein said [genetic] *double-stranded DNA* construct comprises at least two *identical* copies of a structural gene sequence, wherein each *identical* copy of said structural gene sequence is separately placed under the control of a promoter which is operable in said cell, and wherein said structural gene sequence comprises a nucleotide sequence which is substantially identical to [at least] a region of said target gene, wherein at least one *identical* copy of said structural gene sequence is placed operably in the sense orientation under the control of an individual promoter sequence, *and wherein at least one other identical copy of said structural gene sequence is placed operably in the antisense orientation under the control of another individual promoter sequence*.

11. The isolated [genetic] *double-stranded DNA* construct according to [any one of claims 1, 2 or 3-] *claim 5*, wherein said region of the target gene is [20 to] 30 nucleotides long.

12. The method according to [any one of claims] *claim 7* [-9 or 10], wherein said region of the target gene is [20 to] 30 nucleotides long.

13. The isolated [genetic] *double-stranded DNA* construct according to [any one of claims 1, 2 or 3-] *claim 5*, comprising two *identical* copies of said strucutral gene sequence.

14. The isolated [genetic] *double-stranded DNA* construct according to [any one of claims 1, 2 or 3 -] *claim 5*, wherein said region of the target gene is [at least] *more than* 30 nucleotides long.

15. The isolated [genetic] *double-stranded DNA* construct according to [any one of claims 1, 2 or 3-] *claim 5*, wherein said structural gene sequence comprises a nucleotide sequence that is identical to said region of said target gene.

16. The method according to [any one of claims] *claim* 7[-9 or 10], wherein said [genetic] *double-stranded DNA* construct comprises two *identical* copies of said strucutral gene sequence.

17. The method according to [any one of claims] *claim* 7[-9 or 10], wherein said region of the target gene is [at least] *more than* 30 nucleotides long.

18. The method according to [any one of claims] *claim* 7[-9 or 10], wherein said structural gene sequence comprises a nucleotide sequence that is identical to said region of said target gene.

19. An animal cell comprising the [genetic] *double-stranded DNA* construct according to claim 11.

20. An animal cell comprising the [genetic] *double-stranded DNA* construct according to claim 13.

21. An animal cell comprising the [genetic] *double-stranded DNA* construct according to claim 14.

22. An animal cell comprising the [genetic] *double-stranded DNA* construct according to claim 15.

*23. The isolated double-stranded DNA construct according to claim 5, wherein the nucleic acid stuffer fragment is a sequence of 10-50 nucleotides.*

*24. The method according to claim 7, wherein the nucleic acid stuffer fragment is a sequence of 10-50 nucleotides.*

*25. The isolated double-stranded DNA construct according to claim 5, wherein the nucleic acid stuffer fragment is a sequence of 50-100 nucleotides.*

*26. The method according to claim 7, wherein the nucleic acid stuffer fragment is a sequence of 50-100 nucleotides.*

*27. The isolated double-stranded DNA construct according to claim 5, wherein the nucleic acid stuffer fragment is a sequence of 100-500 nucleotides.*

*28. The method according to claim 7, wherein the nucleic acid stuffer fragment is a sequence of 100-500 nucleotides.*

*29. An animal cell comprising the double-stranded DNA construct of claim 4.*

*30. The isolated double-stranded DNA construct according to claim 4, wherein said region of the target gene is 30 nucleotides long.*

*31. The method according to claim 10, wherein said region of the target gene is 30 nucleotides long.*

*32. The isolated double-stranded DNA construct according to claim 4, comprising two identical copies of said structural gene sequence.*

*33. The isolated double-stranded DNA construct according to claim 4, wherein said region of the target gene is more than 30 nucleotides long.*

*34. The isolated double-stranded DNA construct according to claim 4, wherein said structural gene sequence comprises a nucleotide sequence that is identical to said region of said target gene.*

*35. The method according to claim 10, wherein said double-stranded DNA construct comprises two identical copies of said structural gene sequence.*

*36. The method according to claim 10, wherein said region of the target gene is more than 30 nucleotides long.*

*37. The method according to claim 10, wherein said structural gene sequence comprises a nucleotide sequence that is identical to said region of said target gene.*

*38. An animal cell comprising the double-stranded DNA construct according to claim 30.*

*39. An animal cell comprising the double-stranded DNA construct according to claim 32.*

*40. An animal cell comprising the double-stranded DNA construct according to claim 33.*

*41. An animal cell comprising the double-stranded DNA construct according to claim 34.*

\* \* \* \* \*